(12) United States Patent
Bleicher et al.

(10) Patent No.: US 7,799,806 B2
(45) Date of Patent: Sep. 21, 2010

(54) SUBSTITUTED N-BENZYL PIPERIDINES AS SOMATOSTATIN RECEPTOR MODULATORS

(75) Inventors: Konrad Bleicher, Freiburg (DE); Andreas D. Christ, Arleshein (CH); Rainer E. Martin, Basel (CH); Peter Mohr, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/053,781

(22) Filed: Mar. 24, 2008

(65) Prior Publication Data

US 2008/0249101 A1    Oct. 9, 2008

(30) Foreign Application Priority Data

Apr. 4, 2007    (EP)    .................... 07105617

(51) Int. Cl.
A61K 31/445    (2006.01)

(52) U.S. Cl. ........... 514/323; 544/353; 546/118; 546/200; 548/257; 548/306.1; 548/470

(58) Field of Classification Search ........... 514/323; 544/353; 546/118, 200; 548/257, 306.1, 548/470
See application file for complete search history.

(56) References Cited

FOREIGN PATENT DOCUMENTS

WO    WO 2006/128803    12/2006
WO    WO 2007/025897    3/2007

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Ashton, M.J. et al, *J. Med. Chem*. (1994) 37:1696-1703.
Bailey, C.J. et al, *N. Eng. Jour. of Med*. (1996) 334, 574-579.
Burrin, D.G. et al, *Domest. Anim. Endocrinol*., (2003) 24:103-122.
Cejvan, K. et al, *Diabetes* (2003) 52, 1176-1181.
Cheikani, P.K. et al, *J. Physiol*. (2005) 288, R1695-R1706.
D'Alessio, D.A. et al, *J. Clin. Invest*. (1994) 93, 2263-2266.
Fagan, S.P. et al, *Surgery*, (1998) 124, 254-258.
Ferone, D. et al, *Dig. Liver Dis*. (2004) 36: S68-77.
Flint A, et al, *J. Clin. Invest*. (1998) 101, 515-520.
Ghamrawy, C.E. et al, *Peptides* (1999), 20: 305-311.
Gutzwiller, J et al, *Am. J. Physiol*, (1999) 276, R1541-1544.
Gutzwiller, J-P et al *Gut* (1999) 44, 81-88.
Haderslev, K. et al, (*Scand. J. Gastroenterol*. (2002), 37: 392-398.
Hansen, L. et al, *Am. J. Phys*. (2000), 278: E1010-1018.
Jeppesen, P.B., *J. Nutr*., (2003), 133: 3721-3724.
Kompis, I. et al, *Helv. Chim. Acta*, (1977) 60: 3025-3034.
Miki, T. et al, *Diabetes*, (2005) 54, 1056-1063.
Mortensen, L. et al, *Annals N.Y. Acad. Sci*, (2000), 921: 469-472.
Näslund, E. et al, *Int. J. Obesity*, (1999) 23, 304-311.
Norman, M. et al, *Ann. Surg*. (2002) 235, 767-774.
Plosker, G.L. et al, *Drugs*, (1999) 57, 409-438.
Sileno, A.P. et al, *Int. J. Obes. Lond*., (2006), 30: 68-72.
Small, J. et al, *Expert Opin. Investig. Drugs*, (2005) 14: 647-653.
Strowski, M. et al, *Endocrinology*, (2000) 141, 111-117.
Talme, T. et al, *Clin. Exp. Immunol*. (2001), 125: 71-79.
Tirone, T.A. et al. *Mol. Endocrinol*. (2003) 17, 93-106.
Toft-Nielsen, M.B. et al, *Diabetes Care*, (1999) 22, 1137-1143.
Turton, MD et al, *Nature*, (1996), 379, 69-72.
Vrang, A. et al, *Am. J. Physiol. Regul. Integr. Comp. Physiol*. (2006) 291: R367-R375.
White, A.W. et al, *Med. Chem*. (2000), 43: 4084-4097.
Zambre, Y. et al, *Biochem. Pharmacol* (1999), 57, 1159-1164.

* cited by examiner

*Primary Examiner*—James O. Wilson
*Assistant Examiner*—Douglas M Willis
(74) *Attorney, Agent, or Firm*—George W. Johnston; Dennis P. Tramaloni; Samuel H. Megerditchian

(57) ABSTRACT

This invention relates to compounds of the formula

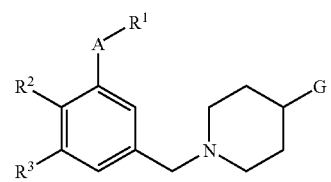

I wherein A, $R^1$ to $R^3$ are as defined in the claims and G is benzoimidazole, quinoxaline, benzotriazole, dihydro-imidazo[4,5-c]pyridinone and dihydro-isoindolone group as defined in the specification, and pharmaceutically acceptable salts thereof. The invention further relates to pharmaceutical compositions containing such compounds, to a process for their preparation and to their use for the treatment and/or prevention of diseases which are associated with the modulation of SST receptors subtype 5 such as diabetes mellitus.

18 Claims, No Drawings

SUBSTITUTED N-BENZYL PIPERIDINES AS SOMATOSTATIN RECEPTOR MODULATORS

PRIORITY TO RELATED APPLICATION(S)

This application claims the benefit of European Patent Application No. 07105617.0, filed Apr. 4, 2007, which is hereby incorporated by reference in its entirety.

FIELD OF THE INVENTION

The present invention is concerned with novel benzoimidazole, tetrahydro-quinoxaline, benzotriazole, dihydro-imidazo[4,5-c]pyridinone and dihydro-isoindolone derivatives, their manufacture, pharmaceutical compositions containing them and their use as medicaments. The active compounds of the present invention are useful in the prevention and/or treatment of diabetes mellitus and other disorders.

In particular, the present invention relates to compounds of the general formula I

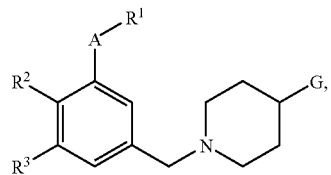

and pharmaceutically acceptable salts thereof.

The compounds of formula I possess pharmaceutical activity, in particular they are modulators of somatostatine receptor activity. More particularly, the compounds are antagonists of the somatostatine receptor subtype 5 (SSTR5).

All documents relied upon or cited to below are expressly incorporated herein by reference.

BACKGROUND

Diabetes mellitus is a systemic disease characterized by metabolic disorders involving insulin, carbohydrates, fats and proteins, and disorders in the structure and function of blood vessels. The primary symptom of acute diabetes is hyperglycemia, often accompanied by glucosuria, the presence in urine of large amounts of glucose, and polyuria, the excretion of large volumes of urine. Additional symptoms arise in chronic diabetes, including degeneration of the walls of blood vessels. Although many different human organs are affected by these vascular changes, the eyes and kidneys appear to be the most susceptible. As such, long-standing diabetes mellitus, even when treated with insulin, is a leading cause of blindness.

There are three recognized types of diabetes mellitus. Type I diabetes or insulin dependent diabetes mellitus (IDDM) is typically of juvenile onset; ketosis develops early in life with much more severe symptoms and has a near-certain prospect of later vascular involvement. Control of Type I diabetes is difficult and requires exogenous insulin administration. Type II diabetes or non-insulin dependent diabetes mellitus (NIDDM) is ketosis-resistant, generally develops later in life, is milder and has a more gradual onset. Gestational diabetes is related to Type II diabetes and associated with an increased risk of later development of that disease. Type III diabetes is malnutrition-related diabetes.

NIDDM is a condition that poses a major threat to the health of the citizens of the western world. NIDDM accounts for over 85% of diabetes incidence worldwide and about 160 million people are suffering from NIDDM. The incidence is expected to increase considerably within the next decades, especially in developing countries. NIDDM is associated with morbidity and premature mortality resulting from serious complications, e.g., cardiovascular disease (G. C. Weir and J. L. Leahy, Pathogenesis of non-insulin dependent (Type II) diabetes mellitus, in *Joslin's Diabetes Mellitus* (Eds. C. R. Kahn and G. C. Weir), 13$^{th}$ Edition, 1994, Lea & Febiger, Malvern, Pa., pp. 240-264). NIDDM is characterized by both fasting and post-prandial hyperglycemia resulting from abnormalities in insulin secretion and insulin action (G. C. Weir et al., vide supra).

The hyperglycemia in patients suffering from NIDDM can usually be initially treated by dieting, but eventually most NIDDM patients have to take oral antidiabetic agents and/or insulin injections to normalize their blood glucose levels. The introduction of orally effective hypoglycemic agents was an important development in the treatment of hyperglycemia by lowering blood glucose levels. Currently, the most widely used oral antidiabetic agents are the sulfunylureas, which act by increasing the secretion of insulin from the pancreas (H. E. Lebovitz, Oral antidiabetic agents, in *Joslin's Diabetes Mellitus* (Eds. C. R. Kahn and G. C. Weir), 13$^{th}$ Edition, 1994, Lea & Febiger, Malvern, Pa., pp. 508-529), the biguanides (e.g., metformin) which act on the liver and periphery by unknown mechanisms (C. J. Bailey, M. R. C. Path and R. C. Turner *N. Engl. J. Med*. 1996, 334, 574-579) and the thiazolidinediones (e.g., rosiglitazone/Avandia®), which enhance the effects of insulin at peripheral target sites (G. L. Plosker and D. Faulds *Drugs* 1999, 57, 409-438). These existing oral therapies which comprise a wide variety of biguanide, sulfonylurea and thiazolidinedione derivatives have been used clinically as hypoglycemic agents. However, all three classes of compound have side effects. The biguanides, for example metformin, are unspecific and in certain cases have been associated with lactic acidosis, and need to be given over a longer period of time, i.e. they are not suitable for acute administration (C. J. Bailey et al., vide supra). The sulfonylureas, though having good hypoglycemic activity, require great care during use because they frequently cause serious hypoglycemia and are most effective over a period of circa ten years. The thiazolidinediones may cause weight gain and deterioration of cardiovascular function following chronic administration (G. L. Plosker and D. Faulds, vide supra) and troglitazone has been associated with the occurrence of serious hepatic dysfunction.

Thus, there is a significant and rising need for antidiabetic drugs that have novel mechanisms of action, thereby avoiding side effects produced by known therapies. The hormone somatostatin (SST) is primarily produced in the intestinal tract and in the pancreas. In addition it acts as a neurotransmitter. The hormone is involved through its receptors in the regulation of several other hormones and in immunoregulation. In particular, SST suppresses the secretion of insulin by pancreatic β cells and the secretion of glucagon-like peptide 1 (GLP-1) by L cells. GLP-1 in turn is one of the most potent stimulators of insulin production and secretion and is a trophic factor for β cells. In addition, GLP-1 directly increases peripheral glucose disposal (e.g., D. A. D'Alessio, S. E. Kahn, C. R. Leusner and J. W. Ensinck, *J. Clin. Invest*. 1994, 93, 2263-2266). β and L cells express SST receptor subtype 5 (SSTR5) and agonizing this receptor suppresses insulin and GLP-1 secretion in humans and in animal models (e.g., Y. Zambre, Z. Ling, M.-C. Chen, X. Hou, C.-W. Woon, M. Culler, J. H. Taylor, D. H. Coy, C. van Schravendijk, F. Schuit, D. G. Pipeleers and D. L. Eizirik *Biochem. Pharmacol.* 1999, 57, 1159-1164; S. P. Fagan, A. Azizzadeh, S. Moldovan, M. K. Ray, T. E. Adrian, X. Ding, D. H. Coy and F. C. Brunicardi *Surgery* 1998, 124, 254-258; M. Norman, S. Moldovan, V. Seghers, X.-P. Wang, F. J. DeMayo and F. C. Brunicardi *Ann. Surg.* 2002, 235, 767-774; T. A. Tirone, M. A. Norman, S. Moldovan, F. J. DeMayo, X.-P. Wang, F. C. Brunicardi *Pancreas* 2003, 26, e67-73; M. Z. Strowski, M. Köhler, H. Y. Chen, M. E. Trumbauer, Z. Li, D. Szalkowski, S. Gopal-Truter, J. K. Fisher, J. M. Schaeffer, A. D. Blake, B. B. Zhang and H. A. Wilkinson *Mol. Endocrinol.* 2003, 17, 93-106).

Consequently, antagonizing the effect of SST would lead to increased peripheral glucose disposal and higher plasma insulin concentrations. Additionally, SSTR5 knockout mice demonstrated higher insulin sensitivity than littermates (M. Z. Strowski, M. Köhler et al., vide supra). In patients suffering from impaired glucose tolerance and NIDDM these combined effects would moderate the dangerous hyperglycemia and accordingly reduce the risk of tissue damage. If such SSTR5 antagonists are sufficiently selective over the other four SST receptors, little influence is expected on secretion of other hormones. Particularly, selectivity over SST receptor subtype 2 avoids influences on glucagon secretion (K. Cejvan, D. H. Coy and S. Efendic *Diabetes* 2003, 52, 1176-1181; M. Z. Strowski, R. M. Parmar, A. D. Blake and J. M. Schaeffer *Endocrinology* 2000, 141, 111-117). Advantageous over established therapies is the dual mechanism of action to increase insulin secretion (directly on pancreatic β cells and indirectly through GLP-1 release from L cells) and to increase glucose disposal, whereby SSTR5 antagonists could have the potential to beneficially influence insulin resistance in patients with NIDDM. In summary, SSTR5 antagonists are expected to beneficially influence NIDDM, the underlying impaired fasting glucose and impaired glucose tolerance, as well as complications of long-standing, insufficiently controlled diabetes mellitus.

GLP-1 is known as an endogenous regulator of gastrointestinal motility and of food intake reducing appetite as shown in laboratory animals, healthy volunteers and patients with NIDDM (E. Näslund, B. Barkeling, N. King, M. Gutniak, J. E. Blundell, J. J. Holst, S. Rössner and P. M. Hellström *Int. J. Obes.* 1999, 23, 304-311; J.-P. Gutzwiller, B. Göke, J. Drewe, P. Hildebrand, S. Ketterer, D. Handschin, R. Winterhalder, D. Conen and C. Beglinger *Gut* 1999, 44, 81-88; J.-P. Gutzwiller, J. Drewe, B. Göke, H. Schmidt, B. Rohrer, J. Larcida and C. Beglinger *Am. J. Physiol.* 1999, 276, R1541-1544; M. D. Turton, D. O'Shea, I. Gunn, S. A. Beak, C. M. Edwards, K. Meeran, S. J. Choi, G. M. Taylor, M. M. Heath, P. D. Lambert, J. P. Wilding, D. M. Smith, M. A. Ghatei, J. Herbert and S. R. Bloom *Nature* 1996, 379, 69-72; A. Flint, A. Raben, A. Astrup and J. J. Hoist *J. Clin. Invest.* 1998, 101, 515-520; M. B. Toft-Nielsen, S. Madsbad and J. J. Holst *Diabetes Care* 1999, 22, 1137-1143; P. K. Cheikani, A. C. Haver and R. D. Reidelberger *Am. J. Physiol.* 2005, 288, R1695-R1706; T. Miki, K. Minami, H. Shinozaki, K. Matsumura, A. Saraya, H. Ikeda, Y. Yamada, J. J. Holst and S. Seino *Diabetes* 2005, 54, 1056-1063); thus, elevated GLP-1 will also counteract obesity, a typical condition associated with and leading to NIDDM.

GLP-1 further co-localizes with peptide YY (PYY). Thus, PYY could potentially also be increased by SSTR5 antagonists (K. Mortensen, L. L. Lundby and C. Orsov *Annals N.Y. Acad. Sci.* 2000, 921, 469-472). There is evidence that PYY increases satiety, reduces body weight and improves glycemic control (N. Vrang, A. N. Madsen, C. M. Tang, G. Hansen and P. J. Larsen *Am. J. Physiol. Regul. Integr. Comp. Physiol.* 2006, 291, R367-R375; A. P. Sileno, G. C. Brandt, B. M. Spain and S. C. Quay *Int. J. Obes. Lond.* 2006, 30, 68-72; C. J. Small and S. R. Bloom *Expert Opin. Investig. Drugs* 2005, 14, 647-653). Taken together, SSTR5 antagonists could have the potential to act on obesity also through PYY.

GLP-1 is co-secreted with GLP-2 that is, consequently, also regulated by SST through SSTR5 (L. Hansen, B. Hartmann, T. Bisgaard, H. Mineo, P. N. Jørgensen and J. J. Holst *Am. J. Phys.* 2000, 278, E1010-1018). GLP-2 is enterotrophic and beneficial in patients with malabsorption of certain origins, such as short bowel syndrome (D. G. Burrin, B. Stoll and X. Guan *Domest. Anim. Endocrinol.* 2003, 24, 103-122; K. V. Haderslev, P. B. Jeppesen, B. Hartmann, J. Thulesen, H. A. Sorensen, J. Graff, B. S. Hansen, F. Tofteng, S. S. Poulsen, J. L. Madsen, J. J. Holst, M. Staun and P. B. Mortensen *Scand. J. Gastroenterol.* 2002, 37, 392-398; P. B. Jeppesen *J. Nutr.* 2003, 133, 3721-3724).

Moreover, there is increasing evidence for a role of SST on immune cells and expression of SSTR5 on activated T lymphocytes (T. Talme, J. Ivanoff, M. Hägglund, R. J. J. van Neerven, A. Ivanoff and K. G. Sundqvist *Clin. Exp. Immunol.* 2001, 125, 71-79; D. Ferone, P. M. van Hagen, C. Semino, V. A. Dalm, A. Barreca, A. Colao, S. W. J. Lamberts, F. Minuto and L. J. Hofland *Dig. Liver Dis.* 2004, 36, S68-77; C. E. Ghamrawy, C. Rabourdin-Combe and S. Krantic *Peptides* 1999, 20, 305-311). Consequently, SSTR5 antagonists could also prove valuable in treating diseases characterized by a disturbed immune system, such as inflammatory bowel disease.

SUMMARY OF THE INVENTION

In an embodiment of the present invention, provided is a compound of formula I:

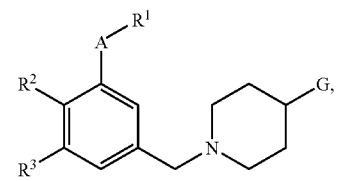

wherein

A is —O— or —NH—;

$R^1$ is selected from the group consisting of $C_{2-7}$-alkyl, $C_{2-7}$-alkenyl, $C_{3-7}$-alkinyl, $C_{3-7}$-cycloalkyl, halogen-$C_{1-7}$-alkyl, $C_{1-7}$-alkoxy-$C_{1-7}$-alkyl and benzyl;

$R^2$ is selected from the group consisting of hydrogen, $C_{1-7}$-alkyl, hydroxy, $C_{1-7}$-alkoxy, $C_{2-7}$-alkenyloxy, hydroxy-$C_{1-7}$-alkoxy, $C_{1-7}$-alkoxy-$C_{1-7}$-alkoxy, —O-benzyl, —O—$C_{3-7}$-cycloalkyl, unsubstituted phenyl or phenyl substituted by one to three groups independently selected from $C_{1-7}$-alkyl, halogen and $C_{1-7}$-alkoxy, halogen, halogen-$C_{1-7}$-alkyl, halogen-$C_{1-7}$-alkoxy, amino, pyrrolyl, imidazolyl and —C(O)OR$^4$, wherein $R^4$ is $C_{1-7}$-alkyl;

$R^3$ is hydrogen or ($C_{1-7}$-alkoxy, or $R^2$ and $R^3$ are bonded to each other to form a ring together with the carbon atoms they are attached to and $R^2$ and $R^3$ together are —O—C(CH$_3$)$_2$—CH═CH—;

G is selected from the groups

G1 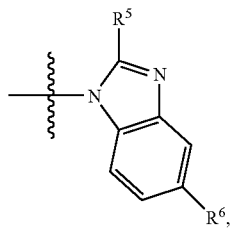

G2 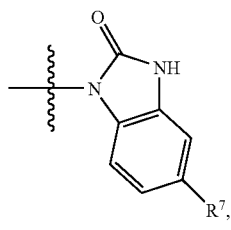

G3 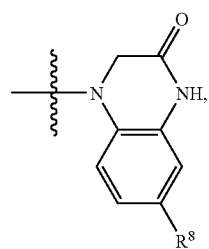

G4 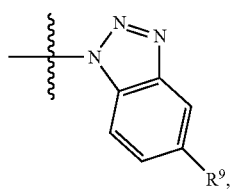

G5 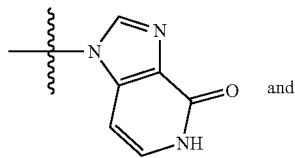

G6 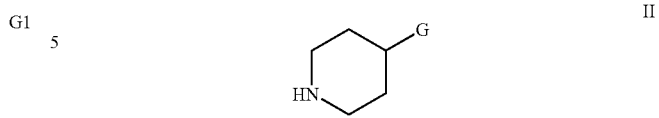

wherein
R$^5$ is hydrogen or C$_{1-7}$-alkyl;
R$^6$, R$^7$, R$^8$ and R$^9$ are —COOH;
R$^{10}$ is hydrogen or C$_{1-7}$-alkoxy;

and pharmaceutically acceptable salts thereof.

In another embodiment of the present invention, provided is a process for the manufacture of compounds according to formula I, comprising the steps of:

a) reacting a piperidine of the formula

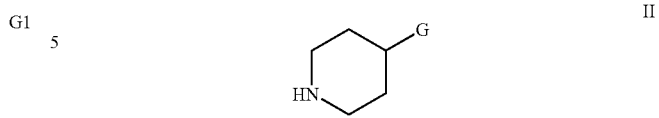

wherein G is as defined above, with an aldehyde of the formula

wherein A and R$^1$ to R$^3$ are as defined above, by employing a reducing agent to obtain a compound of the formula

and, if desired, converting the compound of formula I into a pharmaceutically acceptable salt; or, alternatively, b) alkylating a piperidine of the formula

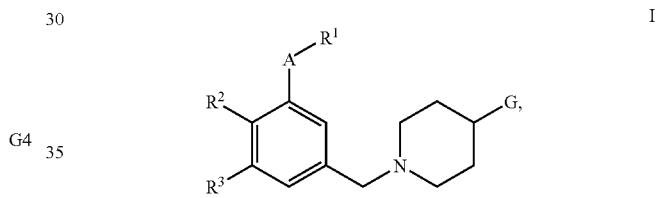

wherein G is as defined above, with a compound of the formula

wherein A and R$^1$ to R$^3$ are as defined above and X is a leaving group, under basic conditions to obtain a compound or formula

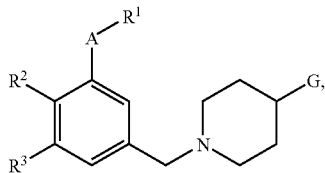

I and, if desired, converting the compound of formula I into a pharmaceutically acceptable salt; or, alternatively,
c) reacting a compound of the general formula

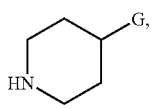

II wherein G is as defined above, with a compound of the formula

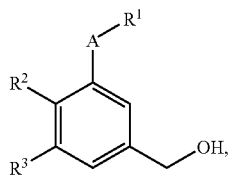

V wherein A and $R^1$ to $R^3$ are as defined above, in the presence of a trialkylphosphine and a diazo-compound to obtain a compound of the formula

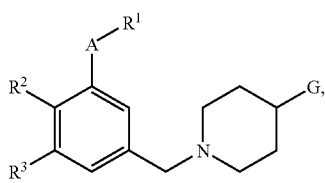

I and, if desired, converting the compound of formula I into a pharmaceutically acceptable salt.

In a further embodiment of the present invention, provided is a pharmaceutical composition, comprising a therapeutically effective amount of a compound according to formula I as well as a pharmaceutically acceptable carrier and/or adjuvant.

In a yet another embodiment of the present invention, provided is a method for the treatment and/or prevention of diseases which are associated with the modulation of SST receptors subtype 5, comprising the step of administering a therapeutically effective amount of a compound according to formula I to a human being or animal in need thereof.

DETAILED DESCRIPTION

The present invention provides for selective, directly acting SSTR5 antagonists. Such antagonists are useful as therapeutically active substances, particularly in the treatment and/or prevention of diseases which are associated with the modulation of SST receptors subtype 5.

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination, signifies a straight-chain or branched-chain alkyl group with 1 to 7 carbon atoms, preferably a straight or branched-chain alkyl group with 1 to 4 carbon atoms. Examples of straight-chain and branched $C_1$-$C_7$ alkyl groups are methyl, ethyl, propyl, isopropyl, butyl, isobutyl, tert-butyl, the isomeric pentyls, the isomeric hexyls and the isomeric heptyls, preferably methyl, ethyl and isopropyl, and most preferred the groups specifically exemplified herein.

The term "lower alkenyl" or "$C_{2-7}$-alkenyl", alone or in combination, signifies a straight-chain or branched hydrocarbon residue comprising an olefinic bond and up to 7, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl (allyl).

The term "lower alkinyl" or "$C_{3-7}$-alkinyl" signifies a straight-chain or branched hydrocarbon residue comprising a triple bond and up to 7, preferably up to 6, particularly preferred up to 4 carbon atoms. Examples of alkinyl groups are 2-propinyl, 2-butinyl and 3-butinyl. A preferred example is 2-propinyl.

The term "cycloalkyl" or "$C_{3-7}$-cycloalkyl" refers to a monovalent carbocyclic radical of three to seven, preferably three to five carbon atoms. This term is further exemplified by radicals such as cyclopropyl, cyclobutyl, cyclopentyl, cyclohexyl and cycloheptyl, with cyclobutyl being especially preferred.

The term "alkoxy" refers to the group R'—O—, wherein R' is alkyl. The term "lower alkoxy" or "$C_{1-7}$-alkoxy" refers to the group R'—O—, wherein R' is lower alkyl and the term "lower alkyl" has the previously given significance. Examples of lower alkoxy groups are e.g., methoxy, ethoxy, n-propoxy, isopropoxy, n-butoxy, iso-butoxy, sec-butoxy and tert-butoxy, preferably methoxy and ethoxy and most preferred the groups specifically exemplified herein.

The term "lower alkoxyalkyl" or "$C_{1-7}$-alkoxy-$C_{1-7}$-alkyl" refers to lower alkyl groups as defined above wherein at least one of the hydrogen atoms of the lower alkyl group is replaced by an alkoxy group as defined above. Among the preferred lower alkoxyalkyl groups are methoxymethyl, methoxyethyl and ethoxymethyl.

The term "lower alkoxyalkoxy" or "$C_{1-7}$-alkoxy-$C_{1-7}$-alkoxy" refers to lower alkoxy groups as defined above wherein at least one of the hydrogen atoms of the lower alkoxy group is replaced by an alkoxy group as defined above. Among the preferred lower alkoxyalkoxy groups are 2-methoxy-ethoxy and 3-methoxy-propoxy.

The term "halogen" refers to fluorine, chlorine, bromine and iodine, with fluorine, chlorine and bromine being preferred.

The term "lower halogenalkyl" or "halogen-$C_{1-7}$-alkyl" refers to lower alklyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, difluoroethyl, fluoromethyl and chloromethyl, with trifluoromethyl and difluoroethyl being especially preferred.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluoromethoxy and chloromethoxy, with trifluoromethoxy being especially preferred.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl, but also groups having two hydroxy groups such as 2-hydroxy-1-hydroxymethyl-ethyl.

The term "lower hydroxyalkoxy" or "hydroxy-$C_{1-7}$-alkoxy" refers to lower alkoxy groups as defined above wherein at least one of the hydrogen atoms of the lower alkoxy group is replaced by a hydroxy group. Examples of lower hydroxyalkoxy groups are hydroxymethoxy or hydroxyethoxy.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g., hydrated. The solvation can be effected in the course of the manufacturing process or can take place, e.g., as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In detail, the present invention relates to compounds of the general formula I

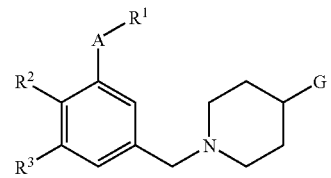

wherein

A is —O— or —NH—;

$R^1$ is selected from the group consisting of $C_{2-7}$-alkyl, $C_{2-7}$-alkenyl, $C_{1-7}$-alkinyl, $C_{3-7}$-cycloalkyl, halogen-$C_{1-7}$-alkyl, $C_{1-7}$-alkoxy-$C_{1-7}$-alkyl and benzyl;

$R^2$ is selected from the group consisting of hydrogen, $C_{1-7}$-alkyl, hydroxy, $C_{1-7}$-alkoxy, $C_{2-7}$-alkenyloxy, hydroxy-$C_{1-7}$-alkoxy, $C_{1-7}$-alkoxy-$C_{1-7}$-alkoxy, —O-benzyl, —O—$C_{3-7}$-cycloalkyl, unsubstituted phenyl or phenyl substituted by one to three groups independently selected from $C_{1-7}$-alkyl, halogen and $C_{1-7}$-alkoxy, halogen, halogen-$C_{1-7}$-alkyl, halogen-$C_{1-7}$-alkoxy, amino, pyrrolyl, imidazolyl and —C(O)$OR^4$, wherein $R^5$ is $C_{1-7}$-alkyl;

$R^3$ is hydrogen or $C_{1-7}$-alkoxy;

or $R^2$ and $R^3$ are bonded to each other to form a ring together with the carbon atoms they are attached to and $R^2$ and $R^3$ together are —O—C(CH$_3$)$_2$—CH=CH—;

G is selected from the groups

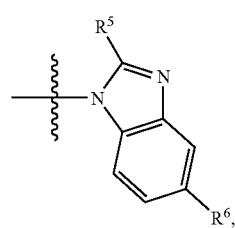

G1

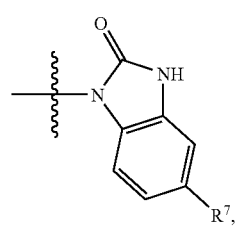

G2

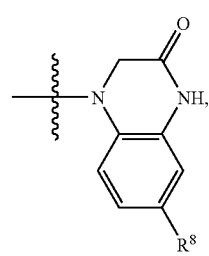

G3

-continued

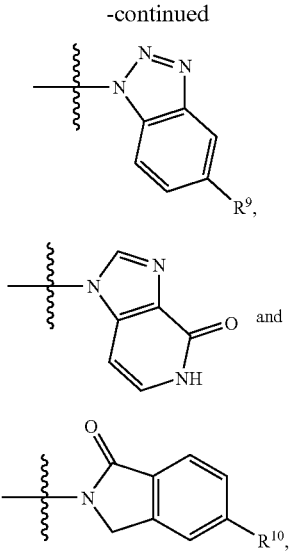

wherein
$R^5$ is hydrogen or $C_{1-7}$-alkyl;
$R^6$, $R^7$, $R^8$ and $R^9$ are —COOH;
$R^{10}$ is hydrogen or $C_{1-7}$-alkoxy;

and pharmaceutically acceptable salts thereof.

Preferred compounds of formula I of the present invention are also those, wherein A is O.

A further group of compounds of formula I are those, wherein A is NH.

Also preferred are compounds of formula I according to the invention, wherein $R^1$ is selected from the group consisting of $C_{2-7}$-alkyl, $C_{2-7}$-alkenyl, $C_{3-7}$-alkinyl, $C_{3-7}$-cycloalkyl and halogen-$C_{1-7}$-alkyl. Especially preferred are those compounds of formula I, wherein $R^2$ is selected from the group consisting of ethyl, propyl, isopropyl, allyl, 2-fluoroethyl, butyl, isobutyl, cyclopentyl and 2-propynyl, with those compounds, wherein $R^2$ is ethyl or isopropyl, being most preferred.

Further preferred compounds of formula I according to the present invention are those, wherein $R^2$ is selected from the group consisting of
hydrogen, $C_{1-7}$-alkyl, hydroxy, $C_{1-7}$-alkoxy, $C_{2-7}$-alkenyloxy, —O-benzyl, —O—$C_{3-7}$-cycloalkyl,
unsubstituted phenyl or phenyl substituted by one to three groups independently selected from $C_{1-7}$-alkyl, halogen and $C_{1-7}$-alkoxy,
halogen, halogen-$C_{1-7}$-alkoxy, amino, pyrrolyl, imidazolyl and
—C(O)O$R^4$, wherein $R^4$ is $C_{1-7}$-alkyl.

More preferred are those compounds of formula I, wherein $R^2$ is selected from the group consisting of group consisting of hydrogen, $C_{1-7}$-alkoxy, halogen, halogen-$C_{1-7}$-alkoxy, pyrrolyl, phenyl substituted by halogen and —C(O)O$R^4$, wherein $R^4$ is $C_{1-7}$-alkyl, with those compounds, wherein $R^2$ is halogen, being especially preferred. Most preferably, $R^2$ is chloro.

Furthermore, compounds of formula I of the present invention are preferred, wherein $R^3$ is hydrogen or $C_{1-7}$-alkoxy.

Another group of preferred compounds of formula I according to the present invention are those, wherein $R^2$ and $R^3$ are bonded to each other to form a ring together with the carbon atoms they are attached to and $R^2$ and $R^3$ together are —O—C(CH$_3$)$_2$—CH=CH—. These are compounds of the formula Ix:

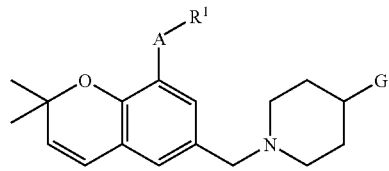

Preferred are further compounds of formula I according to the present invention, wherein G is

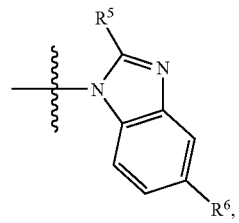

and wherein $R^5$ is hydrogen or $C_{1-7}$-alkyl and $R^6$ is —COOH.
More preferably, $R^5$ is methyl.

Furthermore, compounds of formula I according to the invention are preferred, wherein G is

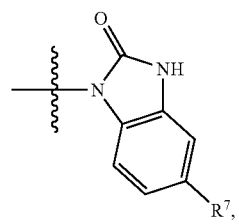

and wherein $R^7$ is —COOH.

Also preferred are compounds of formula I according to the present invention, wherein G is

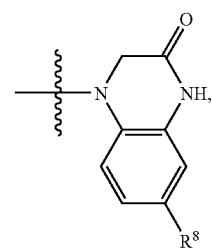

and wherein $R^8$ is —COOH.

Further preferred are compounds of formula I according to the invention, wherein G is

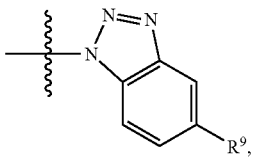

and wherein R⁹ is —COOH.

Also preferred are compounds of formula I according to the invention, wherein G is

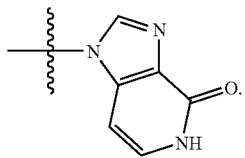

Furthermore, compounds of formula I according to the invention are preferred, wherein G is

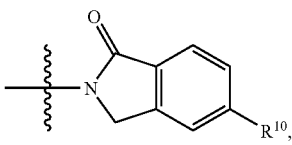

and wherein $R^{10}$ is hydrogen or $C_{1-7}$-alkoxy.

Especially preferred are those compounds of formula I, wherein $R^{10}$ is methoxy.

Examples of preferred compounds of formula I are the following:

1-[1-(3-ethoxy-4-fluoro-benzyl)-piperidin-4-yl]-2-methyl-1H-benzoimidazole-5-carboxylic acid,
1-[1-(4-chloro-3-ethoxy-benzyl)-piperidin-4-yl]-2-methyl-1H-benzoimidazole-5-carboxylic acid,
1-[1-(4-allyloxy-3-ethoxy-benzyl)-piperidin-4-yl]-2-methyl-1H-benzoimidazole-5-carboxylic acid,
1-[1-(3-ethoxy-4-isopropoxy-benzyl)-piperidin-4-yl]-2-methyl-1H-benzoimidazole-5-carboxylic acid,
1-[1-(3-ethoxy-4-isobutoxy-benzyl)-piperidin-4-yl]-2-methyl-1H-benzoimidazole-5-carboxylic acid,
1-{1-[3-ethoxy-4-(1-ethyl-propoxy)-benzyl]-piperidin-4-yl}-2-methyl-1H-benzoimidazole-5-carboxylic acid,
1-[1-(4-cyclopentyloxy-3-ethoxy-benzyl)-piperidin-4-yl]-2-methyl-1H-benzoimidazole-5-carboxylic acid,
1-[1-(4-benzyloxy-3-ethoxy-benzyl)-piperidin-4-yl]-2-methyl-1H-benzoimidazole-5-carboxylic acid,
1-[1-(4-difluoromethoxy-3-ethoxy-benzyl)-piperidin-4-yl]-2-methyl-1H-benzoimidazole-5-carboxylic acid,
1-[1-(3-isopropoxy-4-methoxy-benzyl)-piperidin-4-yl]-2-methyl-1H-benzoimidazole-5-carboxylic acid,
1-{1-[3-(2-fluoro-ethoxy)-4-methoxy-benzyl]-piperidin-4-yl}-2-methyl-1H-benzoimidazole-5-carboxylic acid,
1-[1-(3-isobutoxy-4-methoxy-benzyl)-piperidin-4-yl]-2-methyl-1H-benzoimidazole-5-carboxylic acid,
1-[1-(3-cyclopentyloxy-4-methoxy-benzyl)-piperidin-4-yl]-2-methyl-1H-benzoimidazole-5-carboxylic acid,
1-[1-(8-ethoxy-2,2-dimethyl-2H-chromen-6-ylmethyl)-piperidin-4-yl]-2-methyl-1H-benzoimidazole-5-carboxylic acid,
1-[1-(3,5-diethoxy-benzyl)-piperidin-4-yl]-2-methyl-1H-benzoimidazole-5-carboxylic acid,
1-[1-(3,5-diisopropoxy-benzyl)-piperidin-4-yl]-2-methyl-1H-benzoimidazole-5-carboxylic acid,
1-[1-(3,5-diethoxy-4-fluoro-benzyl)-piperidin-4-yl]-2-methyl-1H-benzoimidazole-5-carboxylic acid,
1-[1-(4-chloro-3,5-diethoxy-benzyl)-piperidin-4-yl]-2-methyl-1H-benzoimidazole-5-carboxylic acid,
1-[1-(4-bromo-3,5-diethoxy-benzyl)-piperidin-4-yl]-2-methyl-1H-benzoimidazole-5-carboxylic acid,
1-[1-(4-amino-3,5-diethoxy-benzyl)-piperidin-4-yl]-2-methyl-1H-benzoimidazole-5-carboxylic acid,
1-[1-(3,5-diethoxy-4-pyrrol-1-yl-benzyl)-piperidin-4-yl]-2-methyl-1H-benzoimidazole-5-carboxylic acid,
1-[1-(3,5-diethoxy-4-ethoxycarbonyl-benzyl)-piperidin-4-yl]-2-methyl-1H-benzoimidazole-5-carboxylic acid,
1-[1-(2,6-diethoxy-4'-fluoro-biphenyl-4-ylmethyl)-piperidin-4-yl]-2-methyl-1H-benzoimidazole-5-carboxylic acid,
1-[1-(3-ethoxy-4-fluoro-benzyl)-piperidin-4-yl]-2-oxo-2,3-dihydro-1H-benzoimidazole-5-carboxylic acid,
1-[1-(4-chloro-3-ethoxy-benzyl)-piperidin-4-yl]-2-oxo-2,3-dihydro-1H-benzoimidazole-5-carboxylic acid,
1-[1-(3-ethoxy-4-hydroxy-benzyl)-piperidin-4-yl]-2-oxo-2,3-dihydro-1H-benzoimidazole-5-carboxylic acid,
1-[1-(3-ethoxy-4-methoxy-benzyl)-piperidin-4-yl]-2-oxo-2,3-dihydro-1H-benzoimidazole-5-carboxylic acid,
1-[1-(3,4-diethoxy-benzyl)-piperidin-4-yl]-2-oxo-2,3-dihydro-1H-benzoimidazole-5-carboxylic acid,
1-[1-(4-allyloxy-3-ethoxy-benzyl)-piperidin-4-yl]-2-oxo-2,3-dihydro-1H-benzoimidazole-5-carboxylic acid,
1-[1-(3-ethoxy-4-isopropoxy-benzyl)-piperidin-4-yl]-2-oxo-2,3-dihydro-1H-benzoimidazole-5-carboxylic acid,
1-[1-(3-ethoxy-4-isobutoxy-benzyl)-piperidin-4-yl]-2-oxo-2,3-dihydro-1H-benzoimidazole-5-carboxylic acid,
1-{1-[3-ethoxy-4-(1-ethyl-propoxy)-benzyl]-piperidin-4-yl}-2-oxo-2,3-dihydro-1H-benzoimidazole-5-carboxylic acid,
1-[1-(4-cyclopentyloxy-3-ethoxy-benzyl)-piperidin-4-yl]-2-oxo-2,3-dihydro-1H-benzoimidazole-5-carboxylic acid,
1-[1-(4-benzyloxy-3-ethoxy-benzyl)-piperidin-4-yl]-2-oxo-2,3-dihydro-1H-benzoimidazole-5-carboxylic acid,
1-[1-(4-difluoromethoxy-3-ethoxy-benzyl)-piperidin-4-yl]-2-oxo-2,3-dihydro-1H-benzoimidazole-5-carboxylic acid,
1-[1-(4-methoxy-3-propoxy-benzyl)-piperidin-4-yl]-2-oxo-2,3-dihydro-1H-benzoimidazole-5-carboxylic acid,
1-{1-[3-(2-fluoro-ethoxy)-4-methoxy-benzyl]-piperidin-4-yl}-2-oxo-2,3-dihydro-1H-benzoimidazole-5-carboxylic acid,
1-[1-(3-butoxy-4-methoxy-benzyl)-piperidin-4-yl]-2-oxo-2,3-dihydro-1H-benzoimidazole-5-carboxylic acid,
1-[1-(3-isobutoxy-4-methoxy-benzyl)-piperidin-4-yl]-2-oxo-2,3-dihydro-1H-benzoimidazole-5-carboxylic acid,
1-[1-(3-cyclopentyloxy-4-methoxy-benzyl)-piperidin-4-yl]-2-oxo-2,3-dihydro-1H-benzoimidazole-5-carboxylic acid,
1-[1-(8-ethoxy-2,2-dimethyl-2H-chromen-6-ylmethyl)-piperidin-4-yl]-2-oxo-2,3-dihydro-1H-benzoimidazole-5-carboxylic acid
1-[1-(3,5-diethoxy-benzyl)-piperidin-4-yl]-2-oxo-2,3-dihydro-1H-benzoimidazole-5-carboxylic acid,
1-[1-(3,5-diisopropoxy-benzyl)-piperidin-4-yl]-2-oxo-2,3-dihydro-1-benzoimidazole-5-carboxylic acid, 1-[1-(3,5-diethoxy-4-ethoxycarbonyl-benzyl)-piperidin-4-yl]-2-oxo-2,3-dihydro-1H-benzoimidazole-5-carboxylic acid,
1-[1-(3,5-diethoxy-4-fluoro-benzyl)-piperidin-4-yl]-2-oxo-2,3-dihydro-1H-benzoimidazole-5-carboxylic acid,
1-[1-(4-chloro-3,5-diethoxy-benzyl)-piperidin-4-yl]-2-oxo-2,3-dihydro-1H-benzoimidazole-5-carboxylic acid,
1-[1-(4-bromo-3,5-diethoxy-benzyl)-piperidin-4-yl]-2-oxo-2,3-dihydro-1H-benzoimidazole-5-carboxylic acid,
1-[1-(4-amino-3,5-diethoxy-benzyl)-piperidin-4-yl]-2-oxo-2,3-dihydro-1H-benzoimidazole-5-carboxylic acid,
1-[1-(3,5-diethoxy-4-pyrrol-1-yl-benzyl)-piperidin-4-yl]-2-oxo-2,3-dihydro-1H-benzoimidazole-5-carboxylic acid,
1-[1-(4-chloro-3-ethoxy-benzyl)-piperidin-4-yl]-3-oxo-1,2,3,4-tetrahydro-quinoxaline-6-carboxylic acid,
1-[1-(4-difluoromethoxy-3-ethoxy-benzyl)-piperidin-4-yl]-3-oxo-1,2,3,4-tetrahydro-quinoxaline-6-carboxylic acid,
1-[1-(3-cyclopentyloxy-4-methoxy-benzyl)-piperidin-4-yl]-3-oxo-1,2,3,4-tetrahydro-quinoxaline-6-carboxylic acid,
1-[1-(3,5-diisopropoxy-benzyl)-piperidin-4-yl]-3-oxo-1,2,3,4-tetrahydro-quinoxaline-6-carboxylic acid,
1-[1-(3,5-diethoxy-4-ethoxycarbonyl-benzyl)-piperidin-4-yl]-3-oxo-1,2,3,4-tetrahydro-quinoxaline-6-carboxylic acid,
1-[1-(3,5-diethoxy-4-fluoro-benzyl)-piperidin-4-yl]-3-oxo-1,2,3,4-tetrahydro-quinoxaline-6-carboxylic acid,
1-[1-(4-chloro-3,5-diethoxy-benzyl)-piperidin-4-yl]-3-oxo-1,2,3,4-tetrahydro-quinoxaline-6-carboxylic acid,
1-[1-(4-bromo-3,5-diethoxy-benzyl)-piperidin-4-yl]-3-oxo-1,2,3,4-tetrahydro-quinoxaline-6-carboxylic acid,
1-[1-(3,5-diethoxy-4-pyrrol-1-yl-benzyl)-piperidin-4-yl]-3-oxo-1,2,3,4-tetrahydro-quinoxaline-6-carboxylic acid,
1-[1-(2,6-diethoxy-4'-fluoro-biphenyl-4-ylmethyl)-piperidin-4-yl]-3-oxo-1,2,3,4-tetrahydro-quinoxaline-6-carboxylic acid,
1-[1-(3-ethoxy-4-fluoro-benzyl)-piperidin-4-yl]-1H-benzotriazole-5-carboxylic acid,
1-[1-(4-chloro-3-ethoxy-benzyl)-piperidin-4-yl]-1H-benzotriazole-5-carboxylic acid,
1-[1-(3-ethoxy-4-hydroxy-benzyl)-piperidin-4-yl]-1H-benzotriazole-5-carboxylic acid,
1-[1-(3-ethoxy-4-methoxy-benzyl)-piperidin-4-yl]-1H-benzotriazole-5-carboxylic acid,
1-[1-(3,4-diethoxy-benzyl)-piperidin-4-yl]-1H-benzotriazole-5-carboxylic acid,
1-[1-(4-allyloxy-3-ethoxy-benzyl)-piperidin-4-yl]-1H-benzotriazole-5-carboxylic acid,
1-[1-(3-ethoxy-4-isopropoxy-benzyl)-piperidin-4-yl]-1H-benzotriazole-5-carboxylic acid,
1-[1-(3-ethoxy-4-isobutoxy-benzyl)-piperidin-4-yl]-1H-benzotriazole-5-carboxylic acid,
1-{1-[3-ethoxy-4-(1-ethyl-propoxy)-benzyl]-piperidin-4-yl}-1H-benzotriazole-5-carboxylic acid,
1-[1-(4-cyclopentyloxy-3-ethoxy-benzyl)-piperidin-4-yl]-1H-benzotriazole-5-carboxylic acid,
1-[1-(4-benzyloxy-3-ethoxy-benzyl)-piperidin-4-yl]-1H-benzotriazole-5-carboxylic acid,
1-[1-(4-difluoromethoxy-3-ethoxy-benzyl)-piperidin-4-yl]-1H-benzotriazole-5-carboxylic acid,
1-[1-(4-methoxy-3-propoxy-benzyl)-piperidin-4-yl]-1H-benzotriazole-5-carboxylic acid,
1-[1-(3-isopropoxy-4-methoxy-benzyl)-piperidin-4-yl]-1H-benzotriazole-5-carboxylic acid,
1-[1-(3-allyloxy-4-methoxy-benzyl)-piperidin-4-yl]-1H-benzotriazole-5-carboxylic acid,
1-[1-(4-methoxy-3-prop-2-ynyloxy-benzyl)-piperidin-4-yl]-1H-benzotriazole-5-carboxylic acid,
1-[1-(3-butoxy-4-methoxy-benzyl)-piperidin-4-yl]-1H-benzotriazole-5-carboxylic acid,
1-[1-(3-isobutoxy-4-methoxy-benzyl)-piperidin-4-yl]-1H-benzotriazole-5-carboxylic acid,
1-[1-(3-cyclopentyloxy-4-methoxy-benzyl)-piperidin-4-yl]-1H-benzotriazole-5-carboxylic acid,
1-[1-(8-ethoxy-2,2-dimethyl-2H-chromen-6-ylmethyl)-piperidin-4-yl]-1H-benzotriazole-5-carboxylic acid,
1-[1-(3,5-diethoxy-benzyl)-piperidin-4-yl]-1H-benzotriazole-5-carboxylic acid,
1-[1-(3,5-diethoxy-4-fluoro-benzyl)-piperidin-4-yl]-1H-benzotriazole-5-carboxylic acid,
1-[1-(4-chloro-3,5-diethoxy-benzyl)-piperidin-4-yl]-1H-benzotriazole-5-carboxylic acid,
1-[1-(4-bromo-3,5-diethoxy-benzyl)-piperidin-4-yl]-1H-benzotriazole-5-carboxylic acid,
1-[1-(3,5-diethoxy-4-pyrrol-1-yl-benzyl)-piperidin-4-yl]-1H-benzotriazole-5-carboxylic acid,
1-[1-(3-ethoxy-4-methyl-benzyl)-piperidin-4-yl]-1,5-dihydro-imidazo[4,5-c]pyridin-4-one,
1-[1-(4-chloro-3-ethoxy-benzyl)-piperidin-4-yl]-1,5-dihydro-imidazo[4,5-c]pyridin-4-one,
1-[1-(3-ethoxy-4-methoxy-benzyl)-piperidin-4-yl]-1,5-dihydro-imidazo[4,5-c]pyridin-4-one,
1-[1-(3-ethoxy-4-isopropoxy-benzyl)-piperidin-4-yl]-1,5-dihydro-imidazo[4,5-c]pyridin-4-one,
1-[1-(3-ethoxy-4-isobutoxy-benzyl)-piperidin-4-yl]-1,5-dihydro-imidazo[4,5-c]pyridin-4-one,
1-{1-[3-ethoxy-4-(1-ethyl-propoxy)-benzyl]-piperidin-4-yl}-1,5-dihydro-imidazo[4,5-c]pyridin-4-one,
1-[1-(4-cyclopentyloxy-3-ethoxy-benzyl)-piperidin-4-yl]-1,5-dihydro-imidazo[4,5-c]pyridin-4-one,
1-[1-(4-benzyloxy-3-ethoxy-benzyl)-piperidin-4-yl]-1,5-dihydro-imidazo[4,5-c]pyridin-4-one,
1-[1-(4-difluoromethoxy-3-ethoxy-benzyl)-piperidin-4-yl]-1,5-dihydro-imidazo[4,5-c]pyridin-4-one,
1-[1-(3-isobutoxy-4-methoxy-benzyl)-piperidin-4-yl]-1,5-dihydro-imidazo[4,5-c]pyridin-4-one,
1-[1-(3-cyclopentyloxy-4-methoxy-benzyl)-piperidin-4-yl]-1,5-dihydro-imidazo[4,5-c]pyridin-4-one,
1-[1-(8-ethoxy-2,2-dimethyl-2H-chromen-6-ylmethyl)-piperidin-4-yl]-1,5-dihydro-imidazo[4,5-c]pyridin-4-one,
1-[1-(3,5-diethoxy-4-fluoro-benzyl)-piperidin-4-yl]-1,5-dihydro-imidazo[4,5-c]pyridin-4-one,
1-[1-(4-chloro-3,5-diethoxy-benzyl)-piperidin-4-yl]-1,5-dihydro-imidazo[4,5-c]pyridin-4-one,
1-[1-(4-bromo-3,5-diethoxy-benzyl)-piperidin-4-yl]-1,5-dihydro-imidazo[4,5-c]pyridin-4-one,
1-[1-(4-amino-3,5-diethoxy-benzyl)-piperidin-4-yl]-1,5-dihydro-imidazo[4,5-c]pyridin-4-one,
1-[1-(3,5-diethoxy-4-pyrrol-1-yl-benzyl)-piperidin-4-yl]-1,5-dihydro-imidazo[4,5-c]pyridin-4-one,
1-[1-(2,6-diethoxy-4'-fluoro-biphenyl-4-ylmethyl)-piperidin-4-yl]-1,5-dihydro-imidazo[4,5-c]pyridin-4-one,
2-[1-(3-ethoxy-4-methyl-benzyl)-piperidin-4-yl]-2,3-dihydro-isoindol-1-one,
2-[1-(3,5-diisopropoxy-benzyl)-piperidin-4-yl]-2,3-dihydro-isoindol-1-one,
2-[1-(3,5-diethoxy-4-fluoro-benzyl)-piperidin-4-yl]-2,3-dihydro-isoindol-1-one,
2-[1-(2-ethoxy-4'-fluoro-biphenyl-4-ylmethyl)-piperidin-4-yl]-2,3-dihydro-isoindol-1-one,
2-[1-(3,5-diisopropoxy-benzyl)-piperidin-4-yl]-5-methoxy-2,3-dihydro-isoindol-1-one,
2-[1-(3,5-diethoxy-4-fluoro-benzyl)-piperidin-4-yl]-5-methoxy-2,3-dihydro-isoindol-1-one, 2-[1-(3,5-diethoxy-4-pyrrol-1-yl-benzyl)-piperidin-4-yl]-5-methoxy-2,3-dihydro-isoindol-1-one,
2-[1-(2-ethoxy-4'-fluoro-biphenyl-4-ylmethyl)-piperidin-4-yl]-5-methoxy-2,3-dihydro-isoindol-1-one, and pharmaceutically acceptable salts thereof.

Especially preferred are the following compounds of formula I of the present invention:
1-[1-(4-chloro-3-ethoxy-benzyl)-piperidin-4-yl]-2-methyl-1H-benzoimidazole-5-carboxylic acid,
1-{1-[3-ethoxy-4-(1-ethyl-propoxy)-benzyl]-piperidin-4-yl}-2-methyl-1H-benzoimidazole-5-carboxylic acid,
1-[1-(8-ethoxy-2,2-dimethyl-2H-chromen-6-ylmethyl)-piperidin-4-yl]-2-methyl-1H-benzoimidazole-5-carboxylic acid,
1-[1-(3,5-diisopropoxy-benzyl)-piperidin-4-yl]-2-methyl-1H-benzoimidazole-5-carboxylic acid,
1-[1-(3,5-diethoxy-4-fluoro-benzyl)-piperidin-4-yl]-2-methyl-1H-benzoimidazole-5-carboxylic acid,
1-[1-(4-chloro-3,5-diethoxy-benzyl)-piperidin-4-yl]-2-methyl-1H-benzoimidazole-5-carboxylic acid,
1-[1-(4-bromo-3,5-diethoxy-benzyl)-piperidin-4-yl]-2-methyl-1H-benzoimidazole-5-carboxylic acid,
1-[1-(3,5-diethoxy-4-pyrrol-1-yl-benzyl)-piperidin-4-yl]-2-methyl-1H-benzoimidazole-5-carboxylic acid,
1-[1-(3,5-diethoxy-4-ethoxycarbonyl-benzyl)-piperidin-4-yl]-2-methyl-1H-benzoimidazole-5-carboxylic acid,
1-[1-(2,6-diethoxy-4'-fluoro-biphenyl-4-ylmethyl)-piperidin-4-yl]-2-methyl-1H-benzoimidazole-5-carboxylic acid,
1-[1-(4-chloro-3-ethoxy-benzyl)-piperidin-4-yl]-2-oxo-2,3-dihydro-1H-benzoimidazole-5-carboxylic acid,
1-[1-(4-difluoromethoxy-3-ethoxy-benzyl)-piperidin-4-yl]-2-oxo-2,3-dihydro-1H-benzoimidazole-5-carboxylic acid,
1-[1-(3,5-diisopropoxy-benzyl)-piperidin-4-yl]-2-oxo-2,3-dihydro-1H-benzoimidazole-5-carboxylic acid,
1-[1-(3,5-diethoxy-4-fluoro-benzyl)-piperidin-4-yl]-2-oxo-2,3-dihydro-1H-benzoimidazole-5-carboxylic acid,
1-[1-(4-chloro-3,5-diethoxy-benzyl)-piperidin-4-yl]-2-oxo-2,3-dihydro-1H-benzoimidazole-5-carboxylic acid,
1-[1-(4-bromo-3,5-diethoxy-benzyl)-piperidin-4-yl]-2-oxo-2,3-dihydro-1H-benzoimidazole-5-carboxylic acid,
1-[1-(3,5-diethoxy-4-pyrrol-1-yl-benzyl)-piperidin-4-yl]-2-oxo-2,3-dihydro-1H-benzoimidazole-5-carboxylic acid,
1-[1-(4-bromo-3,5-diethoxy-benzyl)-piperidin-4-yl]-3-oxo-1,2,3,4-tetrahydro-quinoxaline-6-carboxylic acid,
1-[1-(3,5-diethoxy-4-pyrrol-1-yl-benzyl)-piperidin-4-yl]-3-oxo-1,2,3,4-tetrahydro-quinoxaline-6-carboxylic acid,
1-[1-(2,6-diethoxy-4'-fluoro-biphenyl-4-ylmethyl)-piperidin-4-yl]-3-oxo-1,2,3,4-tetrahydro-quinoxaline-6-carboxylic acid,
1-[1-(3-ethoxy-4-fluoro-benzyl)-piperidin-4-yl]-1H-benzotriazole-5-carboxylic acid,
1-[1-(4-chloro-3-ethoxy-benzyl)-piperidin-4-yl]-1H-benzotriazole-5-carboxylic acid,
1-[1-(4-difluoromethoxy-3-ethoxy-benzyl)-piperidin-4-yl]-1H-benzotriazole-5-carboxylic acid,
1-[1-(3-butoxy-4-methoxy-benzyl)-piperidin-4-yl]-1H-benzotriazole-5-carboxylic acid,
1-[1-(3-isobutoxy-4-methoxy-benzyl)-piperidin-4-yl]-1H-benzotriazole-5-carboxylic acid,
1-[1-(3-cyclopentyloxy-4-methoxy-benzyl)-piperidin-4-yl]-1H-benzotriazole-5-carboxylic acid,
1-[1-(3,5-diethoxy-benzyl)-piperidin-4-yl]-1H-benzotriazole-5-carboxylic acid,
1-[1-(3,5-diethoxy-4-fluoro-benzyl)-piperidin-4-yl]-1H-benzotriazole-5-carboxylic acid,
1-[1-(4-chloro-3,5-diethoxy-benzyl)-piperidin-4-yl]-1H-benzotriazole-5-carboxylic acid,
1-[1-(4-bromo-3,5-diethoxy-benzyl)-piperidin-4-yl]-1H-benzotriazole-5-carboxylic acid,
1-[1-(3,5-diethoxy-4-pyrrol-1-yl-benzyl)-piperidin-4-yl]-1H-benzotriazole-5-carboxylic acid
1-[1-(4-bromo-3,5-diethoxy-benzyl)-piperidin-4-yl]-1,5-dihydro-imidazo[4,5-c]pyridin-4-one,
1-[1-(3,5-diethoxy-4-pyrrol-1-yl-benzyl)-piperidin-4-yl]-1,5-dihydro-imidazo[4,5-c]pyridin-4-one,
1-[1-(2,6-diethoxy-4'-fluoro-biphenyl-4-ylmethyl)-piperidin-4-yl]-1,5-dihydro-imidazo[4,5-c]pyridin-4-one,
2-[1-(3,5-diethoxy-4-pyrrol-1-yl-benzyl)-piperidin-4-yl]-5-methoxy-2,3-dihydro-isoindol-1-one, and pharmaceutically acceptable salts thereof.

Furthermore, the pharmaceutically acceptable salts of the compounds of formula I individually constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises a) reacting a piperidine of the formula

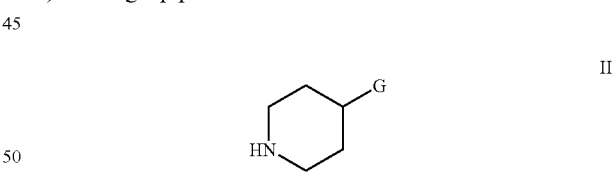

II wherein G is as defined herein before, with an aldehyde of the formula

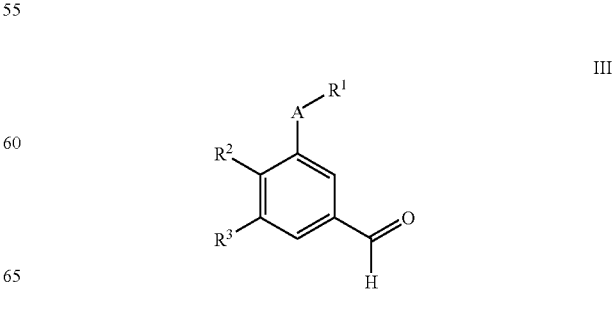

III wherein A and R¹ to R³ are as defined herein before, by employing a reducing agent to obtain a compound of the formula

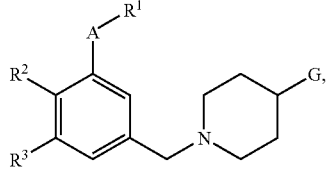

I and, if desired, converting the compound of formula I into a pharmaceutically acceptable salt; or, alternatively, b) alkylating a piperidine of the formula

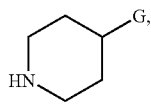

II wherein G is as defined herein before, with a compound of the formula

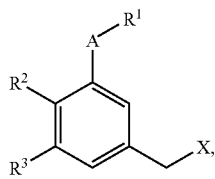

IV wherein A and R¹ to R³ are as defined herein before and X is a leaving group, under basic conditions to obtain a compound, or formula

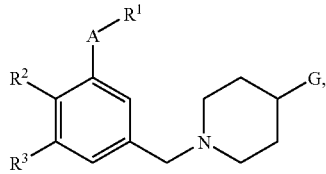

I and, if desired, converting the compound of formula I into a pharmaceutically acceptable salt; or, alternatively, c) reacting a compound of the general formula

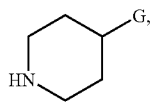

II wherein G is as defined herein before, with a compound of the formula

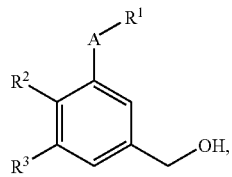

V wherein A and R¹ to R³ are as defined herein before, in the presence of a trialkylphosphine and a diazo-compound to obtain a compound of the formula

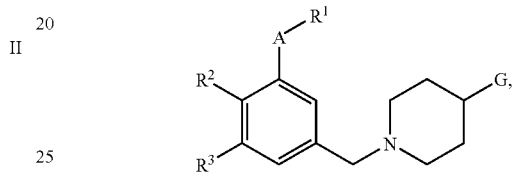

I and, if desired, converting the compound of formula I into a pharmaceutically acceptable salt.

The invention further relates to compounds of formula I as defined above, when manufactured according to a process as defined above.

Suitable reducing agents are preferably selected from the group consisting of pyridine-$BH_3$ complex, $NaBH(OAc)_3$ and $NaCNBH_3$. The reaction can be carried out under acidic conditions by using an acid such as acetic acid or formic acid or a Lewis acid (e.g., $Ti(iPrO)_4$, $ZnCl_2$) or under buffered conditions (e.g., in the presence of acetic acid and a tertiary amine like N-ethyldiisopropylamine or triethylamine) in a suitable solvent such as dichloromethane, dichloroethane, ethanol or isopropanol (or mixtures thereof) at ambient or elevated temperatures using conventional heating or heating by microwave irradiation.

Suitable leaving groups X are halides, mesylates or tosylates or alcohols containing another leaving group. Preferred leaving groups are selected from the group consisting of iodide, bromide, methanesulfonate and chloride.

Suitable trialkylphosphines are tributylphosphine and triphenylphosphine. Preferred diazo compounds are diethyl azodicarboxalate (DEAD), diisopropyl azodicarboxylate (DIAD) or di-tert-butyl azodicarboxylate.

As described above, the compounds of formula I of the present invention can be used as medicaments for the treatment and/or prevention of diseases which are associated with the modulation of SST receptors subtype 5.

Diseases which are associated with the modulation of SST receptors subtype 5 are such diseases as diabetes mellitus, particularly type II diabetes mellitus, impaired fasting glucose, impaired glucose tolerance, micro- and macrovascular diabetic complications, post transplantation diabetes mellitus in patients having type I diabetes mellitus, gestational diabetes, obesity, inflammatory bowel diseases such as Crohn's disease or ulcerative colitis, malabsorption, autoimmune diseases such as rheumatoid arthritis, osteoarthritis, psoriasis and other skin disorder, and immunodeficiencies. Microvascular diabetic complications include diabetic nephropathy and diabetic retinopathy, whereas macrovascular diabetes-associated complications lead to an increased risk for myocardial infarction, stroke and limb amputations.

The use as medicament for the treatment and/or prevention of diabetes mellitus, particularly type II diabetes mellitus, impaired fasting glucose or impaired glucose tolerance is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of SST receptors subtype 5.

In another embodiment, the invention relates to a method for the treatment and/or prevention of diseases which are associated with the modulation of SST receptors subtype 5, which method comprises administering a compound of formula I to a human or animal. The method for the treatment and/or prevention of diabetes mellitus, particularly type II diabetes mellitus, impaired fasting glucose or impaired glucose tolerance, is most preferred.

The invention further relates to the use of compounds as defined above for the treatment and/or prevention of diseases which are associated with the modulation of SST receptors subtype 5.

In addition, the invention relates to the use of compounds as defined above for the preparation of medicaments for the treatment and/or prevention of diseases which are associated with the modulation of SST receptors subtype 5. Preferred examples of such diseases are diabetes mellitus, particularly type II diabetes mellitus, impaired fasting glucose or impaired glucose tolerance.

The compounds of formula I can be manufactured by the methods given below, by the methods given in the examples or by analogous methods. Appropriate reaction conditions for the individual reaction steps are standard reactions and are known to a person skilled in the art. Starting materials are either commercially available or can be prepared by methods analogous to the methods given below, by methods described in references cited in the text or in the examples, or by methods known in the art.

The synthesis of compounds with the general structure I, particularly compounds according to formula Ia to If, are described in Schemes 1 to 6.

The synthesis of compounds according to formula Ia can be accomplished according to Scheme 1. Starting from appropriately substituted para-fluoro-benzoic acids like 1 nitration with potassium nitrate in conc. sulfuric acid, preferably at rt, provides nitro-derivatives 2 (Scheme 1, step a). Introduction of a suitable carboxylic acid protection group (see *Protective Groups in Organic Synthesis*, T. W. Greene and P. G. M. Wuts, 3$^{rd}$ Edition, 1999, Wiley-Interscience) such as an allyl ester gives then access to derivatives 3 (Scheme 1, step b). The esterification can be conducted using an allylhalide (e.g., allylbromide) in the presence of a base like potassium or sodium carbonate in a suitable solvent such as N,N-dimethylformamide (DMF), tetrahydrofuran (THF) or dioxane (or mixtures thereof) at ambient or elevated temperatures using conventional heating or heating by microwave irradiation. Appropriately protected nitro-fluoro-benzoic acids 3 undergo nucleophilic aromatic substitution ($SN_{Ar}$) with 4-amino-piperidines 4 in a solvent such as DMF and the presence of a suitable tertiary amine base (e.g., triethylamine, N-ethyldiisopropylamine) at preferably elevated temperatures to provide intermediates 5 (Scheme 1, step c). Reduction of the nitro group in compound 5 yielding the corresponding aniline derivative 6 can be effected in a manner which will be familiar to any person skilled in the art such as reduction with Zn in the presence of a mild acid at room temperature or under healing to reflux (Scheme 1, step d). Formation of the benzoimidazole derivative 7 can be achieved upon ring closure of aniline 6 with acetaldehyde in the presence of copper(II) acetate in a polar protic solvent such as ethanol and by heating to reflux. The alkyloxycarbonyl protecting group present in compounds 7 can be removed, using e.g., 48% aqueous hydrogen bromide or 37% aqueous hydrochloric acid as reagent preferably at elevated temperatures to cleave an ethyl carbamate or using trifluoroacetic acid or hydrochloric acid in a solvent like dichloromethane (DCM), dioxane or THF preferable at room temperature to remove a tert-butyloxycarbonyl (BOC)-protective group (see *Protective Groups in Organic Synthesis*, T. W. Greene and P. G. M. Wuts, 3$^{rd}$ Edition, 1999, Wiley-Interscience), yielding piperidines of formula 8 (Scheme 1, step f).

Scheme 1

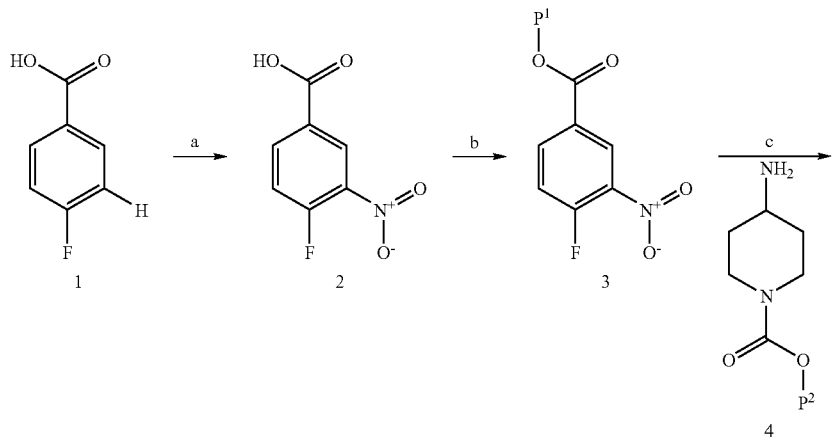

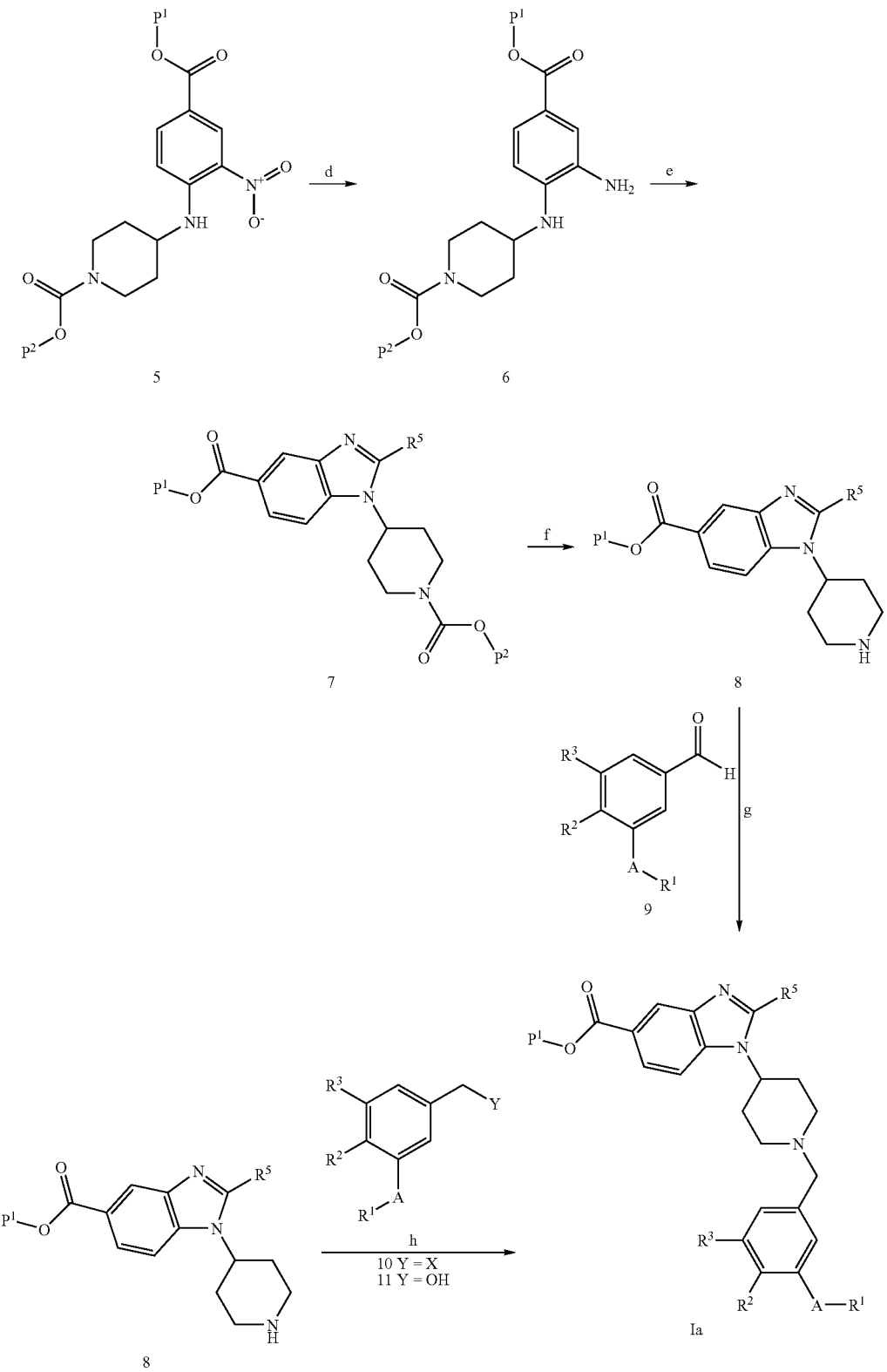
$P^1 = $ —CH$_2$CHCH$_2$
$P^2 = $ —CH$_2$CH$_3$ or —C(CH$_3$)$_3$

Reductive N-alkylation of free piperidines 8 with aldehydes 9 in the presence of a reducing agent such as pyridine-BH₃ complex, NaBH(OAc)₃ or NaCNBH₃ under acidic conditions (e.g., acetic acid, formic acid), by using a Lewis acid (e.g., Ti(iPrO)₄, ZnCl₂) or under buffered conditions, e.g., in the presence of acetic acid and a tertiary amine like N-ethyldiisopropylamine or triethylamine, in a suitable solvent such as dichloromethane (DCM), dichloroethane, ethanol or isopropanol (or mixtures thereof) at ambient or elevated temperatures using conventional heating or heating by microwave irradiation provides target structures Ia (Scheme 1, step g). In the coupling step piperidines of formula 8 may thereby be used either as salt, e.g., hydrochloride or hydrobromide, or as the corresponding free amine.

Target compounds of formula Ia might also be manufactured by direct alkylation of piperidines 8 with suitable halides, mesylates, tosylates or alcohols transformed into any other suitable leaving group X of general structure 10 in a solvent such as DMF, dichloromethane, dichloroethane or acetone at ambient or elevated temperatures using conventional heating or heating by microwave irradiation with the addition of a suitable tertiary amine base (e.g., triethylamine, N-ethyldiisopropylamine) or an inorganic base (e.g., Cs₂CO₃, K₂CO₃) or by analogous alkylation reactions (Scheme 1, step h). Alternatively target structures of formula Ia might be accessible by Mitsunobu reaction (D. L. Hughes, The Mitsunobu Reaction, in *Organic Reactions*, Volume 42, 1992, John Wiley & Sons, New York; pp. 335-656) applying alcohols 11 activated by a mixture of a phosphine like a trialkylphosphine such as tributylphosphine ((n-Bu)₃P), triphenylphosphine (Ph₃P) and the like and a diazo-compound like diethyl azodicarboxylate (DEAD), diisopropyl azodicarboxylate (DIAD) or di-tert-butyl azodicarboxylate and the like in a solvent commonly used for such transformations like THF, toluene, DCM and the like (Scheme 1, step h). There is no particular restriction on the nature of the solvent to be employed, provided that it has no adverse effect on the reaction or the reagents involved and that it can dissolve the reagents, at least to some extent. The reaction can take place over a wide range of temperatures ranging from ambient temperature to the reflux temperature of the solvent employed.

Target structures Ib are accessible via benzoimidazoles 12 which can be synthesized by ring closure reaction of aniline 6 with a suitably activated carbonyl source such as triphosgene in the presence of a tertiary amine base (e.g., triethylamine, N-ethyldiisopropylamine) in an inert solvent like toluene, DCM or the like (Scheme 2, step a). The reaction may be conducted at ambient or elevated temperature, whereby higher temperatures might be preferred. Removal of the alkyloxycarbonyl protecting group in 12 under strong acid catalysis (Scheme 2, step b) and reductive alkylation with aldehydes 9 or direct alkylation with intermediates 10 under conditions as previously discussed provides access to target compounds Ib (Scheme 2, step c). Alternatively, target compounds of formula Ib might also be manufactured by direct alkylation of piperidines 13 with suitable halides, mesylates, tosylates or alcohols transformed into any other suitable leaving group X of general structure 10 or by analogous alkylation reactions. Target structures of formula Ib might also be accessible by Mitsunobu reaction (D. L. Hughes, The Mitsunobu Reaction, in *Organic Reactions*, Volume 42, 1992, John Wiley & Sons, New York; pp. 335-656) applying alcohols 11 activated by a mixture of a phosphine like a trialkylphosphine such as tributylphosphine ((n-Bu)₃P), triphenylphosphine (Ph₃P) and the like and a diazo-compound like diethyl azodicarboxylate (DEAD), diisopropyl azodicarboxylate (DIAD) or di-tert-butyl azodicarboxylate and the like in a solvent commonly used for such transformations like THF, toluene, DCM and the like.

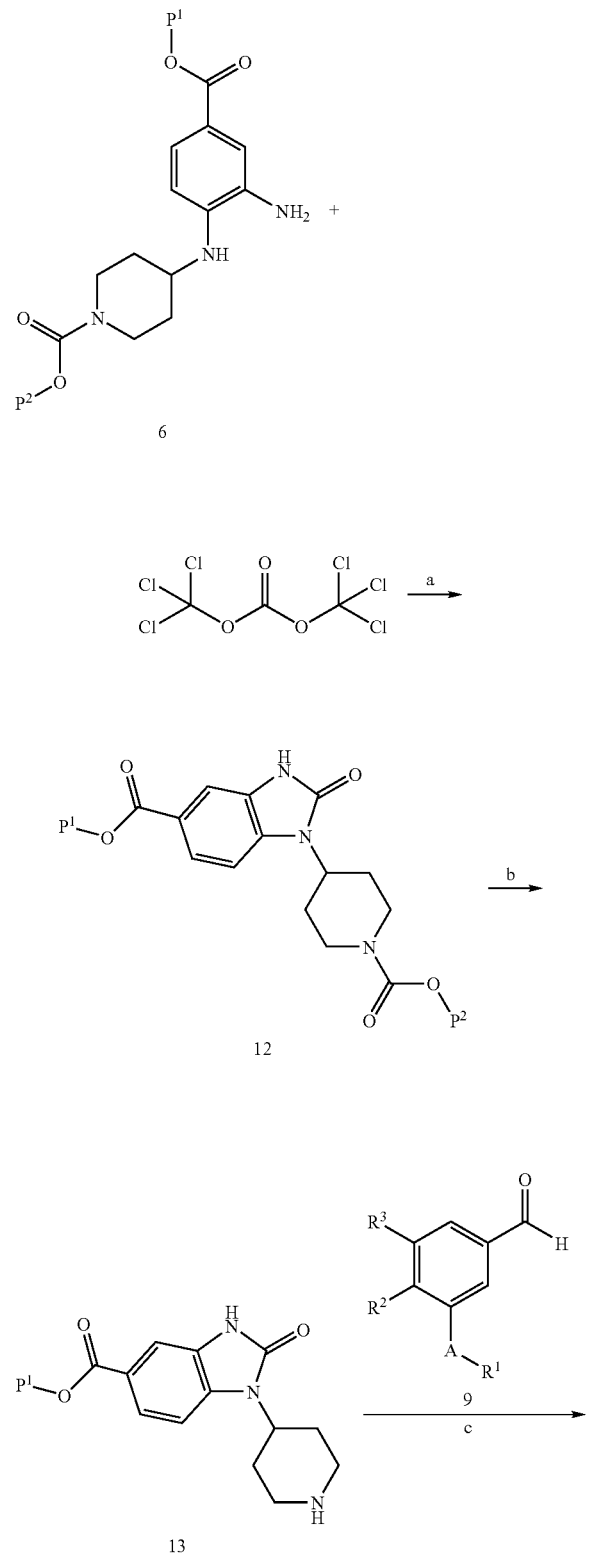

Scheme 2

-continued

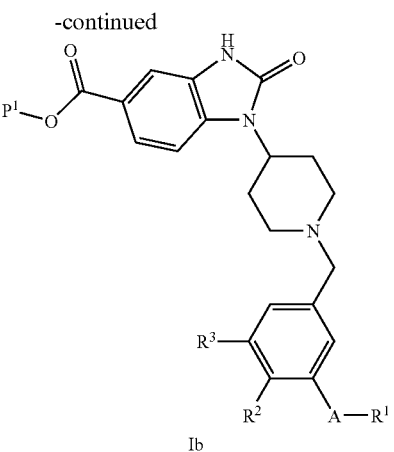

Ib

Target compounds of general structures Ic can be accomplished by amide bond formation of aniline 6 with a bromoacetyl halide, preferentially bromoacetyl chloride, in the presence of a tertiary amine base (e.g., triethylamine, N-ethyldiisopropylamine) in a inert solvent like DCM or toluene and the like at room or elevated temperature (Scheme 3, step a). Ring closure reaction of amide intermediate 14 to tetrahydro-quinoxaline 15 is then achieved by conventional heating or heating by microwave irradiation in the presence of a tertiary amine base such as N-ethyldiisopropylamine (Scheme 3, step b). Removal of the alkyloxycarbonyl protecting group in 15 under strong acid catalysis (Scheme 3, step c) and reductive alkylation with aldehydes 9 or direkt alkylation with intermediates 10 under conditions as previously discussed provides access to target compounds Ic (Scheme 3, step d). Target structures of formula Ic might also be accessible by Mitsunobu reaction (D. L. Hughes, The Mitsunobu Reaction, in *Organic Reactions*, Volume 42, 1992, John Wiley & Sons, New York; pp. 335-656) applying alcohols 11 activated by a mixture of a phosphine like a trialkylphosphine such as tributylphosphine ((n-Bu)$_3$P), triphenylphosphine (Ph$_3$P) and the like and a diazo-compound like diethyl azodicarboxylate (DEAD), diisopropyl azodicarboxylate (DIAD)) or di-tert-butyl azodicarboxylate and the like in a solvent commonly used for such transfomations like THF, toluene, DCM and the like.

Scheme 3

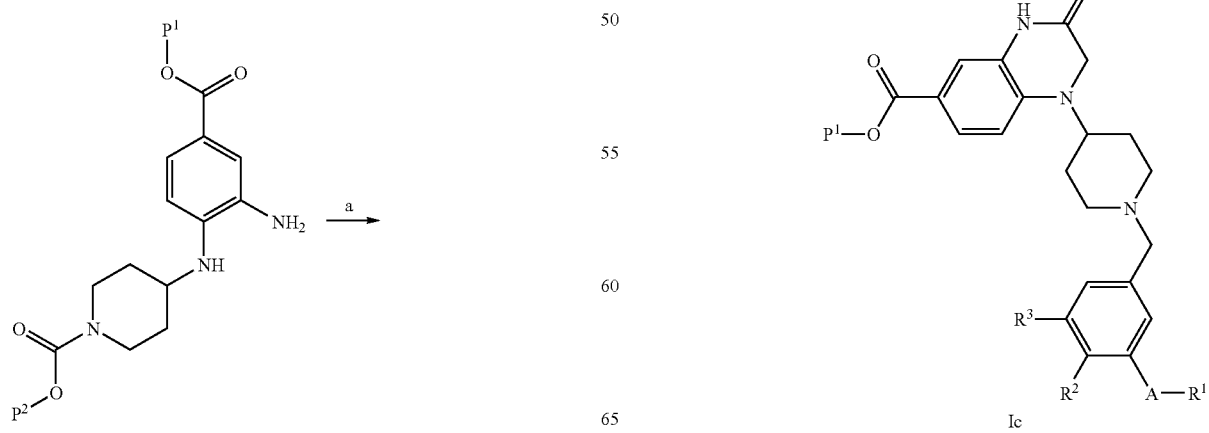

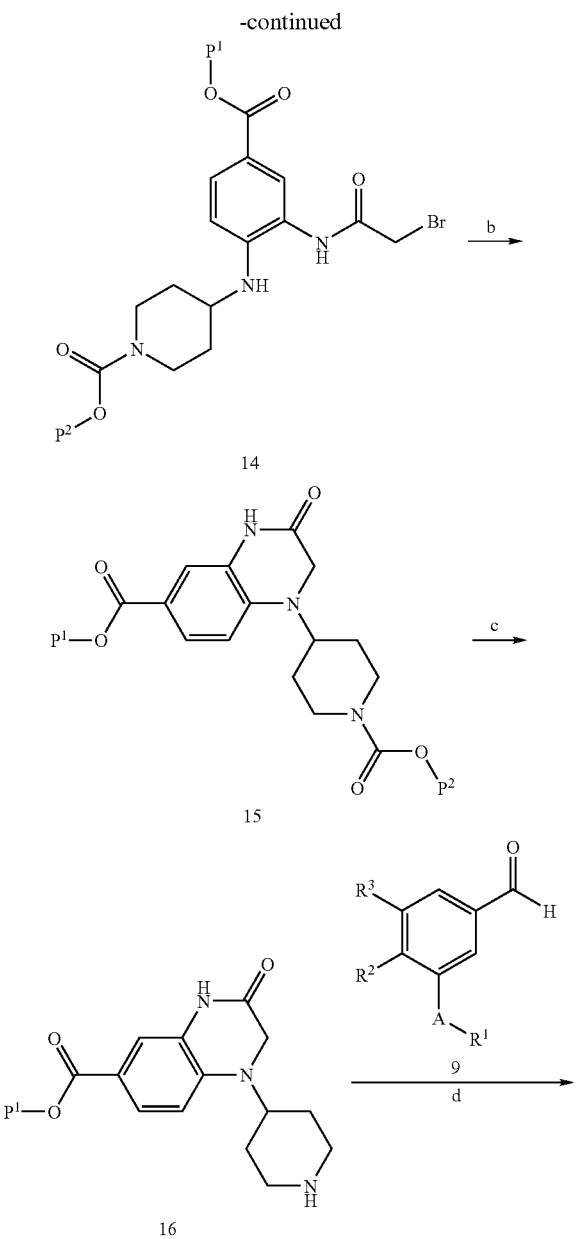

Target compounds of general structures Id can be prepared by diazotization of aniline 6 with sodium nitrite under strongly acidic reaction (e.g., hydrochloric acid) conditions (Scheme 4, step a). The in situ formed diazonium cation spontaneously ring closes to benzotriazole intermediate 17. Removal of the alkyloxycarbonyl protecting group in 17 under strong acid catalysis (Scheme 4, step b) and reductive alkylation with aldehydes 9 or direkt alkylation with intermediates 10 under conditions as previously discussed provides access to target compounds Id (Scheme 4, step c). Alternatively, target compounds of formula Id might also be manufactured by Mitsunobu reaction (D. L. Hughes, The Mitsunobu Reaction, in *Organic Reactions*, Volume 42, 1992, John Wiley & Sons, New York; pp. 335-656) with alcohols 11.

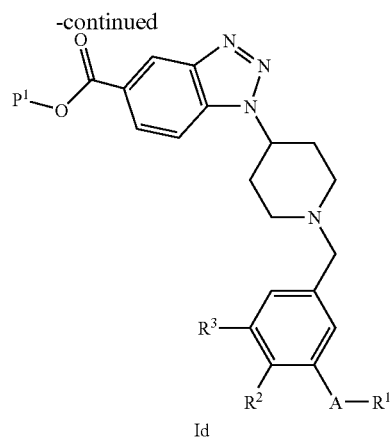

The synthesis of target structures Ie commences with nucleophilic aromatic substitution ($SN_{Ar}$) of appropriately substituted 4-chloro-3-nitro-pyridines 19 with 4-amino-piperidines 4 in a solvent such as DMF and the presence of a suitable tertiary amine base (e.g., triethylamine, N-ethyldiisopropylamine) at ambient or elevated temperatures (Scheme 5, step a). The nitro group of intermediates 20 can be reduced to the corresponding aniline derivative 21 by reduction with hydrogen under palladium on carbon catalysis at ambient or slightly elevated pressure using a low boiling alcohol such as methanol or ethanol (Scheme 5, step b). Formation of the imidazo[4,5-c]pyridine derivative 22 can be achieved by treatment of aniline 21 with triethyl orthoformate under acid catalysis (e.g., toluene-4-sulfonic acid) in an inert solvent such as toluene at ambient or elevated temperature (Scheme 5, step c). Preferentially the reaction is conducted at the reflux temperature of toluene.

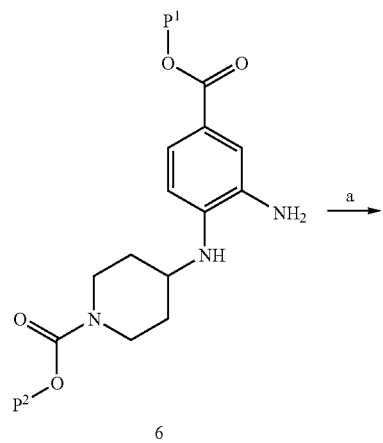

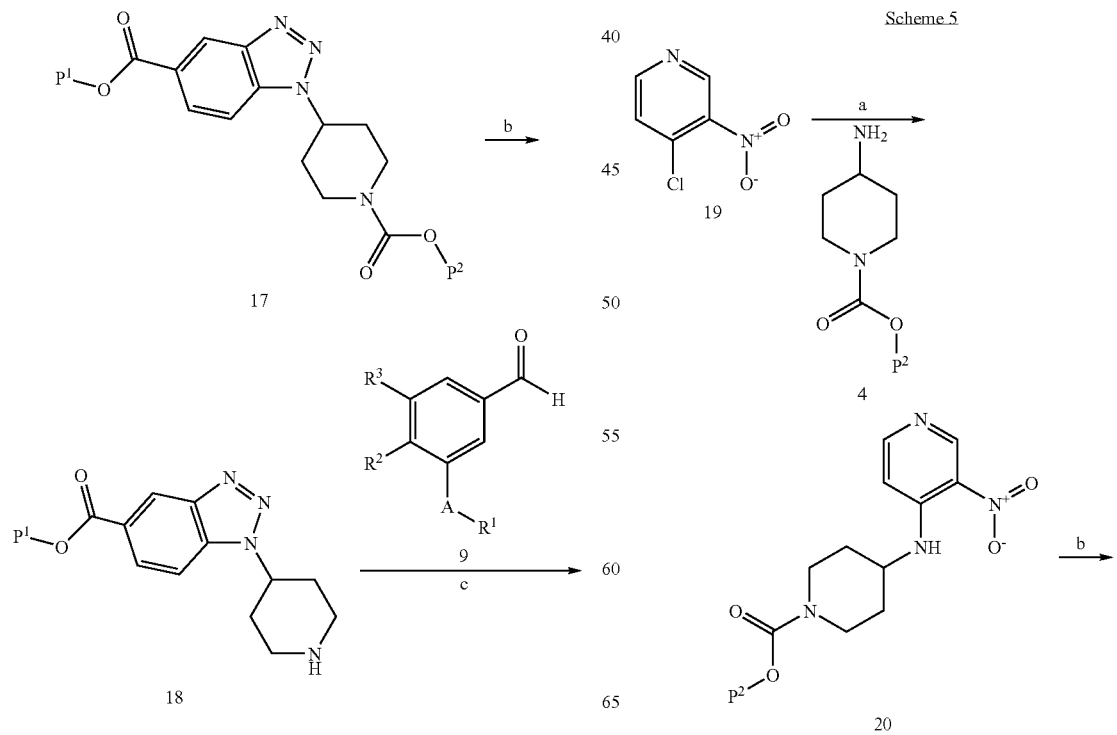

-continued

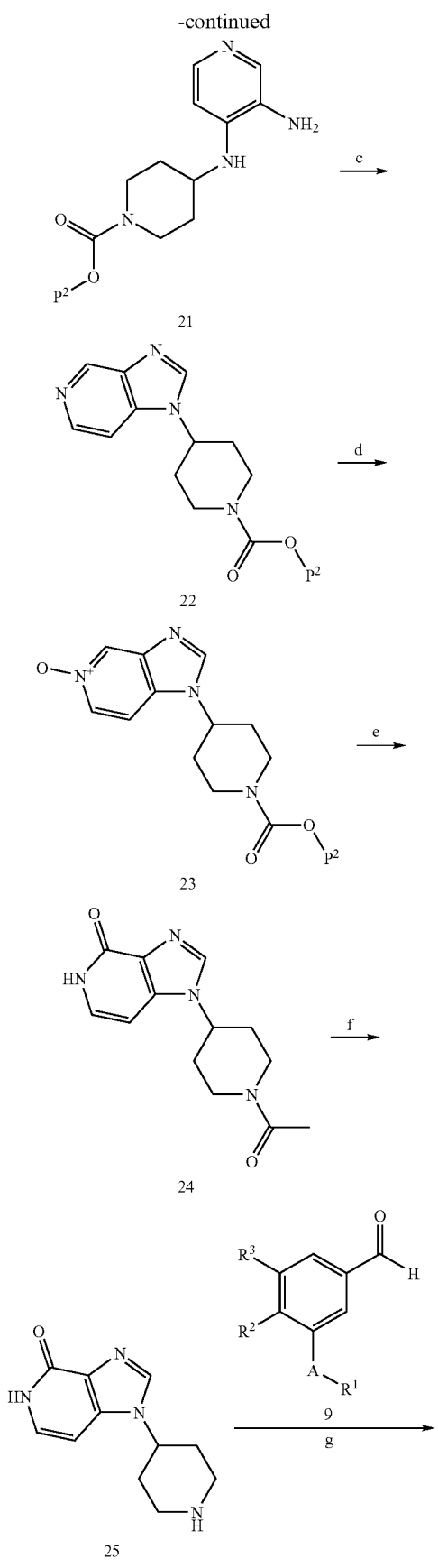

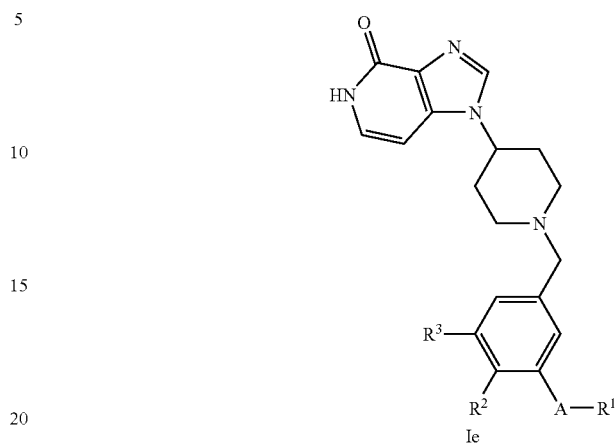

$P^2 = \text{—CH}_2\text{CH}_3 \text{ or } \text{—C(CH}_3)_3$

Oxidation of compound 22 to the pyridine oxide 23 is achieved by treatment with 3-chloro-perbenzoic acid at room or elevated temperature in a solvent such as DCM (Scheme 5, step d). Oxygen migration of the N-oxide 23 to imidazo[4,5-c]pyridinone 24 is induced by heating to reflux in the presence of acetic anhydride (Scheme 5, step e). Under the same reaction conditions the tert-butyloxycarbonyl (BOC)-protective group in 23 is exchanged to the corresponding acetamide which can be taken off under strong acid catalysis, preferably at elevated temperatures (Scheme 5, step f). Reductive alkylation of piperidine 25 with aldehydes 9 or direkt alkylation with intermediates 10 under conditions as previously discussed provides direct access to target compounds Ie (Scheme 5, step g). Alternatively, target compounds of formula Ie might also be manufactured by Mitsunobu reaction (D. L. Hughes, The Mitsunobu Reaction, in *Organic Reactions*, Volume 42, 1992, John Wiley & Sons, New York; pp. 335-656) with alcohols 11 as shown before.

Target compounds of general structures If can be prepared starting with radical bromination of the methyl group in 26 by, e. g., heating in CCl₄ in the presence of N-bromosuccinimide and dibenzoyl peroxide as initiator (Scheme 6, step a). Ensuing ring closure reaction of intermediate 27 with suitably protected 4-aminopiperidine 4 to 2,3-dihydro-isoindol-1-one 28 is then achieved by reacting them at ambient temperature or slight heating in the presence of a tertiary amine base such as triethylamine or N-ethyldiisopropylamine (Scheme 6, step b). Removal of the alkyloxycarbonyl protecting group in 28 under strong acid catalysis to give piperidine 29 (Scheme 6, step c) and reductive alkylation with aldehydes 9 or direkt alkylation with intermediates 10 under conditions as previously discussed provides access to target compounds If (Scheme 6, step d).

Scheme 6

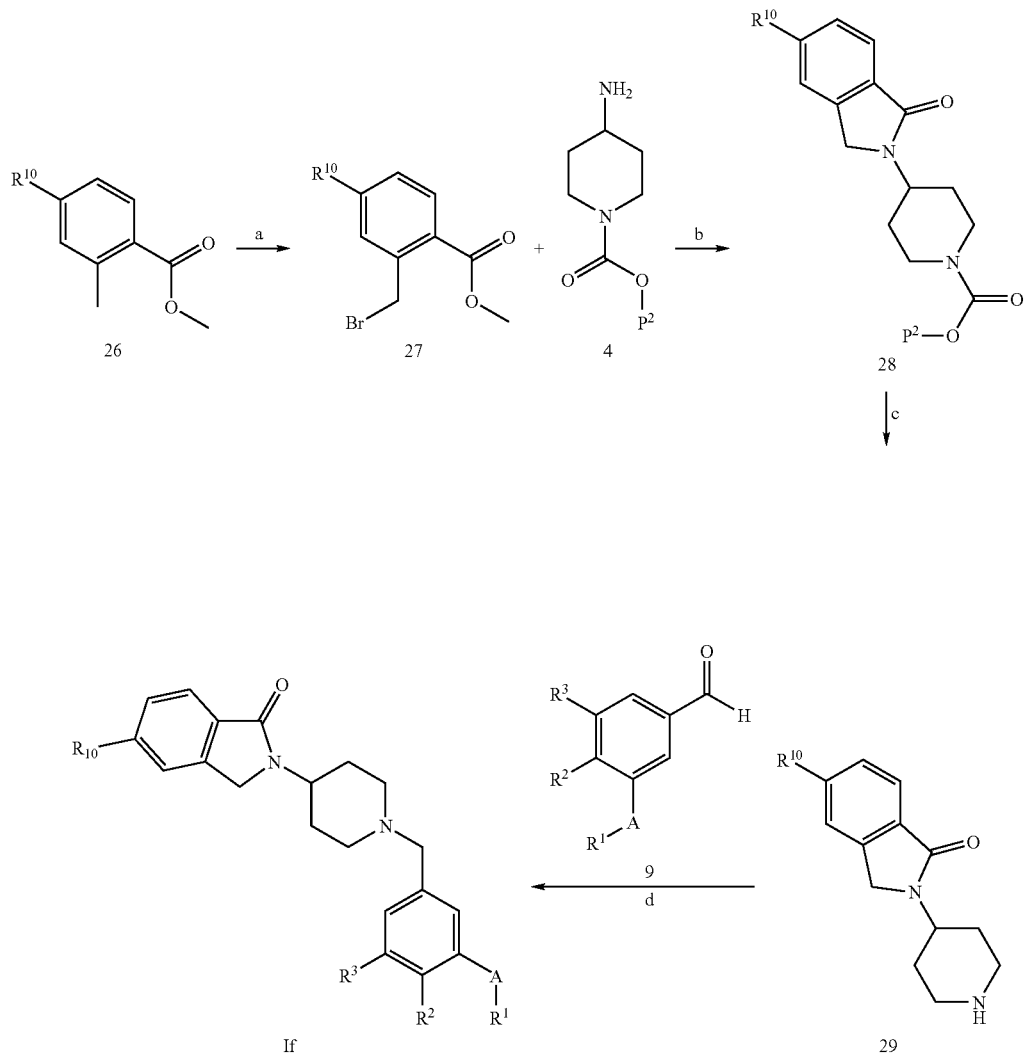

P² = —CH₂CH₃ or —C(CH₃)₃

Synthesis of Aldehyde Intermediates

The requisite aldehyde partners are either commercially available or can be derived by alkylation with alkyl halides, alkyl mesylates, alklyl tosylates or alcohols containing any other suitable leaving group in a polar solvent such as DMF (N,N-dimethylformamide) or acetone and a suitable base (e.g., $Cs_2CO_3$, $K_2CO_3$) at room temperature or elevated temperatures, by Mitsunobu reaction with alcohols activated by a mixture of triphenylphosphine and diethyl azadicarboxylate, or by analogous alkylation of the phenolic carboxylic esters or acids of formula 30 (Scheme 7, step a). Reduction of the esters of formula 31 by a suitable reducing agent (e.g., diisobutylaluminum hydride at low temperature or with $LiAlH_4$ at low, elevated or ambient temperature) in a solvent such as THF provides the corresponding benzylalcohols of formula 32 (Scheme 7, step b), which can then be oxidized to the aldehydes of formula 9, preferably with activated $MnO_2$ as oxidant in DCM (Scheme 7, step c).

Alternatively the introduction of the side-chain can be accomplished by direct alkylation (sequential for unsymmetrical compounds) of the phenolic benzaldehydes of formula 33 providing the desired compounds of formula 9 directly (Scheme 7, step d).

A further well-established route towards the synthesis of benzaldehydes of formula 9 consists in the reduction of the corresponding benzonitriles of formula 34 by a suitable reducing agent such as diisobutylaluminum hydride at low temperature in a non-protic polar solvent (e.g., THF; Scheme 7, step e).

Scheme 7

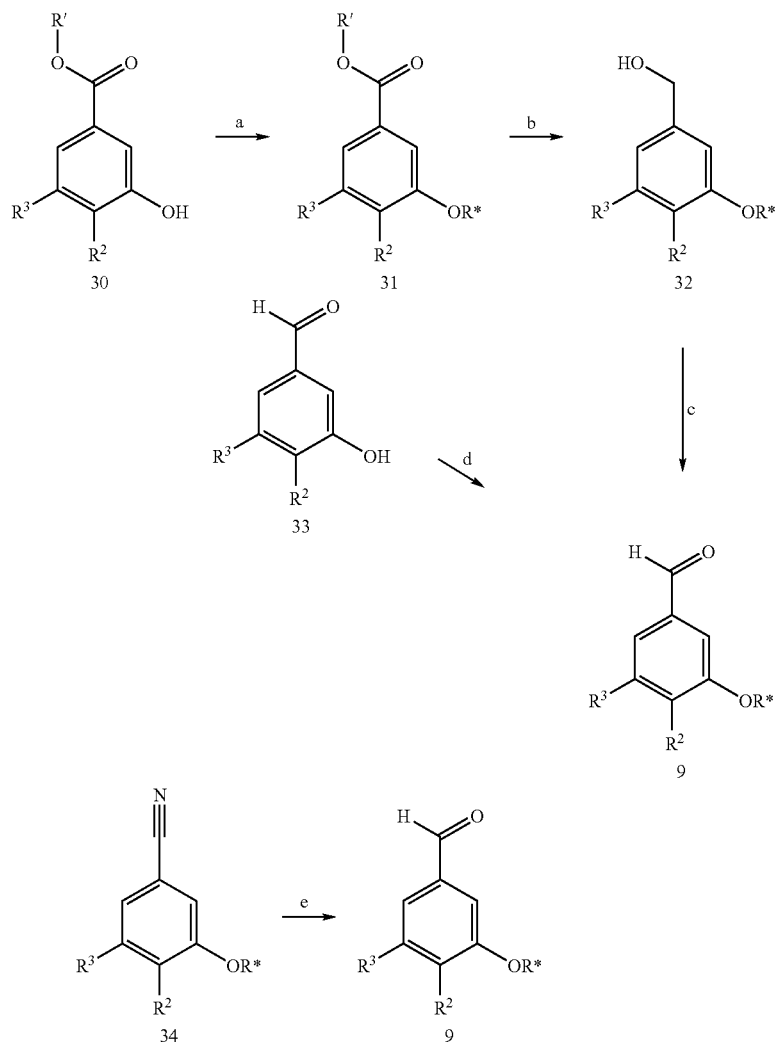

Additional syntheses of aldehydes of formula 11 are described in the examples.

As described hereinbefore, it has been found that the compounds of formula I possess pharmaceutical activity, in particular they are modulators of somatostatin receptor activity. More particularly, the compounds of the present invention have been found to be antagonists of the somatostatin receptor subtype 5 (SSTR5).

The following tests were carried out in order to determine the activity of the compounds of formula I.

A CHO cell line stably transfected with a plasmid encoding the human subtype 5 somatostatin receptor (GenBank accession number D16827) was obtained from Euroscreen. Cells were cultured and used for binding and functional assays.

Membranes of these cells were prepared by sonication in the presence of protease inhibitors and subsequent fractionating centrifugation. The protein concentration in the membrane preparation was determined using a commercial kit (BCA kit, Pierce, USA). Membranes were stored at −80° C. until use. After thawing membranes were diluted in assay buffer (50 mM Tris-HCl at pH 7.4, 5 mM $MgCl_2$ and 0.20% BSA) and subjected to dounce homogenization.

For binding studies, 0.1 mL membrane suspension, corresponding to approximately $6 \times 10^{-15}$ mol receptor, was incubated for 1 h at rt with 0.05 nM $^{125}$I-labeled tracer (11-Tyr somatostatin-14, Perkin-Elmer) and either test compounds in varying concentrations or, for the determination of non-specific binding, 0.001 mM non-labeled somatostatin-14. The incubation was stopped by filtration through GF/B glassfiber filters and washing with ice-cold wash buffer (50 mM Tris-HCl at pH 7.4). The bound radioactivity was measured after application of a scintillation cocktail (Microscint 40) and expressed as disintegrations per minute (dpm).

The receptor concentration was determined in a prior saturation experiment where a fixed, arbitrary amount of membranes was incubated with a concentration range of radio-labeled tracer. This allows estimating the total number of specific binding sites per amount of protein (i.e., $B_{max}$), typically between 1 and 5 pmol/mg.

The concentration of the test compound required to result in half maximal inhibition of binding of the radio-labeled tracer ($IC_{50}$) was estimated from a concentration-versus-dpm graph. The binding affinity ($K_i$) was calculated from the $IC_{50}$ by applying the Cheng-Prussoff equation for single binding sites.

For functional experiments, 50'000 cells were incubated in Krebs Ringer HEPES buffer (115 mM NaCl, 4.7 mM KCl, 2.56 mM $CaCl_2$, 1.2 mM $KH_2PO_4$, 1.2 mM $MgSO_4$, 20 mM $NaHCO_3$ and 16 mM HEPES, adjusted to pH 7.4) supplemented with 1 mM IBMX and 0.1% BSA, then stimulated with 0.004 mM forskolin. Simultaneously with forskolin, test compounds in varying concentrations were applied. Cells were then incubated for 20 minutes at 37° C. and 5% $CO_2$. Subsequently, cells were lysed and cAMP concentration measured using a fluorescence-based commercial kit according to the manufacturer (HitHunter cAMP, DiscoverX).

The concentration of the test compound to induce a half maximal effect (i.e., $EC_{50}$) as well as the efficacy as compared to 0.15 nM somatostatin-14 were determined from concentration-versus-fluorescence (arbitrary units) graphs. For the determination of potential antagonism, 0.15 nM somatostatin-14 was applied together with the test compounds and the concentration of the test compounds to half maximally reverse the effect of somatostatin-14 (i.e., $IC_{50}$) were deduced from concentration-versus-fluorescence graphs.

The compounds of the present invention exhibit in a radio-ligand replacement assay $K_i$ values of 0.1 nM to 10 μM, preferably $K_i$ values of 0.1 nM to 500 nM and more preferably 0.1 nM to 100 nM for the human subtype 5 somatostatin receptor. The following table shows measured values for selected compounds of the present invention.

|  | SSTR5 $K_i$ (nmol/l) |
| --- | --- |
| Example 13 | 0.108 |
| Example 51 | 0.653 |
| Example 84 | 0.005 |

The compounds of formula I and their pharmaceutically acceptable salts and esters can be used as medicaments, e.g., in the form of pharmaceutical preparations for enteral, parenteral or topical administration. They can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or infusion solutions, or topically, e.g., in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The present invention will be further explained by reference to the following illustrative examples. They are, however, not intended to limit its scope in any manner.

EXAMPLES

Abbreviations

Ar=argon, Celite=filtration aid, DMF=N,N-dimethylformamide, DMSO=dimethyl sulfoxide, EI=electron impact (ionization), HPLC=high performance liquid chromatography, Hyflo Super Cel®=filtration aid (Fluka), ISP=ion spray positive (mode), NMR=nuclear magnetic resonance, MPLC=medium pressure liquid chromatography, MS=mass spectrum, P=protecting group, R=any group, rt=room temperature, THF=tetrahydrofuran, X=halogen.

Example 1

1-[1-(3-Ethoxy-4-fluoro-benzyl)-piperidin-4-yl]-2-methyl-1H-benzoimidazole-5-carboxylic acid Step 1: 4-Fluoro-3-nitro-benzoic acid To a cold solution of 4-fluorobenzoic acid (50.0 g, 0.36 mol, 1.0 equiv) in concentrated $H_2SO_4$ (180 ml) was added portionwise potassium nitrate (39.7 g, 0.39 mol, 1.1 equiv). The reaction mixture was stirred overnight at rt and then poured on crushed ice (800 g) with constant stirring. The resulting mixture was kept overnight at rt, filtered and washed thoroughly with water, and finally dried by making an azeotrope with toluene to yield 59.5 g (90%) of the title compound as a light yellow solid. $^1$H NMR (400 MHz, DMSO): δ7.69-7.74 (m, 1H), 8.29-8.32 (m, 1H), 8.56 (d, J=7.2 Hz, 1H), 13.75 (br s, 1H).

Step 2: 4-Fluoro-3-nitro-benzoic acid allyl ester

To a mechanically stirred solution of 4-fluoro-3-nitro-benzoic acid (113.0 g, 0.61 mol, 1.0 equiv) in DMF (770 ml) was added portionwise potassium carbonate (168.7 g, 1.22 mol, 2.0 equiv). Allyl bromide (110.8 g, 0.92 mol, 1.5 equiv) was added to the reaction mixture and stirring continued at rt overnight. The reaction mixture was filtered, the filtrate poured into water (4 L), kept for 2 h and then extracted with ethyl acetate (3×1 L). The organic layer was washed with water, dried over Na$_2$SO$_4$ and concentrated by evaporation under reduced pressure. The residue was purified with silica column chromatography eluting with a gradient of hexane/ ethyl acetate (100:0→98:2) to obtain 114.1 g (83%) of the title compound. $^1$H NMR (400 MHz, DMSO): δ 4.86 (d, J=5.4 Hz, 2H), 5.30 (d, J=10.6 Hz, 1H), 5.43 (d, J=17.2 Hz, 1H), 6.01-6.10 (m, 1H), 7.73-7.78 (m, 1H), 8.34-8.37 (m, 1H), 8.60 (d, J=7.2 Hz, 1H).

Step 3: 4-(4-allyloxycarbonyl-2-nitro-phenylamino)-piperidine-1-carboxylic acid tert-butyl ester To a solution of 4-fluoro-3-nitro-benzoic acid allyl ester (84.3 g, 0.37 mol, 1.0 equiv) and 4-amino-piperidine-1-carboxylic acid tert-butyl ester (75.0 g, 0.37 mol, 1.0 equiv; commercially available) in DMF (500 mL) was added N-ethyldiisopropylamine (111.3 g, 0.86 mol, 2.3 equiv) and the reaction mixture heated at 70° C. for 6 h. The reaction mixture was cooled, poured into water (2 L) and the resulting mixture stirred at rt for 1 h. The precipitate was filtered, washed with water and hexane and finally dried over MgSO$_4$ to obtain 129.1 g (85%) of the title compound. $^1$H NMR (400 MHz, DMSO): δ 1.46 (s, 9H), 1.46-1.56 (m, 2H), 1.92-1.98 (m, 2H), 2.90-2.98 (m, 2H), 3.88-3.95 (m, 3H), 4.78 (d, J=5.2 Hz, 2H), 5.27 (d, J=10.4 Hz, 1H), 5.38 (d, J=17.3 Hz, 1H), 6.00-6.06 (m, 1H), 7.29 (d, J=9.2 Hz, 1H), 7.99 (dd, J=9.2 Hz, J=1.6 Hz, 1H), 8.24 (d, J=7.8 Hz, 1H), 8.64 (s, 1H).

Step 4: 4-(4-Allyloxycarbonyl-2-amino-phenylamino)-piperidine-1-carboxylic acid tert-butyl ester To a stirred suspension of 4-(4-allyloxycarbonyl-2-nitro-phenylamino)-piperidine-1-carboxylic acid tert-butyl ester (20.0 g, 49.33 mmol, 1.0 equiv) and Zn (23.22 g) 0.36 mol, 7.2 equiv) was added a sat. solution of NH$_4$Cl (7.91 g, 0.15 mol, 3.0 equiv) and the reaction mixture heated to reflux. After 45 min, the reaction was cooled, filtered through Celite and concentrated by evaporation under reduced pressure. The filtrate was diluted with water and extracted with dichloromethane (3×200 mL). The combined organic fractions were washed with water, dried over Na$_2$SO$_4$ and concentrated by evaporation under reduced pressure. The brownish solid material was further washed with a mixture of hexane/ethyl acetate (98:2) to yield 15.7 g (85%) of the title product. $^1$H NMR (400 MHz, DMSO): δ 1.24-1.33 (m, 2H), 1.46 (s, 9H), 1.90-1.94 (m, 2H), 2.88-2.94 (m, 2H), 3.53-3.55 (m, 1H), 3.88-3.95 (m, 2H), 4.68 (d, J=5.2 Hz, 2H), 4.79 (s, 2H), 5.01 (d, J=7.5, 2H), 5.23 (d, J=10.4 Hz, 1H), 5.34 (d, J=17.3 Hz, 1H), 6.00-6.06 (m, 1H), 6.54 (d, J=8.2 Hz, 1H), 7.21 (m, 2H).

Step 5: 1-(1-tert-Butoxycarbonyl-piperidin-4-yl)-2-methyl-1H-benzoimidazole-5-carboxylic acid allyl ester To a stirred solution of 4-(4-allyloxycarbonyl-2-amino-phenylamino)-piperidine-1-carboxylic acid tert-butyl ester (15.0 g, 39.95 mmol, 1.0 equiv) in ethanol (250 mL) were added copper(II) acetate (14.51 g, 79.90 mmol, 2.0 equiv) and acetaldehyde (44.1 mL, 0.20 mol, 5.0 equiv; 20% solution in water) and the reaction mixture heated to reflux for 36 h. The solvent was evaporated, the residue diluted with water and extracted with ethyl acetate. The combined organic fractions were washed with water and a sat. solution of NaCl, dried over Na$_2$SO$_4$, concentrated by evaporation under reduced pressure and purified with silica column chromatography eluting with a gradient of hexane/ethyl acetate (3:7→1:9) to obtain 7.2 g (45%) of the title compound as a brown solid. $^1$H NMR (400 MHz, DMSO): δ 1.46 (s, 9H), 1.88-1.91 (m, 2H), 2.14-2.20 (m, 2H), 2.63 (s, 3H), 2.97 (br s, 2H), 4.13-4.15 (m, 2H), 4.58 (t, J=11.5 Hz, 1H), 4.81 (d, J=4.6 Hz, 2H), 5.28 (d, J=10.4 Hz, 1H), 5.40 (d, J=17.2 Hz, 1H), 6.03-6.10 (m, 1H), 7.68 (d, J=8.3 Hz, 1H), 7.81 (d, J=8.3 Hz, 1H), 8.14 (s, 1H). MS (ISP): 400.3 [M+H]$^+$.

Step 6: 2-Methyl-1-piperidin-4-yl-1H-benzoimidazole-5-carboxylic acid allyl ester dihydrochloride (Intermediate A1)

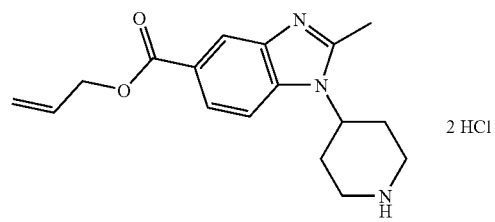

A solution of 1-(1-tert-butoxycarbonyl-piperidin-4-yl)-2-methyl-1H-benzoimidazole-5-carboxylic acid allyl ester (1.60 g, 4.01 mmol) in dioxane (20 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 300.4 [M+H]$^+$.

Step 7: 1-[1-(3-Ethoxy-4-fluoro-benzyl)-piperidin-4-yl]-2-methyl-1H-benzoimidazole-5-carboxylic acid To a solution of 2-methyl-1-piperidin-4-yl-1H-benzoimidazole-5-carboxylic acid allyl ester dihydrochloride (55.8 mg, 0.15 mmol, 1.0 equiv; intermediate A1) in methanol (0.8 mL) and water (0.4 mL) was added a solution of 10 M NaOH (60 µL), acetic acid (86 µL, 90.3 mg, 1.50 mmol, 10 equiv), 3-ethoxy-4-fluoro-benzaldehyde (30.3 mg, 0.18 mmol, 1.2 equiv; intermediate B1, vide infra) and sodium cyanoborohydride (47.1 mg, 0.75 mmol, 5.0 equiv), dissolved in ethanol (0.5 mL). The reaction mixture was stirred at 70° C. overnight. Removal of the solvent under reduced pressure and purification by preparative HPLC on reversed phase eluting with a gradient of acetonitrile/water provided 13.4 mg (22%) of the title compound. MS (ISP): 412.3 [M+H]$^+$.

The benzoimidazole, tetrahydro-quinoxaline, benzotriazole and dihydro-imidazo[4,5-c]pyridinone intermediates A2 to A5 were prepared as described below.

Synthesis of Benzoimidazole, Tetrahydro-quinoxaline, Benzotriazole and Dihydro-imidazo[4,5-c]pyridinone Intermediates A2 to A5 to be used in Table 1

Intermediate A2

2-Oxo-1-piperidin-4-yl-2,3-dihydro-1H-benzoimidazole-5-carboxylic acid allyl ester dihydrochloride

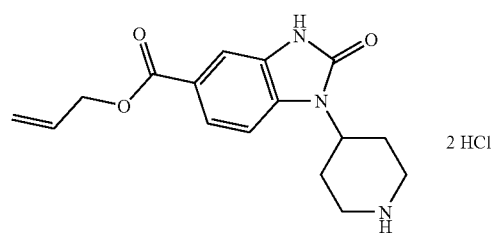

Step 1: 1-(1-tert-Butoxycarbonyl-piperidin-4-yl)-2-oxo-2,3-dihydro-1H-benzoimidazole-5-carboxylic acid allyl ester To a stirred solution of 4-(4-allyloxycarbonyl-2-aminophenylamino)-piperidine-1-carboxylic acid tert-butyl ester (20.0 g, 53.27 mmol, 1.0 equiv; example 1/step 4) in toluene (200 mL) and N-ethyldiisopropylamine (17.21 g, 133.17 mol, 2.5 equiv) was added a solution of triphosgene (18.97 g, 63.92 mmol, 1.2 equiv) in toluene (200 mL) and the reaction mixture stirred at 70° C. for 1.5 h. The solvent was evaporated, the residue diluted with water and extracted with ethyl acetate. The combined organic fractions were washed with water and a sat. solution of NaCl, dried over $Na_2SO_4$ and concentrated by evaporation under reduced pressure. The crude material was further washed with a mixture of hexane/ethyl acetate (95:5) to yield 15.5 g (73%) of the title product as wvhite solid. $^1$H NMR (400 MHz, DMSO): δ 1.43 (s, 9H), 1.72 (d, J=10.8, 2H), 2.17-2.23 (m, 2H), 2.88 (br s, 2H), 4.09 (d, J=8.6 Hz, 2H), 4.38 (t, J=12.2 Hz, 1H), 4.77 (d, J=5.3 Hz, 2H), 5.26 (d, J=10.4 Hz, 1H), 5.40 (dd, J=17.2 Hz, J=1.4 Hz, 1H), 5.99-6.09 (m, 1H), 7.35 (d, J=8.4 Hz, 1H), 7.53 (d, J=1.3 Hz, 1H), 7.69-7.71 (m, 1H), 11.17 (s, 1H). $^{13}$C-NMR (100 MHz, DMSO): δ 28.04, 28.43, 50.32, 64.78, 78.79, 108.13, 109.18, 117.70, 121.69, 121.71, 122.67, 128.20, 132.81, 133.39, 153.78, 153.82, 165.36. MS (ISP): 402.2 [M+H]$^+$.

Step 2: 2-Oxo-1-piperidin-4-yl-2,3-dihydro-1H-benzoimidazole-5-carboxylic acid allyl ester dihydrochloride A solution of 1-(1-tert-butoxycarbonyl-piperidin-4-yl)-2-oxo-2,3-dihydro-1H-benzoimidazole-5-carboxylic acid allyl ester (1.40 g, 3.49 mmol) in dioxane (20 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 302.1 [M+H]$^+$.

Intermediate A3

3-Oxo-1-piperidin-4-yl-1,2,3,4-tetrahydro-quinoxaline-6-carboxylic acid allyl ester dihydrochloride

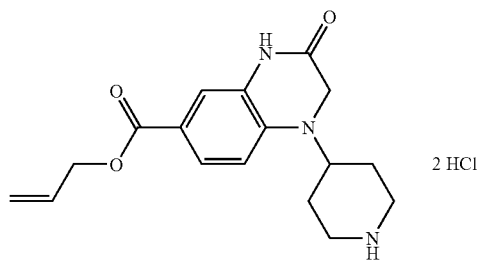

Step 1: 4-[4-Allyloxycarbonyl-2-(2-bromo-acetylamino)-phenylamino]-piperidine-1-carboxylic acid tert-butyl ester To a stirred solution of 4-(4-allyloxycarbonyl-2-aminophenylamino)-piperidine-1-carboxylic acid tert-butyl ester (25.0 g, 66.58 mmol, 1.0 equiv; example 1/step 4) in dichloromethane (250 mL) at 0° C. were slowly added triethylamine (16.84 g, 166.46 mol, 2.5 equiv) and bromoacetyl chloride (20.96 g, 133.17 mol, 2.0 equiv). After the addition was completed the cooling bath was removed and the reaction stirred for 2 h at rt. The reaction mixture was cooled again to 0° C., diluted with water and extracted with ethyl acetate. The combined organic fractions were washed with water, dried over $Na_2SO_4$, concentrated by evaporation under reduced pressure and purified with silica column chromatography eluting with hexane/ethyl acetate (65:35) to obtain 23.1 g (70%) of the title compound. $^1$H NMR (400 MHz, DMSO): δ 1.40 (s, 9H), 2.92 (br s, 2H), 3.62 (hr s, 1H), 4.03 (d, J=7.1, 2H), 4.30 (s, 2H), 4.72 (d, J=5.1, 2H), 5.24 (dd, J=10.5 Hz, J=1.0, 1H), 5.35 (dd, J=16.6 H, J=0.7, 1H), 5.50 (d, J=7.7 Hz, 1H), 5.98-6.05 (m, 1H), 6.82(d, J=8.8 Hz, 1H), 7.68 (dd, J=8.6 Hz, J=1.5 Hz, 1H), 7.73 (d, J=1.3 Hz, 1H), 9.43 (s, 1H).

Step 2: 1-(1-tert-Butoxycarbonyl-piperidin-4-yl)-3-oxo-1,2,3,4-tetrahydro-quinoxaline-6-carboxylic acid allyl ester A mixture of 4-[4-allyloxycarbonyl-2-(2-bromo-acetylamino)-phenylamino]-piperidine-1-carboxylic acid tert-butyl ester (23.0 g, 46.33 mmol, 1.0 equiv) and N-ethyldiisopropylamine (11.98 g, 92.67 mmol,2.0 equiv) in toluene (250 mL) was heated to reflux. After 8 h, the reaction mixture was cooled, washed with water and concentrated by evaporation under reduced pressure and purified with silica column chromatography eluting with dichloromethane/acetone (95:5) to obtain 10.0 g (52%) of the title compound as yellow solid. $^1$H NMR (400 MHz, DMSO): δ 1.41 (s, 9H), 1.65 (br s, 4H), 2.89 (s, 2H), 3.74 (s, 2H), 3.90 (br s, 1H), 4.05 (br s, 2H), 4.73 (d, J=5.1, 2H), 5.25 (d, J=10.4, 1H), 5.36 (dd, J=17.2 Hz, J=1.1 Hz, 1H), 5.98-6.05 (m, 1H), 6.95 (d, J=8.7 Hz, 1H), 7.44 (d, J=1.4 Hz, 1H), 7.53 (dd, J=17.2 Hz, J=1.1 Hz, 1H), 10.58 (s, 1H). $^{13}$C-NMR (100 MHz, DMSO): δ 26.87, 28.02, 45.15, 53.36, 64.35, 78.67, 110.81, 115.77, 117.36, 118.04, 125.21, 126.61, 132.95, 132.99, 138.63, 153.70, 164.94, 165.00. MS (ISP): 416.2 [M+H]$^+$.

Step 3: 3-Oxo-1-piperidin-4-yl-1,2,3,4-tetrahydro-quinoxaline-6-carboxylic acid allyl ester dihydrochloride A solution of 1-(1-tert-butoxycarbonyl-piperidin-4-yl)-3-oxo-1,2,3,4-tetrahydro-quinoxaline-6-carboxylic acid allyl ester (1.40 g, 3.37 mmol) in dioxane (20 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 316.1 [M+H]$^+$.

Intermediate A4

1-Piperidin-4-yl-1H-benzotriazole-5-carboxylic acid allyl ester dihydrochloride

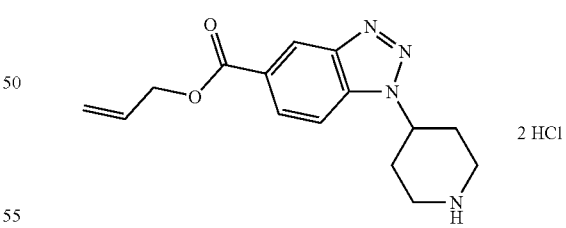

Step 1: 1-(1-tert-Butoxycarbonyl-piperidin-4-yl)-1H-benzotriazole-5-carboxylic acid allyl ester To a solution of 4-(4-allyloxycarbonyl-2-amino-phenylamino)-piperidine-1-carboxylic acid tert-butyl ester (50.0 g, 133.17 mmol, 1.0 equiv; example 1/step 4) in methanol (400 mL) was added conc. HCl (27.7 mL, 266.33 mmol, 2.0 equiv) and the reaction mixture stirred at 0° C. for 2 h. Another portion of conc. HCl (27.7 mL, 266.33 mmol, 2.0 equiv) was added and stirring was continued for an additional time period of 3 h. The reaction mixture was cooled to 0° C., diluted with water (25 mL), treated with a sat. solution of NaNO₂ (10.11 g, 146.48 mmol, 1.1 equiv) and stirred at rt for 30 min. The reaction mixture was cooled to 0° C., basified by addition of a sat. solution of NaHCO₃, concentrated by evaporation under reduced pressure and the aqueous phase extracted with ethyl acetate (3×150 mL). The organic solvents were to a large extent evaporated under reduced pressure and the aqueous layer was extracted with ethyl acetate (3×150 ml). The organic phase was washed with water, dried over Na₂SO₄ and evaporated under reduced pressure. The residue which was a mixture of the desired product and the de-boc analogue was treated with di-tert-butyl dicarbonate (29.06 g, 133.17 mmol, 1.0 equiv) and N-ethyl-diisopropylamine (20.65 g, 159.80 mmol, 1.2 equiv) in dichloromethane (200 mL). The solvent was evaporated under reduced pressure, water was added and the reaction mixture extracted with ethyl acetate (3×100 mL). The organic layer was washed with water, dried over Na₂SO₄ and evaporated under reduced pressure. The crude material was purified with silica column chromatography eluting with a gradient of hexane/ethyl acetate (9:1→4:1) to obtain 37.1 g (72%) of the title compound. ¹H NMR (400 MHz, DMSO): δ 1.44 (s, 9H), 2.02-2.16 (m, 4H), 3.05 (br s, 2H), 4.12-4.15 (m, 2H), 4.87 (d, J=5.2 Hz, 2H), 5.16-5.22 (m, 1H), 5.30 (d, J=10.7, 1H), 5.45 (dd, J=17.2 Hz, J=1.0 Hz, 1H), 6.06-6.13 (m, 1H), 8.08-8.15 (m, 2H), 8.68 (s, 1H). ¹³C-NMR (100 MHz, DMSO): δ 28.91, 32.21, 56.66, 66.25, 79.82, 112.04, 118.86, 122.44, 126.56, 128.09, 133.42, 135.42, 145.66, 154.72, 165.86. MS (ISP): 387.3 [M+H]⁺.

Step 2: 1-Piperidin-4-yl-1H-benzotriazole-5-carboxylic acid allyl ester dihydrochloride A solution of 1-(1-tert-butoxycarbonyl-piperidin-4-yl)-1H-benzotriazole-5-carboxylic acid allyl ester (1.40 g, 3.62 mmol) in dioxane (20 mL) and 4 M HCl in dioxane (20 mL) was stirred at rt for 2 h. The solvent was removed under reduced pressure and the crude product used in the consecutive step without further purification assuming quantitative deprotection and formation of the dihydrochloride salt. MS (ISP): 287.3 [M+H]⁺.

Intermediate A5

1-Piperidin-4-yl-1,5-dihydro-imidazo[4,5-c]pyridin-4-one dihydrochloride

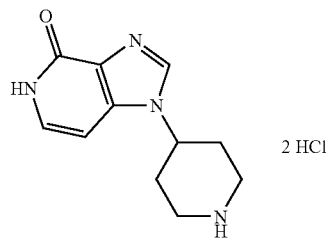

Step 1: 4-(3-Nitro-pyridin-4-ylamino)-piperidine-1-carboxylic acid tert-butyl ester To a solution of 4-chloro-3-nitro-pyridine (25.0 g, 157.69 mmol, 1.0 equiv; commercially available) and triethylamine (19.15 g, 189.23 mol, 1.2 equiv) in anhydrous DMF (100 mL) was added 4-amino-piperidine-1-carboxylic acid tert-butyl ester (31.58 g, 157.69 mmol, 1.0 equiv; commercially available), dissolved in anhydrous DMF (30 mL), and the reaction mixture stirred at rt for 15 h. The reaction mixture was poured into ice-cold water (1 L) and stirred for 2 h, allowed to settle for another 2 h and then filtered. The orange solid was washed with water and air-dried. The crude material was crystallized from ethyl acetate to obtain 43.7 g (86%) of the title compound. ¹H NMR (400 MHz, DMSO): δ 1.41 (s, 9H), 1.48-1.56 (m, 2H), 1.88-1.90 (m, 2H), 2.93 (br s, 2H), 3.90-3.93 (m, 3H), 7.14 (d, J=6.3 HZ, 1H), 8.03 (d, J=7.9 Hz, 1H), 8.27 (s, J=6.2 Hz, 1H), 9.03 (s, 1H).

Step 2: 4-(3-Amino-pyridin-4-ylamino)-piperidine-1-carboxylic acid tert-butyl ester To a solution of 4-(3-nitro-pyridin-4-ylamino)-piperidine-1-carboxylic acid tert-butyl ester (25.0 g, 77.55 mmol, 1.0 equiv) in ethanol (375 mL) was added palladium on activated charcoal 10% (2.5 g, 2.35 mmol, 0.03 equiv) and the reaction put under hydrogen (50 Psi) in a Parr shaker for 16 h. The reaction mixture was filtered through Celite and the filtrate evaporated under reduced pressure. The residue was triturated with diethyl ether, the organic layer decanted and the solid material dried under reduced pressure to yield 18.4 g (81%) of the title compound. ¹H NMR (400 MHz, DMSO): δ 1.25-1.27 (m, 2H), 1.40 (s, 9H), 1.88-1.91 (m, 2H), 2.90 (br s, 2H), 3.49 (br s, 1H), 3.89 (br s, 2H), 4.57 (s, 2H), 5.05 (br s, 1H), 6.42 (d, J=4.3 Hz, 1H), 7.56 (d, J=4.3 Hz, 1H), 7.63 (s, 1H). MS (ISP): 293.4 [M+H]⁺.

Step 3: 4-Imidazo[4,5-c]pyridin-1-yl-piperidine-1-carboxylic acid tert-butyl ester To a solution of 4-(3-amino-pyridin-4-ylamino)-piperidine-1-carboxylic acid tert-butyl ester (10.0 g, 34.20 mmol, 1.0 equiv) and triethyl orthoformate (10.14 g, 68.40 mmol, 2.0 equiv) in anhydrous toluene (70 mL) was added toluene-4-sulfonic acid (0.59 g, 3.42 mmol, 0.1 equiv) and the reaction mixture heated to reflux for 16 h. The solvent was removed by evaporation under reduced pressure and the residue triturated with diethyl ether. The preciptate was filtered off, washed with diethyl ether and dried under reduced pressure to yield 7.6 g (73%) of the title compound. ¹H NMR (400 MHz, DMSO): δ 1.43 (s, 9H), 1.92-2.04 (m, 4H), 2.95 (br s, 2H), 4.13 (br s, 2H), 4.64 (t, J=3.8 Hz, 1H), 7.75 (d, J=5.5 Hz, 1H), 8.34 (d, J=5.5 Hz, 1H), 8.55 (s, 1H), 8.95 (s, 1H). MS (ISP): 303.2 [M+H]¹.

Step 4: 4-(5-Oxy-imidazo[4,5-c]pyridin-1-yl)-piperidine-1-carboxylic acid tert-butyl ester To a solution of 4-imidazo[4,5-c]pyridin-1-yl-piperidine-1-carboxylic acid tert-butyl ester (10.0 g, 33.07 mmol, 1.0 equiv) in anhydrous dichloromethane (100 mL) was added at 10° C. 3-chloro-perbenzoic acid (7.41 g, 33.07 mmol, 1.0 equiv; 77% purity) and the reaction mixture stirred at rt for 18 h. The solvent was removed under reduced pressure and the residue purified with neutral alumina column chromatography eluting with a gradient of dichloromethane/methanol (95:5→70:30) to obtain 8.2 g (78%) of the title compound. ¹H NMR (400 MHz, DMSO): δ 1.43 (s, 9H), 1.86-1.95 (m, 2H), 2.02-2.05 (m, 2H), 2.92 (br s, 2H), 4.12 (br s, 2H), 4.63 (t, J=11.7 Hz, 1H), 7.83 (d, J=7.0 Hz, 1H), 8.11 (d, J=5.9 Hz, 1H), 8.62 (s, 1H), 8.69 (s, 1H). MS (ISP): 319.2 [M+H]⁺.

Step 5: 1-(1-Acetyl-piperidin-4-yl)-1,5-dihydro-imidazo[4,5-c]pyridin-4-one

A solution of 4-(5-oxy-imidazo[4,5-c]pyridin-1-yl)-piperidine-1-carboxylic acid tert-butyl ester (10.0 g, 31.41 mmol, 1.0 equiv) in anhydrous acetic anhydride (100 mL) was heated to reflux for 18 h. The solvent was removed under reduced pressure and the residue purified with neutral alumina column chromatography eluting with dichloromethane/methanol (97:3) to obtain 4.7 g (57%) of the title compound. ¹H NMR (400 MHz, DMSO): δ 1.79-1.82 (m, 1H), 1.91-1.99

(m, 3H), 2.05 (s, 3H), 2.67 (t, J=11.8, 1H), 3.16-3.24 (m, 1H), 3.95-3.98 (m, 1H), 4.51-4.57 (m, 2H), 6.68 (d, J=7.0 Hz, 1H), 7.16-7.19 (m, 1H), 8.12 (s, 1H), 11.17 (s, 1H). MS (ISP): 261.2 [M+H]+.

Step 6: 1-Piperidin-4-yl-1,5-dihydro-imidazo[4,5-c]pyridin-4-one dihydrochloride To a solution of 1-(1-acetyl-piperidin-4-yl)-1,5-dihydro-imidazo[4,5-c]pyridin-4-one (6.00 g, 23.05 mmol) in ethanol (48 mL) was added conc. HCl (24 mL) and the reaction mixture heated to reflux for 16 h. The solvent was removed under reduced pressure and the crude product used in the consecutive step without further purification assuming quantitative deprotection and formation of the dihydrochloride salt. MS (ISP): 219.2 [M+H]+.

The aldehyde intermediates B1 to B20 were prepared following literature precedents or in analogy to literature precedents or as described below.

Synthesis of Aldehyde Intermediates B1 to B20 to be used in Table 1 and Table 2

Intermediate B1

3-Ethoxy-4-fluoro-benzaldehyde

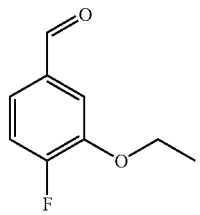

The title compound was prepared according to the procedure described for the synthesis of 4-chloro-3-ethoxy-benzaldehyde (intermediate B2, vide infra) starting from 4-fluoro-3-hydroxy-benzoic acid in 73% overall yield after purification by flash column chromatography on silica eluting with hexane/ethyl acetate (10:1). 1H NMR (300 MHz, DMSO): δ 1.32 (t, J=7.0 Hz, 3H), 4.12 (q, J=7.0 Hz, 2H), 7.34-7.41 (m, 1H), 7.47-7.56 (m, 2H), 9.87 (s, 1H). MS (ISP): 186.1 [M+NH4]+.

Intermediate B2

4-Chloro-3-ethoxy-benzaldehyde [CAS RN 85259-46-71]

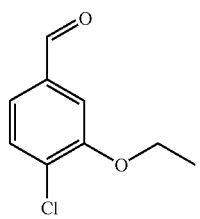

To a solution of 4-chloro-3-hydroxy-benzoic acid (3.0 g, 17.4 mmol, 1.0 equiv) in DMF (15 mL) was added $K_2CO_3$ (4.81 g, 34.8 mmol, 2.0 equiv) and ethyl iodide (4.03 mL, 5.97 g, 38.2 mmol, 2.2 equiv). The reaction mixture was stirred for 6 h at rt, diluted with water (20 mL) and extracted with ethyl acetate (3×50 mL). The organic phase was dried over $Na_2SO_4$ and concentrated to afford 3.6 g (91%) of 4-chloro-3-ethoxy-benzoic acid ethyl ester. The crude ester was then dissolved in THF (20 mL) and cooled to −78° C. under Ar. A solution of diisobutylaluminum hydride (95 ml, 95.0 mmol, 6.0 equiv; 1.0 M solution in THF) was slowly added over a time period of 15 min, the cooling bath removed after completion of addition and the reaction allowed to reach 0° C. After stirring for 1 h, the reaction was cooled to −78° C. and the excess of hydride quenched by cautious addition of a solution of 1 M HCl (10 mL). The mixture was warmed up to rt, the organic phase separated and the aqueous layer extracted with ethyl acetate (3×100 mL). The combined organic phases were dried over $Na_2SO_4$ and concentrated by evaporation under reduced pressure providing 2.94 g (100%) of 4-chloro-3-ethoxy-benzyl alcohol. The crude alcohol (2.94 g, 15.75 mmol, 1.0 equiv) was dissolved in dichloromethane (15 mL) and activated $MnO_2$ (5.48 g, 63.0 mmol, 4.0 equiv) was added. The reaction mixture was stirred for 16 h, after which time the reaction was filtered through Hyflo Super Cel and concentrated. The residue was purified by flash column chromatography on silica eluting with heptane/ethyl acetate (4:1) to yield 1.51 g (52%) of the title compound. 1H NMR (300 MHz, CDCl3): δ 1.51 (t, J=7.1 Hz, 3H), 4.19 (q, J=7.1 Hz, 2H), 7.37-7.42 (m, 2H), 7.55 (d, J=9.0 Hz, 1H), 9.94 (s, 1H).

Intermediate B3

3-Ethoxy-4-(1-ethyl-propoxy)-benzaldehyde

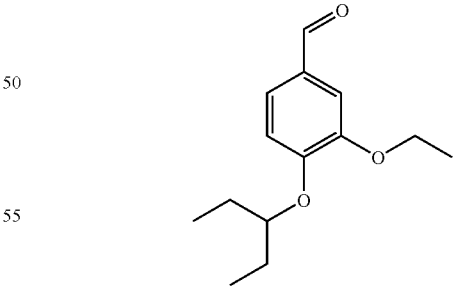

The title compound was prepared analogously to 3-ethoxy-4-methyl-benzaldehyde (intermediate B19, vide infra) by reaction of 3-ethoxy-4-hydroxy-benzaldehyde with 3-bromo-pentane in DMF using $K_2CO_3$ as base. MS (ISP): 237.1 [M+H]+.

Intermediate B4

3-(2-Fluoro-ethoxy)-4-methoxy-benzaldehyde

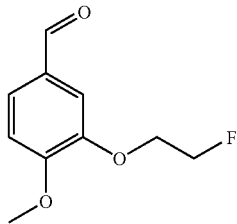

To a solution of 3-hydroxy-4-methoxy-benzaldehyde (100 g, 66.0 mmol, 1.0 equiv; commercially available) in anhydrous DMF (40 mL) was added $K_2CO_3$ (13.6 g, 99.0 mmol, 1.5 equiv) and 1-bromo-2-fluoro-ethane (9.2 mg, 72.0 mmol, 1.1 equiv) and the mixture stirred at rt for 48 h. The $K_2CO_3$ was removed by filtration and the organic phase concentrated under reduced pressure. To the residue was added a sat. solution of NaCl (100 mL) and the solution extracted with ethyl acetate (3×100 mL). The combined organic phases were dried over $MgSO_4$ and the product crystallized from a mixture of isopropanol/diethyl ether to yield 12.69 g (97%) of the title compound. $^1$H NMR (300 MHz, DMSO): δ 3.89 (s, 3H), 4.24-4.27 (m, 1H), 4.34-4.37 (m, 1H), 4.67-4.70 (m, 1H), 4.83-4.86 (m, 1H), 7.20 (d, J=8.4 Hz, 1H), 7.43 (d, J=1.9 Hz, 1H), 7.59 (dd, J=8.4 Hz, J=1.9 Hz, 1H), 9.84 (s, 1H). MS (ISP): 198.6 $[M+H]^+$.

Intermediate B5

3-Isobutoxy-4-methoxy-benzaldehyde [CAS RN 57724-26-21]

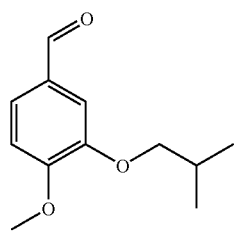

The title compound was prepared by reaction of isovanillin with 1-bromo-2-methyl propane as described in WO 04/000 806 A1 (Elbion AG).

Intermediate B6

8-Ethoxy-2,2-dimethyl-2H-chromene-6-carbaldehyde [CAS RN 210404-30-9]

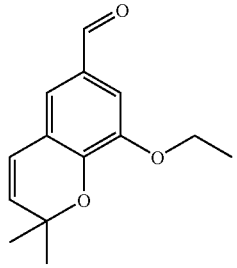

The title compound was prepared according to WO 01/083 476 A1 (Hoffmann-La Roche AG).

Intermediate B7

3,5-Diethoxy-benzaldehyde [CAS RN 120355-79-5]

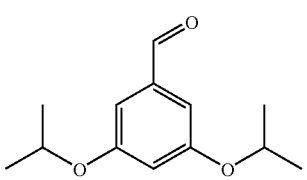

The title compound was prepared analogously to 3-ethoxy-4-methyl-benzaldehyde (intermediate B19, vide infra) by reaction of 3,5-dihydroxybenzaldehyde with ethyl iodide in DMF using $K_2CO_3$ as base.

Intermediate B8

3,5-Diisopropoxy-benzaldehyde [CAS RN 94169-64-9]

To a solution of 3,5-dihydroxy-benzaldehyde (5.0 g, 36.20 mmol, 1.0 equiv) in anhydrous DMF (30 mL) was added $K_2CO_3$ (15.0 g, 108.60 mmol, 3.0 equiv) and 2-bromo-propane (13.36 g, 10.20 mL, 108.60 mmol, 3.0 equiv) and the mixture stirred at 100° C. for 18 h. The $K_2CO_3$ was removed by filtration and the organic phase concentrated under reduced pressure. To the residue was added a sat. solution of NaCl (100 mL) and the solution extracted with ethyl acetate (3×100 mL). The combined organic phases were dried over MgSO₄ and the product purified by silica column chromatography using a MPLC system (CombiFlash Companion, Isco Inc.) eluting with a gradient of heptane/ethyl acetate affording 6.64 g (83%) of the title compound and 0.59 g (9%) of 3-hydroxy-5-isopropoxy-benzaldehyde. ¹H NMR (300 MHz, CDCl₃): δ 1.35 (d, J=6.1 Hz, 12H), 4.59 (hept, J=6.1 Hz, 2H), 6.66-6.68 (m, 1H), 6.96-6.97 (m, 2H), 9.88 (s, 1H). MS (ISP): 223.1 [M+H]⁺.

Intermediate B9

2,6-Diethoxy-4-formyl-benzoic acid ethyl ester
[CAS RN 55687-55-3]

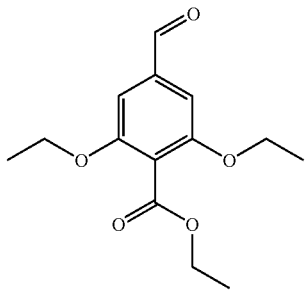

The title compound was prepared as described in DE 243 59 34 (Hoffmann-La Roche AG).

Intermediate B10

3,5-Diethoxy-4-fluoro-benzaldehyde

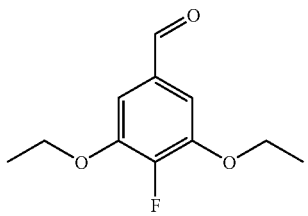

Step 1: tert-Butyl-(4-fluoro-benzyloxy)-dimethyl-silane

To a solution of (4-fluoro-phenyl)-methanol (12.16 g, 96.4 mmol, 1.0 equiv) in anhydrous DMF (50 mL) at 0° C. under Ar was added imidazole (7.22 g, 106.1 mmol, 1.1 equiv) and tert-butyl-chloro-dimethyl-silane (15.99 g, 106.1 mmol, 1.1 equiv). After the addition was completed the cooling bath was removed and the reaction stirred for 18 h at rt. The reaction mixture was poured on ice, extracted with ethyl acetate (2×100 mL) and the combined organic phases washed with a sat. solution of Na₂CO₃ (2×100 mL) and a sat. solution of NaCl (2×100 mL). The organic phase was dried over Na₂SO₄, concentrated by evaporation under reduced pressure yielding a brown oil that was purified by high vacuum destillation (bp 32-35° C. at 0.1 mbar) to give 23.0 g (99%) of the title compound. ¹H NMR (400 MHz, CDCl₃): δ 0.00 (s, 6H), 0.84 (s, 9H), 4.60 (s, 2H), 6.89-6.94 (m, 2H), 7.16-7.20 (m, 2H). MS (EI): 183.1 [M-tert-Bu]⁺.

Step 2: 5-(tert-Butyl-dimethyl-silanyloxymethyl)-2-fluoro-phenol

To a solution of tert-butyl-(4-fluoro-benzyloxy)-dimethyl-silane (5.00 g, 20.8 mmol, 1.0 equiv) in anhydrous THF (20 mL) was added at −78° C. under Ar a solution of sec-BuLi (17.6 mL, 22.8 mmol, 1.1 equiv; 1.3 M solution in hexane) within 30 min. Then a solution of trimethyl borate (2.37 mL, 2.20 g, 20.8 mmol, 1.0 equiv) in anhydrous THF (7.5 mL) was added slowly within 30 min and the cooling bath removed. A solution of conc. acetic acid (2.78 mL, 1.87 g, 31.2 mmol, 1.5 equiv) was slowly added followed by a solution of 35% hydrogen peroxide in water (2.0 mL, 2.23 g, 22.9 mmol, 1.1 equiv) and the reaction allowed to proceed at 0° C. for another 30 min. After stirring at rt for additional 4 h, the mixture was extracted with diethyl ether (2×100 mL) and the combined organic phases washed with a solution of 10% NaOH (2×100 mL) and a sat. solution of NaCl (2×100 mL). The organic phase was dried over Na₂SO₄, concentrated by evaporation under reduced pressure and the crude material purified with column chromatography on silica eluting with hexane/ethyl acetate (19:1) providing 4.80 g (90%) of the title compound. ¹H NMR (400 MHz, CDCl₃): δ 0.00 (s, 6H), 0.84 (s, 9H), 4.56 (s, 2H), 4.97 (br s, 1H), 6.68-6.72 (m, 1H), 6.87-6.94 (m, 2H). MS (EI): 256.2 [M]⁺.

Step 3: 2-(tert-Butyl-dimethyl-silanyloxy)-4-(tert-butyl-dimethyl-silanyloxymethyl)-1-fluoro-benzene To a solution of 5-(tert-butyl-dimethyl-silanyloxymethyl)-2-fluoro-phenol (4.60 g, 17.9 mmol, 1.0 equiv) in anhydrous DMF (20 mL) at 0° C. under Ar was added imidazole (1.34 g, 19.7 mmol, 1.1 equiv) and tert-butyl-chloro-dimethyl-silane (2.97 g, 19.7 mmol, 1.1 equiv). After the addition was completed the cooling bath was removed and the reaction stirred for 18 h at rt. The reaction mixture was poured on ice, extracted with ethyl acetate (2×100 mL) and the combined organic phases washed with a sat. solution of Na₂CO₃ (2×100 mL) and a sat. solution of NaCl (2×100 mL). The organic phase was dried over Na₂SO₄ and concentrated by evaporation under reduced pressure yielding 4.50 g (68%) of the title compound. ¹H NMR (400 MHz, CDCl₃): δ 0.00 (s, 6H), 0.10 (s, 6H), 0.85 (s, 9H), 0.92 (s, 9H), 4.55 (s, 2H), 6.71-6.74 (m, 1H), 6.80-6.83 (m, 1H), 6.87-6.92 (m, 1H). MS (EI): 370.2 [M]⁺.

Step 4: 3-(tert-Butyl-dimethyl-silanyloxy)-5-(tert-butyl-dimethyl-silanyloxymethyl)-2-fluoro-phenol To a solution of 2-(tert-butyl-dimethyl-silanyloxy)-4-(tert-butyl-dimethyl-silanyloxymethyl)-1-fluoro-benzene (23.70 g, 63.9 mmol) 1.0 equiv) in anhydrous THF (130 mL) was added at −78° C. under Ar a solution of sec-BuLi (54.5 mL, 71.6 mmol, 1.1 equiv; 1.3 M solution in hexane) within 30 min. Then a solution of trimethyl borate (7.13 mL, 6.64 g, 63.9 mmol, 1.0 equiv) in anhydrous THF (30 mL) was added slowly within 30 min and the cooling bath removed. A solution of conc. acetic acid (5.49 mL, 5.76 g, 95.9 mmol, 1.5 equiv) was slowly added followed by addition of a solution of 35% hydrogen peroxide in water (6.2 mL, 6.83 g, 70.3 mmol, 1.1 equiv) and the reaction allowed to proceed at 0° C. for another 30 min. After stirring at rt for additional 4 h, the mixture was extracted with diethyl ether (2×100 ml.) and the combined organic phases washed with a solution of 10% NaOH (2×100 mL) and a sat. solution of NaCl (2×100 mL). The organic phase was dried over Na₂SO₄, concentrated by evaporation under reduced pressure, and the crude material was purified with column chromatography on silica eluting with hexane/ethyl acetate (19:1) providing 15.80 g (64%) of the title compound. ¹H NMR (400 MHz, CDCl₃): δ 0.00 (s, 6H), 0.10 (s, 6H), 0.85 (s, 9H), 0.91 (s, 9H), 4.50 (s, 2H), 4.93 (br s, 1H), 6.37 (d, J=5.6 Hz, 1H), 6.47 (d, J=5.6 Hz, 1H). MS (EI): 329.2 [M-tert-Bu]$^+$.

Step 5: tert-Butyl-(3,5-diethoxy-4-fluoro-benzyloxy)-dimethyl-silane

To a solution of 3-(tert-butyl-dimethyl-silanyloxy)-5-(tert-butyl-dimethyl-silanyloxymethyl)-2-fluoro-phenol (5.80 g, 15.0 mmol, 1.0 equiv) in DMF (60 mL) was added $K_2CO_3$ (4.56 g, 33.0 mmol, 2.2 equiv) and ethyl bromide (2.46 mL, 3.60 g, 33.0 mmol, 2.2 equiv) and the reaction mixture stirred under Ar at 60° C. for 5 h. The $K_2CO_3$ was removed by filtration, the crude reaction mixture concentrated by evaporation under reduced pressure, the residue extracted with ethyl acetate (3×100 mL), the combined organic phases washed with water (2×100 ml) and dried over $Na_2SO_4$. The solvent was removed by evaporation under reduced pressure and the crude material purified with column chromatography on silica eluting with hexane/ethyl acetate (99:1) providing 3.10 g (63%) of the title compound. $^1$H NMR (400 MHz, CDCl$_3$): δ 0.00 (s, 6H), 0.85 (s, 9H), 1.33 (t, J=7.0 Hz, 6H), 4.00 (q, J=7.0 Hz, 4H), 4.55 (s, 2H), 6.47 (d, J=6.8 Hz, 2H). MS (ISP): 329.3 [M+H]$^+$.

Step 6: (3,5-Diethoxy-4-fluoro-phenyl)-methanol

To a solution of tert-butyl-(3,5-diethoxy-4-fluoro-benzyloxy)-dimethyl-silane (1.20 g, 3.65 mmol, 1.0 equiv) in methanol (8 mL) was added Dowex 50W-X8 (0.33 g, cation exchange resin) and the reaction mixture stirred under Ar at rt for 22 h. The resin was removed by filtration and the reaction mixture concentrated by evaporation under reduced pressure yielding the title compound in quantitative yield (0.78 g). $^1$H NMR (400 MHz, CDCl$_3$): δ 1.34 (t, J=7.0 Hz, 6H), 1.57 (t, J=5.4 Hz, 1H), 4.01 (q, J=7.0 Hz, 4H), 4.51 (d, J=5.4 Hz, 2H), 6.51 (d, J=6.8 Hz, 2H). MS (EI): 214.2 [M]$^+$.

Step 7: 3,5-Diethoxy-4-fluoro-benzaldehyde

To a solution of (3,5-diethoxy-4-fluoro-phenyl)-methanol (2.30 g, 10.7 mmol, 1.0 equiv) in 1,2-dichloroethane (50 mL) was added activated MnO$_2$ (2.89 g, 33.3 mmol, 3.1 equiv). The reaction mixture was stirred for 21 h at 50° C. and then filtered through Hyflo Super Cel providing after evaporation of the solvent under reduced pressure 1.90 g (83%) of the title compound. $^1$H NMR (400 MHz, CDCl$_3$): δ 1.38 (t, J=7.0 Hz, 6H), 4.09 (q, J=7.0 Hz, 4H), 7.04 (d, J=7.2 Hz, 2H), 9.75 (s, 1H). MS (EI): 212.1 [M]$^+$.

Intermediate B1

4-Chloro-3,5-diethoxy-benzaldehyde

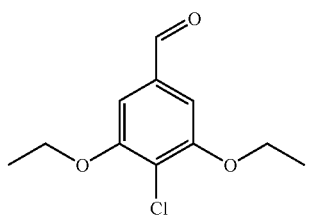

Step 1: 4-Chloro-3,5-diethoxy-benzoic acid ethyl ester

To a solution of 4-amino-3,5-diethoxy-benzoic acid ethyl ester (5.1 g, 20.13 mmol, 1.0 equiv; prepared as described in I. Kompis and A. Wick *Helv. Chim. Acta* 1977, 60, 3025-3034) in water (40 mL) and 37% HCl (40 mL) at 0° C. was added sodium nitrite (1.67 g, 24.16 mmol, 1.2 equiv). After 10 min, copper(I) chloride (12.0 g, 120.81 mmol, 6.0 equiv) was added, the reaction mixture stirred for an additional 5 h at 0° C. and then the ice bath removed. After stirring for 18 h, the crude reaction mixture was adjusted to pH=8 by addition of a solution of 1 M NaOH and the aqueous layer extracted with ethyl acetate (3×100 mL). The combined organic phases were dried over MgSO$_4$, concentrated by evaporation under reduced pressure and the crude material purified by silica column chromatography using a MPLC system (CombiFlash Companion, Isco Inc.) eluting with a gradient of heptane/ethyl acetate providing 5.0 g (91%) of the title compound. $^1$H NMR (300 MHz, CDCl$_3$): δ 1.32 (t, J=7.0 Hz, 4H), 1.40 (t, J=7.0 Hz, 6H), 4.09 (q, J=7.0 Hz, 4H), 4.30 (q, J=7.0 Hz, 2H), 7.18 (s, 2H). $^{13}$C NMR (75 MHz, CDCl$_3$): δ 13.33, 13.66, 60.29, 64.16, 105.75, 115.88, 128.25, 154.49, 165.01. MS (ISP): 273.3 [M+H]$^+$.

Step 2: (4-Chloro-3,5-diethoxy-phenyl)-methanol

To a solution of 4-chloro-3,5-diethoxy-benzoic acid ethyl ester (5.0 g, 18.33 mmol, 1.0 equiv) in dichloromethane (25 mL) was added slowly over a time period of 15 min under slight cooling to −30° C. a solution of diisobutylaluminum hydride (55.0 mL, 55.00 mmol, 3.0 equiv; 1.0 M solution in THF). After 30 min, the excess of hydride was quenched by cautious addition of methanol (10 mL) and water (2 mL). The mixture was stirred for 30 min, a solution of 1 M HCl was added and the aqueous layer extracted with ethyl acetate (3×100 mL). The combined organic phases were dried over MgSO$_4$ and concentrated by evaporation under reduced pressure providing 4.0 g (95%) of the title compound. $^1$H NMR (300 MHz, CDCl$_3$): δ 1.45 (t, J=7.0 Hz, 6H), 1.93 (br s, 1H), 4.09 (q, J=7.0 Hz, 4H), 4.62 (s, 2H), 6.57 (s, 2H). $^{13}$C NMR (75 MHz, CDCl$_3$): δ 14.74, 64.96, 65.18, 104.30, 110.65, 140.29, 155.66. MS (ISP): 231.4 [M+H]$^-$.

Step 3:

To a solution of (4-chloro-3,5-diethoxy-phenyl)-methanol (4.0 g, 17.34 mmol, 1.0 equiv) in THF (40 mL) was added activated MnO$_2$ (15.08 g, 173.4 mmol, 10.0 equiv) and the reaction mixture stirred for 18 h at rt. Filtration through Hyflo Super Cel and purification of the crude material by silica column chromatography using a MPLC system (CombiFlash Companion, Isco Inc.) eluting with a gradient of heptane/ethyl acetate provided 3.7 g (92%) of the title compound. $^1$H NMR (300 MHz, CDCl$_3$): δ 1.50 (t, J=7.0 Hz, 6H), 4.19 (q, J=7.0 Hz, 4H), 7.07 (s, 2H), 9.89 (s, 1H). $^{13}$C NMR (75 MHz, CDCl$_3$): δ 14.61, 65.22, 106.26, 118.64, 135.08, 156.22, 191.01. MS (EI): 229.4 [M]$^+$.

Intermediate B12

4-Bromo-3,5-diethoxy-benzaldehyde [CAS RN 363166-11-4]

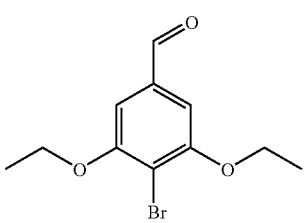

The title compound was prepared from 4-bromo-3,5-dihydroxy-benzoic acid as described in S. P. Dudek, H. D. Sikes and C. E. D. Chidsey *J. Am. Chem. Soc.* 2001, 123, 8033-8038.

Intermediate B13

4-Amino-3,5-diethoxy-benzaldehyde

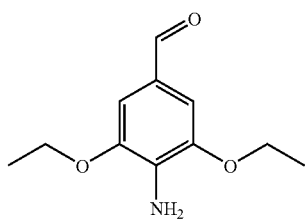

Step 1: (4-Amino-3,5-diethoxy-phenyl)-methanol

To a solution of 4-amino-3,5-diethoxy-benzoic acid ethyl ester (2.8 g, 11.05 mmol, 1.0 equiv; prepared as described in I. Kompis, A. Wick, *Helv. Chim. Acta* 1977, 60, 3025-3034) in dichloromethane (50 mL) at 0° C. under Ar was slowly added diisobutylaluminum hydride (27.6 mL, 27.64 mmol, 2.5 equiv; 1.0 M solution in dichloromethane) over a time period of 15 min and the cooling bath removed on completion of addition. After stirring for 18 h, the excess of hydride was quenched by cautious addition of a sat. solution of potassium sodium tartrate (10 mL). The solidified mixture was extracted with dichloromethane (5×200 mL) and THF (2×150 mL), the combined organic phases washed with water (3×100 mL), dried over $MgSO_4$, concentrated by evaporation under reduced pressure and the crude material purified by column chromatography on silica eluting with a gradient of heptane/ethyl acetate (4:1→1:1) providing 1.10 g (47%) of the title compound. $^1$H NMR (300 MHz, $CDCl_3$): δ 1.42 (t, J=7.0 Hz, 3H), 3.82 (br s, 2H), 4.05 (q, J=7.0 Hz, 2H), 4.54 (s, 2H), 6.50 (s, 2H). $^{13}$C NMR (75 MHz, $CDCl_3$): δ 15.03, 66.00 104.51, 125.44, 129.89, 146.71. MS (ISP): 211.9 $[M+H]^+$.

Step 2: 4-Amino-3,5-diethoxy-benzaldehyde

To a solution of (4-amino-3,5-diethoxy-phenyl)-methanol (0.79 g, 3.74 mmol, 1.0 equiv) in DMF (20 mL) was added activated $MnO_2$ (1.63 g, 18.70 mmol, 5.0 equiv). The reaction mixture was stirred for 24 h at rt, filtered through Hyflo Super Cel, the filtrate was extracted with ethyl acetate (3×50 mL), and the combined organic phase was washed with water, dried over $MgSO_4$ and evaporated to dryness providing thereby 0.69 g (88%) of the title compound. $^1$H NMR (300 MHz, DMSO): δ 1.46 (t, J=7.0 Hz, 3H), 4.15 (q, J=7.0 Hz, 2H), 4.50 (br s, 2H), 7.04 (s, 2H), 9.70 (s, 1H). MS (ISP): 210.0 $[M+H]^+$.

Intermediate B14

3,5-Diethoxy-4-pyrrol-1-yl-benzaldehyde

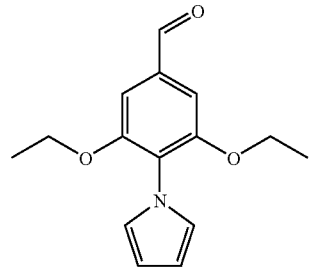

Step 1: 3,5-Diethoxy-4-pyrrol-1-yl-benzoic acid ethyl ester

To a solution of 4-amino-3,5-diethoxy-benzoic acid ethyl ester (3.0 g, 11.84 mmol, 1.0 equiv; prepared as described in I. Kompis and A. Wick, *Helv. Chim. Acta* 1977, 60, 3025-3034) in heptane (10 mL) and conc. acetic acid (0.2 mL) was added 2,5-dimethoxy-tetrahydro-furan (1.88 g, 14.21 mmol, 1.2 equiv). After heating to reflux for 5 h, a Dean-Stark apparatus was attached and the reaction mixture heated for an additional time period of 5 h. Filtration of the crude reaction mixture and crystallization at 0° C. from heptane provided 2.94 g (82%) of the title compound. $^1$H NMR (300 MHz, DMSO): δ 1.15 (t, J=7.0 Hz, 6H), 1.27 (t, J=7.1 Hz, 3H), 3.98 (q, J=7.0 Hz, 4H), 4.28 (q, J=7.1 Hz, 2H), 6.07-6.08 (m, 2H), 6.73-6.74 (m, 2H), 7.22 (s, 2H). $^{13}$C NMR (75 MHz, DMSO): δ 14.11, 14.35, 61.06, 64.57, 106.87, 107.64, 122.61, 123.33, 129.29, 153.75, 165.06. MS (ISP): 303.4 $[M+H]^+$.

Step 2: 3,5-Diethoxy-4-pyrrol-1-yl-benzaldehyde

To a solution of 3,5-diethoxy-4-pyrrol-1-yl-benzoic acid ethyl ester (1.51 g, 4.98 mmol, 1.0 equiv) in toluene (5 mL) was added slowly over a time period of 15 min under slight cooling to 20° C. a solution of diisobutylaluminum hydride (8.9 mL, 12.45 mmol, 2.5 equiv; 20% solution in toluene). After 1 h, the excess of hydride was quenched by cautious addition of water (10 mL) and a 28% solution of NaOH (2 mL). The mixture was stirred for 30 min and the organic phase filtered over Hyflo Super Cel. The aqueous layer was extracted with toluene (2×50 mL), the combined organic phases washed with a sat. solution of NaCl (2×50 mL) and concentrated by evaporation under reduced pressure to afford 1.30 g (100%) of (3,5-diethoxy-4-pyrrol-1-yl-phenyl)-methanol. The crude alcohol (1.30 g, 4.98 mmol, 1.0 equiv) was dissolved in toluene (20 mL), and activated $MnO_2$ (7.79 g, 89.5 mmol, 18.0 equiv) was added. The reaction mixture was heated to reflux for 7 h, after which time the reaction mixture was filtered through Hyflo Super Cel and concentrated yielding 1.15 g (89% yield) of the title compound. $^1$H NMR (300 MHz, DMSO): δ 1.17 (t, J=7.0 Hz, 6H), 4.02 (q, J=7.0 Hz, 4H), 6.08-6.09 (m, 2H), 6.75-6.76 (m, 2H), 7.25 (s, 2H), 9.89 (s, 1H). MS (ISP): 260.1 $[M+H]^+$.

Intermediate B15

2,6-Diethoxy-4'-fluoro-biphenyl-4-carbaldehyde

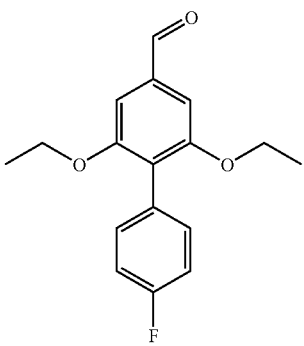

3,5-Diethoxy-4-iodo-benzaldehyde (14.05 g, 43.89 mmol, 1.0 equiv; prepared as described in WO 01/326 33 A1 (F. Hoffmann-La Roche AG); [CAS RN 338454-05-0]) was dissolved under Ar in toluene (180 mL) and water (20 mL) and treated successively with 4-fluorophenyl boronic acid (12.28 g, 87.78 mmol, 2.0 equiv), $K_3PO_4$ (50.12 g, 236.12 mmol, 5.38 equiv), tricyclohexylphosphine (2.80 g, 9.66 mmol, 0.22 equiv) and palladium(II) acetate (1.08 g, 4.83 mmol, 0.11 equiv). The reaction mixture was heated to 100° C. for 18 h under scrupulous exclusion of oxygen, when GC indicated the absence of starting iodo-compound. The reaction mixture was poured on crashed ice/$NH_4Cl$, extracted with ethyl acetate (2×200 mL) and the combined organic phases washed with a sat. solution of NaCl (2×100 mL) and water (2×100 mL). The organic phase was dried over $Na_2SO_4$, concentrated by evaporation under reduced pressure and the crude material purified by silica column chromatography eluting with a mixture of hexane/ethyl acetate (9:1). Recrystallization from hexane/ethyl acetate provided 10.44 g (83%) of the title compound as white crystals. MS (EI): 288.2 $[M]^+$.

Intermediate B16

4-Methoxy-3-propoxy-benzaldehyde [CAS RN 5922-56-5]

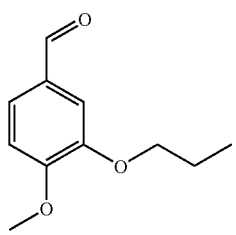

The title compound was prepared by reaction of isovanillin with propyl iodide in DMF using $K_2CO_3$ as base in analogy to the preparation of 3-ethoxy-4-methyl-benzaldehyde (intermediate B19, vide infra).

Intermediate B17

3-Butoxy-4-methoxy-benzaldehyde

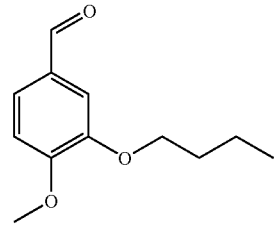

The title compound was prepared analogously to 3-ethoxy-4-methyl-benzaldehyde (intermediate B19, vide infra) by reaction of 3-hydroxy-4-methoxy-benzaldehyde with 4-bromo-butane in DMF using $K_2CO_3$ as base. MS (ISP): 209.1 $[M+H]^+$.

Intermediate B18

3-Allyloxy-4-methoxy-benzaldehyde [CAS RN 225939-36-6]

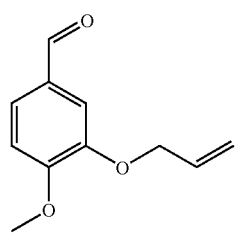

The title compound was prepared analogously to 3-ethoxy-4-methyl-benzaldehyde (intermediate B19, vide infra) by reaction of 3-hydroxy-4-methoxy-benzaldehyde with allyl-bromide in DMF using $K_2CO_3$ as base (see also A. W. White, R. Almassy, A. H. Calvert, N. J. Curtin, R. J. Griffin, Z. Hostomsky, K. Maegley, D. R. Newell, S. Srinivasan and B. T. Golding *J. Med. Chem.* 2000, 43, 4084-4097).

Intermediate B19

3-Ethoxy-4-methyl-benzaldehyde [CAS RN 157143-20-9]

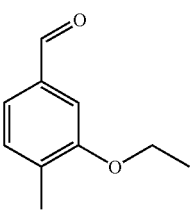

The title compound was prepared by reaction of commercially available 3-hydroxy-4-methyl-benzaldehyde with ethyl iodide in DMF using $K_2CO_3$ as base in analogy to the procedure described in M. J. Ashton, D. C. Cook, G. Fenton, J.-A. Karlsson, M. N. Palfreyman, D. Raeburn, A. J. Ratcliffe, J. E. Souness, S. Thurairatnam and N. Vicker *J. Med. Chem.* 1994, 37, 1696-1703.

Intermediate B20

2-Ethoxy-4'-fluoro-biphenyl-4-carbaldehyde

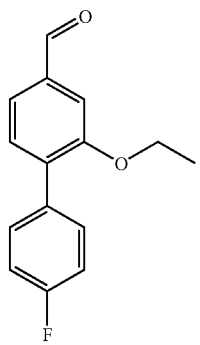

Step 1: 2-Ethoxy-4'-fluoro-biphenyl-4-carboxylic acid ethyl ester

To a solution of 3-ethoxy-4-iodo-benzoic acid ethyl ester (0.76 g, 2.37 mmol, 1.0 equiv; [CAS RN 741699-04-7]) in anhydrous DMF (12 mL) under Ar was added 4-fluorophenyl boronic acid (0.40 g, 2.86 mmol, 1.20 equiv), $K_3PO_4$ (0.86 g, 4.04 mmol, 1.70 equiv) and tetrakis(triphenylphosphine) palladium(0) (0.082 g, 0.071 mmol, 0.03 equiv) and the reaction mixture heated to 80° C. After 16 h, the reaction mixture was poured on crashed ice/$NH_4Cl$, extracted twice with ethyl acetate, the combined organic phases washed with water and a sat. solution of NaCl, dried over $MgSO_4$ and concentrated by evaporation under reduced pressure. The crude material was purified with silica column chromatography eluting with hexane/ethyl acetate (95:5) to yield 0.51 g (75%) of the title compound as a colorless oil. MS (ISP): 289.3 $[M+H]^+$.

Step 2: (2-Ethoxy-4'-fluoro-biphenyl-4-yl)-methanol

To a solution of 2-ethoxy-4'-fluoro-biphenyl-4-carboxylic acid ethyl ester (0.50 g, 1.73 mmol, 1.0 equiv) in anhydrous THF (10 mL) was added dropwise at −10° C. diisobutylaluminum hydride (5.2 mL, 5.20 mmol, 3.0 equiv; 1 M solution in hexane) and the ccolong bath removed. After stirring for an additional time period of 60 min at rt, the reaction mixture was carefully poured on crashed ice/diluted HCl, extracted twice with ethyl acetate, the combined organic phases washed with water and a sat. solution of NaCl, dried over $MgSO_4$ and concentrated by evaporation under reduced pressure. The title compound was isolated in quantitative yield (0.43 g) as a colorless viscous oil, sufficiently pure for the next step. MS (ISP): 229.3 $[M+H-H_2O]^1$.

Step 3: 2-Ethoxy-4'-fluoro-biphenyl-4-carbaldehyde

To a solution of (2-ethoxy-4'-fluoro-biphenyl-4-yl)-methanol (0.43 g, 1.75 mmol, 1.0 equiv) in dichloromethane (20 mL) was added activated $MnO_2$ (3.04 g, 34.92 mmol, 20.0 equiv) and the reaction mixture stirred vigorously for 3 h at ambient temperature. The reaction mixture was filtered over a pad of Celite, rinsed generously with dichloromethane and evaporated to dryness under reduced pressure. The crude material was purified with silica column chromatography eluting with hexane/ethyl acetate (4:1) to yield 0.33 g (77%) of the title compound as white crystals. MS (EI): 244.1 $[M]^+$.

Examples 2 to 102

According to the procedure described for the synthesis of example 1/step 7 further benzoimidazole, tetrahydro-quinoxaline, benzotriazole and dihydro-imidazo[4,5-c]pyridinone derivatives have been synthesized from 2-methyl-1-piperidin-4-yl-1H-benzoimidazole-5-carboxylic acid allyl ester dihydrochloride (intermediate A1), 2-oxo-1-piperidin-4-yl-2,3-dihydro-1H-benzoimidazole-5-carboxylic acid allyl ester dihydrochloride (intermediate A2), 3-oxo-1-piperidin-4-yl-1,2,3,4-tetrahydro-quinoxaline-6-carboxylic acid allyl ester dihydrochloride (intermediate A3), 1-piperidin-4-yl-1H-benzotriazole-5-carboxylic acid allyl ester dihydrochloride (intermediate A4) and 1-piperidin-4-yl-1,5-dihydro-imidazo[4,5-c]pyridin-4-one dihydrochloride (intermediate A5) and the respective benzaldehyde intermediate as indicated in Table 1. The results are compiled in Table 1 and comprise example 2 to example 102.

TABLE 1

| No | MW | Compound Name | Starting Materials | ISP $[M + H]^+$ |
|---|---|---|---|---|
| 2 | 427.93 | 1-[1-(4-chloro-3-ethoxy-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 4-chloro-3-ethoxy-benzaldehyde (intermediate B2) | $[M + H]^+$ 428.3 |
| 3 | 449.55 | 1-[1-(4-allyloxy-3-ethoxy-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 4-allyloxy-3-ethoxy-benzaldehyde (commercially available) | $[M + H]^+$ 450.4 |
| 4 | 451.57 | 1-[1-(3-ethoxy-4-isopropoxy-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 3-ethoxy-4-isopropoxy-benzaldehyde (commercially available) | $[M + H]^+$ 452.3 |

TABLE 1-continued

| No | MW | Compound Name | Starting Materials | ISP [M + H]+ |
|---|---|---|---|---|
| 5 | 465.59 | 1-[1-(3-ethoxy-4-isobutoxy-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 3-ethoxy-4-isobutoxy-benzaldehyde (commercially available) | [M + H]+ 466.4 |
| 6 | 479.62 | 1-{1-[3-ethoxy-4-(1-ethyl-propoxy)-benzyl]-piperidin-4-yl}-2-methyl-1H-benzoimidazole-5-carboxylic acid | 2-methyl-1-piperidin-4-yl-1H-benzoimidazole-5-carboxylic acid allyl ester dihydrochloride (intermediate A1) and 3-ethoxy-4-(1-ethyl-propoxy)-benzaldehyde (intermediate B3) | [M + H]+ 480.4 |
| 7 | 477.60 | 1-[1-(4-cyclopentyloxy-3-ethoxy-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 4-cyclopentyloxy-3-ethoxy-benzaldehyde (commercially available) | [M + H]+ 478.4 |
| 8 | 499.61 | 1-[1-(4-benzyloxy-3-ethoxy-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 4-benzyloxy-3-ethoxy-benzaldehyde (commercially available) | [M + H]+ 500.4 |
| 9 | 459.49 | 1-[1-(4-difluoromethoxy-3-ethoxy-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 4-difluoromethoxy-3-ethoxy-benzaldehyde (commercially available) | [M + H]+ 460.3 |
| 10 | 437.54 | 1-[1-(3-isopropoxy-4-methoxy-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 3-isopropoxy-4-methoxy-benzaldehyde (commercially available) | [M + H]+ 438.4 |
| 11 | 441.50 | 1-{1-[3-(2-fluoro-ethoxy)-4-methoxy-benzyl]-piperidin-4-yl}-2-methyl-1H-benzoimidazole-5-carboxylic acid | 2-methyl-1-piperidin-4-yl-1H-benzoimidazole-5-carboxylic acid allyl ester dihydrochloride (intermediate A1) and 3-(2-fluoro-ethoxy)-4-methoxy-benzaldehyde (intermediate B4) | [M + H]+ 442.3 |
| 12 | 451.57 | 1-[1-(3-isobutoxy-4-methoxy-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 3-isobutoxy-4-methoxy-benzaldehyde (intermediate B5) | [M + H]+ 452.3 |
| 13 | 463.58 | 1-[1-(3-cyclopentyloxy-4-methoxy-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 3-cyclopentyloxy-4-methoxy-benzaldehyde (commercially available) | [M + H]+ 464.4 |
| 14 | 475.59 | 1-[1-(8-ethoxy-2,2-dimethyl-2H-chromen-6-ylmethyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 8-ethoxy-2,2-dimethyl-2H-chromene-6-carbaldehyde (intermediate B6) | [M + H]+ 476.4 |
| 15 | 437.54 | 1-[1-(3,5-diethoxy-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 3,5-diethoxy-benzaldehyde (intermediate B7) | [M + H]+ 438.4 |
| 16 | 465.59 | 1-[1-(3,5-diisopropoxy-benzyl)-piperidin-4-yl]-2-methyl-1H- | 2-methyl-1-piperidin-4-yl-1H-benzoimidazole-5-carboxylic acid allyl ester dihydrochloride | [M + H]+ 466.4 |

TABLE 1-continued

| No | MW | Compound Name | Starting Materials | ISP [M + H]+ |
|---|---|---|---|---|
| | | benzoimidazole-5-carboxylic acid | (intermediate A1) and 3,5-diisopropoxy-benzaldehyde (intermediate B8) | |
| 17 | 509.60 | 1-[1-(3,5-diethoxy-4-ethoxycarbonyl-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 2,6-diethoxy-4-formyl-benzoic acid ethyl ester (intermediate B9) | [M + H]+ 510.4 |
| 18 | 455.53 | 1-[1-(3,5-diethoxy-4-fluoro-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 3,5-diethoxy-4-fluoro-benzaldehyde (intermediate B10) | [M + H]+ 456.4 |
| 19 | 471.98 | 1-[1-(4-chloro-3,5-diethoxy-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 4-chloro-3,5-diethoxy-benzaldehyde (intermediate B11) | [M + H]+ 472.3 |
| 20 | 516.44 | 1-[1-(4-bromo-3,5-diethoxy-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 4-bromo-3,5-diethoxy-benzaldehyde (intermediate B12) | [M + H]+ 518.3 |
| 21 | 452.55 | 1-[1-(4-amino-3,5-diethoxy-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 4-amino-3,5-diethoxy-benzaldehyde (intermediate B13) | [M + H]+ 453.4 |
| 22 | 502.61 | 1-[1-(3,5-diethoxy-4-pyrrol-1-yl-benzyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 3,5-diethoxy-4-pyrrol-1-yl-benzaldehyde (intermediate B14) | [M + H]+ 503.4 |
| 23 | 531.63 | 1-[1-(2,6-diethoxy-4'-fluoro-biphenyl-4-ylmethyl)-piperidin-4-yl]-2-methyl-1H-benzoimidazole-5-carboxylic acid | 2-methyl-1-piperidin-4-yl-1H-benzoimidazole-5-carboxylic acid allyl ester dihydrochloride (intermediate A1) and 2,6-diethoxy-4'-fluoro-biphenyl-4-carbaldehyde (intermediate B15) | [M + H]+ 532.4 |
| 24 | 413.45 | 1-[1-(3-ethoxy-4-fluoro-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 3-ethoxy-4-fluoro-benzaldehyde (intermediate B1) | [M + H]+ 414.3 |
| 25 | 429.90 | 1-[1-(4-chloro-3-ethoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 4-chloro-3-ethoxy-benzaldehyde (intermediate B2) | [M + H]+ 430.3 |
| 26 | 411.46 | 1-[1-(3-ethoxy-4-hydroxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 3-ethoxy-4-hydroxy-benzaldehyde (commercially available) | [M + H]+ 412.2 |
| 27 | 425.48 | 1-[1-(3-ethoxy-4-methoxy-benzyl)- | 2-oxo-1-piperidin-4-yl-2,3-dihydro-1H-benzoimidazole-5- | [M + H]+ 426.3 |

TABLE 1-continued

| No | MW | Compound Name | Starting Materials | ISP [M + H]+ |
|---|---|---|---|---|
| | | piperidin-4-yl]-2-oxo-2,3-dihydro-1H-benzoimidazole-5-carboxylic acid | carboxylic acid allyl ester dihydrochloride (intermediate A2) and 3-ethoxy-4-methoxy-benzaldehyde (commercially available) | |
| 28 | 439.51 | 1-[1-(3,4-diethoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 3,4-diethoxy-benzaldehyde (commercially available) | [M + H]+ 440.3 |
| 29 | 451.52 | 1-[1-(4-allyloxy-3-ethoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 4-allyloxy-3-ethoxy-benzaldehyde (commercially available) | [M + H]+ 452.3 |
| 30 | 453.54 | 1-[1-(3-ethoxy-4-isopropoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 3-ethoxy-4-isopropoxy-benzaldehyde (commercially available) | [M + H]+ 454.3 |
| 31 | 467.57 | 1-[1-(3-ethoxy-4-isobutoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 3-ethoxy-4-isobutoxy-benzaldehyde (commercially available) | [M + H]+ 468.4 |
| 32 | 481.59 | 1-{1-[3-ethoxy-4-(1-ethyl-propoxy)-benzyl]-piperidin-4-yl}-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 3-ethoxy-4-(1-ethyl-propoxy)-benzaldehyde (intermediate B3) | [M + H]+ 482.4 |
| 33 | 479.58 | 1-[1-(4-cyclopentyloxy-3-ethoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 4-cyclopentyloxy-3-ethoxy-benzaldehyde (commercially available) | [M + H]+ 480.4 |
| 34 | 501.58 | 1-[1-(4-benzyloxy-3-ethoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 4-benzyloxy-3-ethoxy-benzaldehyde (commercially available) | [M + H]+ 502.4 |
| 35 | 461.46 | 1-[1-(4-difluoromethoxy-3-ethoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 4-difluoromethoxy-3-ethoxy-benzaldehyde (commercially available) | [M + H]+ 462.3 |
| 36 | 439.51 | 1-[1-(4-methoxy-3-propoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 4-methoxy-3-propoxy-benzaldehyde (intermediate B16) | [M + H]+ 440.4 |

TABLE 1-continued

| No | MW | Compound Name | Starting Materials | ISP [M + H]+ |
|---|---|---|---|---|
| 37 | 443.47 | 1-{1-[3-(2-fluoro-ethoxy)-4-methoxy-benzyl]-piperidin-4-yl}-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 3-(2-fluoro-ethoxy)-4-methoxy-benzaldehyde (intermediate B4) | [M + H]+ 444.3 |
| 38 | 453.54 | 1-[1-(3-butoxy-4-methoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 3-butoxy-4-methoxy-benzaldehyde (intermediate B17) | [M + H]+ 454.4 |
| 39 | 453.54 | 1-[1-(3-isobutoxy-4-methoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 3-isobutoxy-4-methoxy-benzaldehyde (intermediate B5) | [M + H]+ 454.3 |
| 40 | 465.55 | 1-[1-(3-cyclopentyloxy-4-methoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 3-cyclopentyloxy-4-methoxy-benzaldehyde (commercially available) | [M + H]+ 466.4 |
| 41 | 477.56 | 1-[1-(8-ethoxy-2,2-dimethyl-2H-chromen-6-ylmethyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 8-ethoxy-2,2-dimethyl-2H-chromene-6-carbaldehyde (intermediate B6) | [M + H]+ 478.4 |
| 42 | 439.51 | 1-[1-(3,5-diethoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 3,5-diethoxy-benzaldehyde (intermediate B7) | [M + H]+ 440.3 |
| 43 | 467.57 | 1-[1-(3,5-diisopropoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 3,5-diisopropoxy-benzaldehyde (intermediate B8) | [M + H]+ 468.4 |
| 44 | 511.57 | 1-[1-(3,5-diethoxy-4-ethoxycarbonyl-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 2,6-diethoxy-4-formyl-benzoic acid ethyl ester (intermediate B9) | [M + H]+ 512.4 |
| 45 | 457.50 | 1-[1-(3,5-diethoxy-4-fluoro-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 3,5-diethoxy-4-fluoro-benzaldehyde (intermediate B10) | [M + H]+ 458.2 |
| 46 | 473.96 | 1-[1-(4-chloro-3,5-diethoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 4-chloro-3,5-diethoxy-benzaldehyde (intermediate B11) | [M + H]+ 474.2 |

TABLE 1-continued

| No | MW | Compound Name | Starting Materials | ISP [M + H]+ |
|---|---|---|---|---|
| 47 | 518.41 | 1-[1-(4-bromo-3,5-diethoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 4-bromo-3,5-diethoxy-benzaldehyde (intermediate B12) | [M + H]+ 518.3 |
| 48 | 454.53 | 1-[1-(4-amino-3,5-diethoxy-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 4-amino-3,5-diethoxy-benzaldehyde (intermediate B13) | [M + H]+ 455.4 |
| 49 | 504.59 | 1-[1-(3,5-diethoxy-4-pyrrol-1-yl-benzyl)-piperidin-4-yl]-2-oxo-2,3-dihydro-1H-benzoimidazole-5-carboxylic acid | 2-oxo-1-piperidin-4-yl-2,3-dihydro-1H-benzoimidazole-5-carboxylic acid allyl ester dihydrochloride (intermediate A2) and 3,5-diethoxy-4-pyrrol-1-yl-benzaldehyde (intermediate B14) | [M + H]+ 505.4 |
| 50 | 443.93 | 1-[1-(4-chloro-3-ethoxy-benzyl)-piperidin-4-yl]-3-oxo-1,2,3,4-tetrahydro-quinoxaline-6-carboxylic acid | 3-oxo-1-piperidin-4-yl-1,2,3,4-tetrahydro-quinoxaline-6-carboxylic acid allyl ester dihydrochloride (intermediate A3) and 4-chloro-3-ethoxy-benzaldehyde (intermediate B2) | [M + H]+ 444.3 |
| 51 | 475.49 | 1-[1-(4-difluoromethoxy-3-ethoxy-benzyl)-piperidin-4-yl]-3-oxo-1,2,3,4-tetrahydro-quinoxaline-6-carboxylic acid | 3-oxo-1-piperidin-4-yl-1,2,3,4-tetrahydro-quinoxaline-6-carboxylic acid allyl ester dihydrochloride (intermediate A3) and 4-difluoromethoxy-3-ethoxy-benzaldehyde (commercially available) | [M + H]+ 476.3 |
| 52 | 479.58 | 1-[1-(3-cyclopentyloxy-4-methoxy-benzyl)-piperidin-4-yl]-3-oxo-1,2,3,4-tetrahydro-quinoxaline-6-carboxylic acid | 3-oxo-1-piperidin-4-yl-1,2,3,4-tetrahydro-quinoxaline-6-carboxylic acid allyl ester dihydrochloride (intermediate A3) and 3-cyclopentyloxy-4-methoxy-benzaldehyde (commercially available) | [M + H]+ 480.4 |
| 53 | 481.59 | 1-[1-(3,5-diisopropoxy-benzyl)-piperidin-4-yl]-3-oxo-1,2,3,4-tetrahydro-quinoxaline-6-carboxylic acid | 3-oxo-1-piperidin-4-yl-1,2,3,4-tetrahydro-quinoxaline-6-carboxylic acid allyl ester dihydrochloride (intermediate A3) and 3,5-diisopropoxy-benzaldehyde (intermediate B8) | [M + H]+ 482.4 |
| 54 | 525.60 | 1-[1-(3,5-diethoxy-4-ethoxycarbonyl-benzyl)-piperidin-4-yl]-3-oxo-1,2,3,4-tetrahydro-quinoxaline-6-carboxylic acid | 3-oxo-1-piperidin-4-yl-1,2,3,4-tetrahydro-quinoxaline-6-carboxylic acid allyl ester dihydrochloride (intermediate A3) and 2,6-diethoxy-4-formyl-benzoic acid ethyl ester (intermediate B9) | [M + H]+ 526.4 |
| 55 | 471.53 | 1-[1-(3,5-diethoxy-4-fluoro-benzyl)-piperidin-4-yl]-3-oxo-1,2,3,4-tetrahydro-quinoxaline-6-carboxylic acid | 3-oxo-1-piperidin-4-yl-1,2,3,4-tetrahydro-quinoxaline-6-carboxylic acid allyl ester dihydrochloride (intermediate A3) and 3,5-diethoxy-4-fluoro-benzaldehyde (intermediate B10) | [M + H]+ 472.2 |
| 56 | 487.98 | 1-[1-(4-chloro-3,5-diethoxy-benzyl)-piperidin-4-yl]-3-oxo-1,2,3,4-tetrahydro-quinoxaline-6-carboxylic acid | 3-oxo-1-piperidin-4-yl-1,2,3,4-tetrahydro-quinoxaline-6-carboxylic acid allyl ester dihydrochloride (intermediate A3) and 4-chloro-3,5-diethoxy- | [M + H]+ 488.2 |

TABLE 1-continued

| No | MW | Compound Name | Starting Materials | ISP [M + H]+ |
|---|---|---|---|---|
| 57 | 532.44 | 1-[1-(4-bromo-3,5-diethoxy-benzyl)-piperidin-4-yl]-3-oxo-1,2,3,4-tetrahydro-quinoxaline-6-carboxylic acid | benzaldehyde (intermediate B11) 3-oxo-1-piperidin-4-yl-1,2,3,4-tetrahydro-quinoxaline-6-carboxylic acid allyl ester dihydrochloride (intermediate A3) and 4-bromo-3,5-diethoxy-benzaldehyde (intermediate B12) | [M + H]+ 534.3 |
| 58 | 518.61 | 1-[1-(3,5-diethoxy-4-pyrrol-1-yl-benzyl)-piperidin-4-yl]-3-oxo-1,2,3,4-tetrahydro-quinoxaline-6-carboxylic acid | 3-oxo-1-piperidin-4-yl-1,2,3,4-tetrahydro-quinoxaline-6-carboxylic acid allyl ester dihydrochloride (intermediate A3) and 3,5-diethoxy-4-pyrrol-1-yl-benzaldehyde (intermediate B14) | [M + H]+ 519.4 |
| 59 | 547.63 | 1-[1-(2,6-diethoxy-4'-fluoro-biphenyl-4-ylmethyl)-piperidin-4-yl]-3-oxo-1,2,3,4-tetrahydro-quinoxaline-6-carboxylic acid | 3-oxo-1-piperidin-4-yl-1,2,3,4-tetrahydro-quinoxaline-6-carboxylic acid allyl ester dihydrochloride (intermediate A3) and 2,6-diethoxy-4'-fluoro-biphenyl-4-carbaldehyde (intermediate B15) | [M + H]+ 548.4 |
| 60 | 398.44 | 1-[1-(3-ethoxy-4-fluoro-benzyl-piperidin-4-yl]-1H-benzotriazole-5-carboxylic acid | 1-piperidin-4-yl-1H-benzotriazole-5-carboxylic acid allyl ester dihydrochloride (intermediate A4) and 3-ethoxy-4-fluoro-benzaldehyde (intermediate B1) | [M + H]+ 399.3 |
| 61 | 414.89 | 1-[1-(4-chloro-3-ethoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 4-chloro-3-ethoxy-benzaldehyde (intermediate B2) | [M + H]+ 415.3 |
| 62 | 396.45 | 1-[1-(3-ethoxy-4-hydroxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 3-ethoxy-4-hydroxy-benzaldehyde (commercially available) | [M + H]+ 397.2 |
| 63 | 410.47 | 1-[1-(3-ethoxy-4-methoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 3-ethoxy-4-methoxy-benzaldehyde (commercially available) | [M + H]+ 411.3 |
| 64 | 424.50 | 1-[1-(3,4-diethoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 3,4-diethoxy-benzaldehyde (commercially available) | [M + H]+ 425.3 |
| 65 | 436.51 | 1-[1-(4-allyloxy-3-ethoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 4-allyloxy-3-ethoxy-benzaldehyde (commercially available) | [M + H]+ 437.4 |
| 66 | 438.53 | 1-[1-(3-ethoxy-4-isopropoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 3-ethoxy-4-isopropoxy-benzaldehyde (commercially available) | [M + H]+ 439.3 |
| 67 | 452.55 | 1-[1-(3-ethoxy-4-isobutoxy-benzyl)-piperidin-4-yl]-1H-benzotriazole-5- | 1-piperidin-4-yl-1H-benzotriazole-5-carboxylic acid allyl ester dihydrochloride (intermediate A4) and | [M + H]+ 453.4 |

TABLE 1-continued

| No | MW | Compound Name | Starting Materials | ISP [M + H]+ |
|----|------|---------------|--------------------|--------------|
| | | carboxylic acid | 3-ethoxy-4-isobutoxy-benzaldehyde (commercially available) | |
| 68 | 466.58 | 1-{1-[3-ethoxy-4-(1-ethyl-propoxy)-benzyl]-piperidin-4-yl}-1H-benzotriazole-5-carboxylic acid | 1-piperidin-4-yl-1H-benzotriazole-5-carboxylic acid allyl ester dihydrochloride (intermediate A4) and 3-ethoxy-4-(1-ethyl-propoxy)-benzaldehyde (intermediate B3) | [M + H]+ 467.4 |
| 69 | 464.57 | 1-[1-(4-cyclopentyloxy-3-ethoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 4-cyclopentyloxy-3-ethoxy-benzaldehyde (commercially available) | [M + H]+ 465.4 |
| 70 | 486.57 | 1-[1-(4-benzyloxy-3-ethoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 4-benzyloxy-3-ethoxy-benzaldehyde (commercially available) | [M + H]+ 487.4 |
| 71 | 446.45 | 1-[1-(4-difluoromethoxy-3-ethoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 4-difluoromethoxy-3-ethoxy-benzaldehyde (commercially available) | [M + H]+ 447.3 |
| 72 | 424.50 | 1-[1-(4-methoxy-3-propoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 4-methoxy-3-propoxy-benzaldehyde (intermediate B16) | [M + H]+ 425.3 |
| 73 | 424.50 | 1-[1-(3-isopropoxy-4-methoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 3-isopropoxy-4-methoxy-benzaldehyde (commercially available) | [M + H]+ 425.3 |
| 74 | 422.48 | 1-[1-(3-allyloxy-4-methoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 3-allyloxy-4-methoxy-benzaldehyde (intermediate B18) | [M + H]+ 423.3 |
| 75 | 420.47 | 1-[1-(4-methoxy-3-prop-2-ynyloxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 4-methoxy-3-prop-2-ynyloxy-benzaldehyde (commercially available) | [M + H]+ 421.3 |
| 76 | 438.53 | 1-[1-(3-butoxy-4-methoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 3-butoxy-4-methoxy-benzaldehyde (intermediate B17) | [M + H]+ 439.4 |
| 77 | 438.53 | 1-[1-(3-isobutoxy-4-methoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 3-isobutoxy-4-methoxy-benzaldehyde (intermediate B5) | [M + H]+ 439.3 |
| 78 | 450.54 | 1-[1-(3-cyclopentyloxy-4-methoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 3-cyclopentyloxy-4-methoxy- | [M + H]+ 451.4 |

TABLE 1-continued

| No | MW | Compound Name | Starting Materials | ISP [M + H]+ |
|---|---|---|---|---|
| 79 | 462.55 | 1-[1-(8-ethoxy-2,2-dimethyl-2H-chromen-6-ylmethyl)-piperidin-4-yl]-1H-benzotriazole-5-carboxylic acid | benzaldehyde (commercially available) 1-piperidin-4-yl-1H-benzotriazole-5-carboxylic acid allyl ester dihydrochloride (intermediate A4) and 8-ethoxy-2,2-dimethyl-2H-chromene-6-carbaldehyde (intermediate B6) | [M + H]+ 463.3 |
| 80 | 424.50 | 1-[1-(3,5-diethoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 3,5-diethoxy-benzaldehyde (intermediate B7) | [M + H]+ 425.3 |
| 81 | 442.49 | 1-[1-(3,5-diethoxy-4-fluoro-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 3,5-diethoxy-4-fluoro-benzaldehyde (intermediate B10) | [M + H]+ 443.3 |
| 82 | 458.95 | 1-[1-(4-chloro-3,5-diethoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 4-chloro-3,5-diethoxy-benzaldehyde (intermediate B11) | [M + H]+ 459.3 |
| 83 | 503.40 | 1-[1-(4-bromo-3,5-diethoxy-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 4-bromo-3,5-diethoxy-benzaldehyde (intermediate B12) | [M + H]+ 505.3 |
| 84 | 489.58 | 1-[1-(3,5-diethoxy-4-pyrrol-1-yl-benzyl)-piperidin-4-yl]-1H-benzotriazole-5-carboxylic acid | 1-piperidin-4-yl-1H-benzotriazole-5-carboxylic acid allyl ester dihydrochloride (intermediate A4) and 3,5-diethoxy-4-pyrrol-1-yl-benzaldehyde (intermediate B14) | [M + H]+ 490.4 |
| 85 | 366.46 | 1-[1-(3-ethoxy-4-methyl-benzyl)-piperidin-4-yl]-1,5-dihydro-imidazo[4,5-c]pyridin-4-one | 1-piperidin-4-yl-1,5-dihydro-imidazo[4,5-c]pyridin-4-one dihydrochloride (intermediate A5) and 3-ethoxy-4-methyl-benzaldehyde (intermediate B19) | [M + H]+ 367.3 |
| 86 | 386.88 | 1-[1-(4-chloro-3-ethoxy-benzyl)-piperidin-4-yl]-1,5-dihydro-imidazo[4,5-c]pyridin-4-one | 1-piperidin-4-yl-1,5-dihydro-imidazo[4,5-c]pyridin-4-one dihydrochloride (intermediate A5) and 4-chloro-3-ethoxy-benzaldehyde (intermediate B2) | [M + H]+ 387.3 |
| 87 | 382.46 | 1-[1-(3-ethoxy-4-methoxy-benzyl)-piperidin-4-yl]-1,5-dihydro-imidazo[4,5-c]pyridin-4-one | 1-piperidin-4-yl-1,5-dihydro-imidazo[4,5-c]pyridin-4-one dihydrochloride (intermediate A5) and 3-ethoxy-4-methoxy-benzaldehyde (commercially available) | [M + H]+ 383.3 |
| 88 | 410.52 | 1-[1-(3-ethoxy-4-isopropoxy-benzyl)-piperidin-4-yl]-1,5-dihydro-imidazo[4,5-c]pyridin-4-one | 1-piperidin-4-yl-1,5-dihydro-imidazo[4,5-c]pyridin-4-one dihydrochloride (intermediate A5) and 3-ethoxy-4-isopropoxy-benzaldehyde (commercially available) | [M + H]+ 411.4 |
| 89 | 424.54 | 1-[1-(3-ethoxy-4-isobutoxy-benzyl)-piperidin-4-yl]-1,5-dihydro-imidazo[4,5- | 1-piperidin-4-yl-1,5-dihydro-imidazo[4,5-c]pyridin-4-one dihydrochloride (intermediate A5) and | [M + H]+ 425.3 |

TABLE 1-continued

| No | MW | Compound Name | Starting Materials | ISP [M + H]+ |
|---|---|---|---|---|
| | | c]pyridin-4-one | 3-ethoxy-4-isobutoxy-benzaldehyde (commercially available) | |
| 90 | 438.57 | 1-{1-[3-ethoxy-4-(1-ethyl-propoxy)-benzyl]-piperidin-4-yl}-1,5-dihydro-imidazo[4,5-c]pyridin-4-one | 1-piperidin-4-yl-1,5-dihydro-imidazo[4,5-c]pyridin-4-one dihydrochloride (intermediate A5) and 3-ethoxy-4-(1-ethyl-propoxy)-benzaldehyde (intermediate B3) | [M + H]+ 439.4 |
| 91 | 436.56 | 1-[1-(4-cyclopentyloxy-3-ethoxy-benzyl)-piperidin-4-yl]-1,5-dihydro-imidazo[4,5-c]pyridin-4-one | 1-piperidin-4-yl-1,5-dihydro-imidazo[4,5-c]pyridin-4-one dihydrochloride (intermediate A5) and 4-cyclopentyloxy-3-ethoxy-benzaldehyde (commercially available) | [M + H]+ 437.4 |
| 92 | 458.56 | 1-[1-(4-benzyloxy-3-ethoxy-benzyl)-piperidin-4-yl]-1,5-dihydro-imidazo[4,5-c]pyridin-4-one | 1-piperidin-4-yl-1,5-dihydro-imidazo[4,5-c]pyridin-4-one dihydrochloride (intermediate A5) and 4-benzyloxy-3-ethoxy-benzaldehyde (commercially available) | [M + H]+ 459.4 |
| 93 | 418.44 | 1-[1-(4-difluoromethoxy-3-ethoxy-benzyl)-piperidin-4-yl]-1,5-dihydro-imidazo[4,5-c]pyridin-4-one | 1-piperidin-4-yl-1,5-dihydro-imidazo[4,5-c]pyridin-4-one dihydrochloride (intermediate A5) and 4-difluoromethoxy-3-ethoxy-benzaldehyde (commercially available) | [M + H]+ 419.2 |
| 94 | 410.52 | 1-[1-(3-isobutoxy-4-methoxy-benzyl)-piperidin-4-yl]-1,5-dihydro-imidazo[4,5-c]pyridin-4-one | 1-piperidin-4-yl-1,5-dihydro-imidazo[4,5-c]pyridin-4-one dihydrochloride (intermediate A5) and 3-isobutoxy-4-methoxy-benzaldehyde (intermediate B5) | [M + H]+ 411.4 |
| 95 | 422.53 | 1-[1-(3-cyclopentyloxy-4-methoxy-benzyl)-piperidin-4-yl]-1,5-dihydro-imidazo[4,5-c]pyridin-4-one | 1-piperidin-4-yl-1,5-dihydro-imidazo[4,5-c]pyridin-4-one dihydrochloride (intermediate A5) and 3-cyclopentyloxy-4-methoxy-benzaldehyde (commercially available) | [M + H]+ 423.2 |
| 96 | 434.54 | 1-[1-(8-ethoxy-2,2-dimethyl-2H-chromen-6-ylmethyl)-piperidin-4-yl]-1,5-dihydro-imidazo[4,5-c]pyridin-4-one | 1-piperidin-4-yl-1,5-dihydro-imidazo[4,5-c]pyridin-4-one dihydrochloride (intermediate A5) and 8-ethoxy-2,2-dimethyl-2H-chromene-6-carbaldehyde (intermediate B6) | [M + H]+ 435.4 |
| 97 | 414.48 | 1-[1-(3,5-diethoxy-4-fluoro-benzyl)-piperidin-4-yl]-1,5-dihydro-imidazo[4,5-c]pyridin-4-one | 1-piperidin-4-yl-1,5-dihydro-imidazo[4,5-c]pyridin-4-one dihydrochloride (intermediate A5) and 3,5-diethoxy-4-fluoro-benzaldehyde (intermediate B10) | [M + H]+ 415.4 |
| 98 | 430.94 | 1-[1-(4-chloro-3,5-diethoxy-benzyl)-piperidin-4-yl]-1,5-dihydro-imidazo[4,5-c]pyridin-4-one | 1-piperidin-4-yl-1,5-dihydro-imidazo[4,5-c]pyridin-4-one dihydrochloride (intermediate A5) and 4-chloro-3,5-diethoxy-benzaldehyde (intermediate B11) | [M + H]+ 431.4 |
| 99 | 475.39 | 1-[1-(4-bromo-3,5-diethoxy-benzyl)-piperidin-4-yl]-1,5-dihydro-imidazo[4,5-c]pyridin-4-one | 1-piperidin-4-yl-1,5-dihydro-imidazo[4,5-c]pyridin-4-one dihydrochloride (intermediate A5) and 4-bromo-3,5-diethoxy-benzaldehyde (intermediate B12) | [M + H]+ 477.3 |
| 100 | 411.51 | 1-[1-(4-amino-3,5-diethoxy-benzyl)-piperidin-4-yl]-1,5-dihydro-imidazo[4,5-c]pyridin-4-one | 1-piperidin-4-yl-1,5-dihydro-imidazo[4,5-c]pyridin-4-one dihydrochloride (intermediate A5) and 4-amino-3,5-diethoxy- | [M + H]+ 412.3 |

TABLE 1-continued

| No | MW | Compound Name | Starting Materials | ISP [M + H]+ |
|---|---|---|---|---|
| 101 | 461.57 | 1-[1-(3,5-diethoxy-4-pyrrol-1-yl-benzyl)-piperidin-4-yl]-1,5-dihydro-imidazo[4,5-c]pyridin-4-one | benzaldehyde (intermediate B13) 1-piperidin-4-yl-1,5-dihydro-imidazo[4,5-c]pyridin-4-one dihydrochloride (intermediate A5) and 3,5-diethoxy-4-pyrrol-1-yl benzaldehyde (intermediate B14) | [M + H]+ 462.4 |
| 102 | 490.58 | 1-[1-(2,6-diethoxy-4'-fluoro-biphenyl-4-ylmethyl)-piperidin-4-yl]-1,5-dihydro-imidazo[4,5-c]pyridin-4-one | 1-piperidin-4-yl-1,5-dihydro-imidazo[4,5-c]pyridin-4-one dihydrochloride (intermediate A5) and 2,6-diethoxy-4'-fluoro-biphenyl-4-carbaldehyde (intermediate B15) | [M + H]+ 491.4 |

Example 103

2-[1-(3-Ethoxy-4-methyl-benzyl)-piperidin-4-yl]-2,3-dihydro-isoindol-1-one

Step 1: 4-(1-Oxo-1,3-dihydro-isoindol-2-yl)-piperidine-1-carboxylic acid tert-butyl ester To a solution of 2-bromomethyl-benzoic acid methyl ester (1.50 g, 6.55 mmol, 1.0 equiv; [CAS RN 2417-73-4]) in methanol (12.5 mL) and triethylamine (1.10 mL) was added 4-amino-piperidine-1-carboxylic acid tert-butyl ester (1.38 g, 6.88 mmol, 1.05 equiv; commercially available) and the reaction stirred at rt overnight. The reaction mixture was poured on crashed ice, extracted with ethyl acetate, the combined organic phases washed with water and a sat. solution of NaCl, dried over MgSO$_4$ and concentrated by evaporation under reduced pressure. The crude material was purified with silica column chromatography eluting with hexane/ethyl acetate (1:1) followed by crystallization from hexane/ethyl acetate to obtain 1.12 g (54%) of the title compound as white crystals. MS (ISP): 261.0 [M-tert-Bu+H]+.

Step 2: 2-Piperidin-4-yl-2,3-dihydro-isoindol-1-one trifluoroacetate (Intermediate A6)

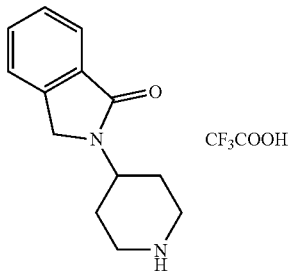

CF$_3$COOH

To a solution of 4-(1-oxo-1,3-dihydro-isoindol-2-yl)-piperidine-1-carboxylic acid tert-butyl ester (0.50 g, 1.58 mmol) in dichloromethane (15 mL) was added trifluoro-acetic acid (3.0 mL) and the reaction mixture stirred at ambient temperature during 4 h. The solvent was removed under reduced pressure and the crude product (0.710 g) used in the consecutive step without further purification assuming quantitative deprotection and formation of the trifluoroacetate salt. MS (ISP): 217.4 [M+H]+.

Step 3: 2-[1-(3-Ethoxy-4-methyl-benzyl)-piperidin-4-yl]-2,3-dihydro-isoindol-1-one To a solution of 2-piperidin-4-yl-2,3-dihydro-isoindol-1-one trifluoroacetate (164.0 mg, 0.27 mmol, 1.0 equiv; 36% purity according to mass balance in preceeding step) in isopropanol (3.4 mL) was added 3-ethoxy-4-methyl-benzaldehyde (44.8 mg, 0.27 mmol, 1.0 equiv; intermediate B19), titanium tetra-isopropoxide (232.8 mg, 0.82 mmol, 3.0 equiv) and sodium cyanoborohydride (34.3 mg, 0.55 mmol, 2.0 equiv). The reaction mixture was allowed to react overnight and then poured directly onto a silica column. Eluting with ethyl acetate/triethylamine (98:2) yielded 29.0 mg (29%) of the title compound as white crystals. MS (ISP): 365.1 [M+H]+.

The dihydro-isoindolone intermediate A7 was prepared as described below. Synthesis of Dihydro-isoindolone Intermediate A7 to be used in Table 2

Intermediate A7

5-Methoxy-2-piperidin-4-yl-2,3-dihydro-isoindol-1-one trifluoroacetate

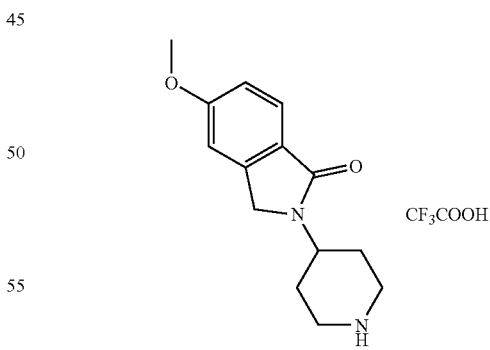

Step 1: 2-Bromomethyl-4-methoxy-benzoic acid methyl ester

To a solution of 4-methoxy-2-methyl-benzoic acid methyl ester (1.47 g, 8.16 mmol, 1.0 equiv; commercially available) in CCl$_4$ (15 mL) was added N-bromosuccinimide (1.60 g, 8.97 mmol, 1.1 equiv) and dibenzoyl peroxide (0.198 g, 0.45 mmol, 0.05 equiv). The mixture was heated to reflux for 1.5 h, when TLC indicated that still some starting material was left.

Therefore, additional N-bromosuccinimide (0.16 g, 0.90 mmol, 0.11 equiv) and dibenzoyl peroxide (0.080 g, 0.41 mmol, 0.18 equiv) was added and heating continued for 1 h. The reaction mixture was cooled down, poured on crashed ice, extracted with ethyl acetate, the combined organic phases washed with a sat. solution of NaCl, dried over $Na_2SO_4$ and concentrated by evaporation under reduced pressure. The crude material was purified with silica column chromatography eluting with hexane/ethyl acetate (95:5) affording 1.43 g (68%) of the title compound as yellow crystals. $^1H$ NMR (300 MHz, $CDCl_3$): δ 3.87 (s, 3H), 3.91 (s, 3H), 4.97 (s, 2H), 6.86 (dd, J=8.7 Hz, J=2.7 Hz, 1H), 6.97 (d, J=2.7 Hz, 1H), 7.99 (d, J=8.7 Hz, 1H).

Step 2: 4-(5-Methoxy-1-oxo-1,3-dihydro-isoindol-2-yl)-piperidine-1-carboxylic acid tert-butyl ester To a solution of 2-bromomethyl-4-methoxy-benzoic acid methyl ester (1.28 g, 4.94 mmol, 1.0 equiv) in methanol (9 mL) and triethylamine (0.83 mL) was added 4-amino-piperidine-1-carboxylic acid tert-butyl ester (1.04 g, 5.19 mmol, 1.05 equiv; commercially available) and the reaction stirred at rt overnight. The reaction mixture was poured on crashed ice/diluted HCl, extracted with ethyl acetate, the combined organic phases washed with a sat. solution of $NaHCO_3$ and water, dried over $Na_2SO_4$ and concentrated by evaporation under reduced pressure. The crude material was purified with silica column chromatography eluting with hexane/ethyl acetate (3:7) yielding 0.84 g (49%) of the title compound as white crystals. MS (ISP): 347.3 $[M+H]^+$.

Step 3: 5-Methoxy-2-piperidin-4-yl-2,3-dihydro-isoindol-1-one trifluoroacetate

To a solution of 4-(5-methoxy-1-oxo-1,3-dihydro-isoindol-2-yl)-piperidine-1-carboxylic acid tert-butyl ester (0.84 g, 2.44 mmol) in dichloromethane (8.5 mL) was added trifluoro-acetic acid (1.7 mL) and the reaction mixture stirred at rt overnight. The solvent was removed under reduced pressure and the crude product used in the consecutive step without further purification assuming quantitative deprotection and formation of the trifluoroacetate salt. MS (ISP): 247.3 $[M+H]^+$.

Examples 104 to 110

According to the procedure described for the synthesis of example 103/step 3 further dihydro-isoindolone derivatives have been synthesized from 2-piperidin-4-yl-2,3-dihydro-isoindol-1-one trifluoroacetate (intermediate A6) and 5-methoxy-2piperidin-4yl-2,3-dihydro-isoindol-1-one trifluoroacetate (intermediate A7) and the respective benzaldehyde intermediate as indicated in Table 2. The results are compiled in Table 2 and comprise example 104 to example 110.

TABLE 2

| No | MW | Compound Name | Starting Materials | ISP $[M + H]^+$ |
|---|---|---|---|---|
| 104 | 422.57 | 2-[1-(3,5-diisopropoxy-benzyl)-piperidin-4-yl]-2,3-dihydro-isoindol-1-one | 2-piperidin-4-yl-2,3-dihydro-isoindol-1-one trifluoroacetate (intermediate A6) and 3,5-diisopropoxy-benzaldehyde (intermediate B8) | $[M + H]^+$ 423.2 |
| 105 | 412.50 | 2-[1-(3,5-diethoxy-4-fluoro-benzyl)-piperidin-4-yl]-2,3-dihydro-isoindol-1-one | 2-piperidin-4-yl-2,3-dihydro-isoindol-1-one trifluoroacetate (intermediate A6) and 3,5-diethoxy-4-fluoro-benzaldehyde (intermediate B10) | $[M + H]^+$ 413.4 |
| 106 | 444.55 | 2-[1-(2-ethoxy-4'-fluoro-biphenyl-4-ylmethyl)-piperidin-4-yl]-2,3-dihydro-isoindol-1-one | 2-piperidin-4-yl-2,3-dihydro-isoindol-1-one trifluoroacetate (intermediate A6) and 2-ethoxy-4'-fluoro-biphenyl-4-carbaldehyde (intermediate B20) | $[M + H]^+$ 445.2 |
| 107 | 452.59 | 2-[1-(3,5-diisopropoxy-benzyl)-piperidin-4-yl]-5-methoxy-2,3-dihydro-isoindol-1-one | 5-methoxy-2-piperidin-4-yl-2,3-dihydro-isoindol-1-one trifluoroacetate (intermediate A7) and 3,5-diisopropoxy-benzaldehyde (intermediate B8) | $[M + H]^+$ 453.4 |
| 108 | 442.53 | 2-[1-(3,5-diethoxy-4-fluoro-benzyl)-piperidin-4-yl]-5-methoxy-2,3-dihydro-isoindol-1-one | 5-methoxy-2-piperidin-4-yl-2,3-dihydro-isoindol-1-one trifluoroacetate (intermediate A7) and 3,5-diethoxy-4-fluoro-benzaldehyde (intermediate B10) | $[M + H]^+$ 443.1 |
| 109 | 489.61 | 2-[1-(3,5-diethoxy-4-pyrrol-1-yl-benzyl)-piperidin-4-yl]-5-methoxy-2,3-dihydro-isoindol-1-one | 5-methoxy-2-piperidin-4-yl-2,3-dihydro-isoindol-1-one trifluoroacetate (intermediate A7) and 3,5-diethoxy-4-pyrrol-1-yl-benzaldehyde (intermediate B14) | $[M + H]^+$ 490.3 |
| 110 | 474.57 | 2-[1-(2-ethoxy-4'-fluoro-biphenyl-4-ylmethyl)-piperidin-4-yl]-5-methoxy-2,3-dihydro-isoindol-1-one | 5-methoxy-2-piperidin-4-yl-2,3-dihydro-isoindol-1-one trifluoroacetate (intermediate A7) and 2-ethoxy-4'-fluoro-biphenyl-4-carbaldehyde (intermediate B20) | $[M + H]^+$ 475.1 |

Example A

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 mg or 350 mg, respectively. The kernels are lacquered with an aqueous solution/suspension of the above mentioned film coat.

Example B

Capsules containing the following, ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula I | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula I | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

It is to be understood that the invention is not limited to the particular embodiments of the invention described above, as variations of the particular embodiments may be made and still fall within the scope of the appended claims.

What is claimed is:

1. A compound of formula I:

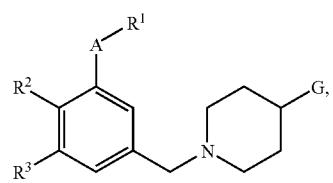

wherein
A is —O—;
$R^1$ is selected from the group consisting of $C_{2-7}$-alkyl, $C_{2-7}$-alkenyl, $C_{3-7}$-alkynyl, $C_{3-7}$-cycloalkyl, halogen-$C_{1-7}$-alkyl, $C_{1-7}$-alkoxy-$C_{1-7}$-alkyl and benzyl;
$R^2$ is selected from the group consisting of hydrogen, $C_{1-7}$-alkyl, hydroxy, $C_{1-7}$-alkoxy, $C_{2-7}$-alkenyloxy, hydroxy-$C_{1-7}$-alkoxy, $C_{1-7}$-alkoxy-$C_{1-7}$-alkoxy, —O-benzyl, —O—$C_{3-7}$-cycloalkyl, unsubstituted phenyl or phenyl substituted by one to three groups independently selected from $C_{1-7}$-alkyl, halogen and $C_{1-7}$-alkoxy, halogen, halogen-$C_{1-7}$-alkyl, halogen-$C_{1-7}$-alkoxy, amino, pyrrolyl, cyclopentyl, imidazolyl, and
—C(O)OR$^4$, wherein R$^4$ is $C_{1-7}$-alkyl;

R$^3$ is hydrogen or $C_{1-7}$-alkoxy;

G is selected from the groups

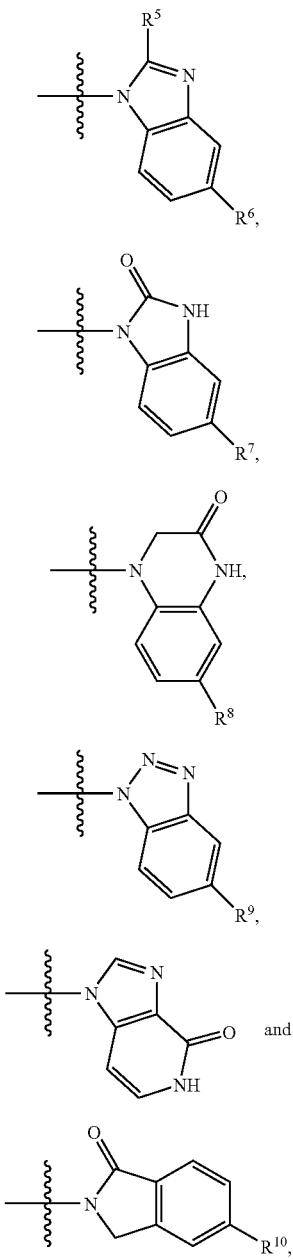

wherein

R$^5$ is hydrogen or $C_{1-7}$-alkyl;

R$^6$, R$^7$, R$^8$ and R$^9$ are —COOH;

R$^{10}$ is hydrogen or $C_{1-7}$-alkoxy;

or pharmaceutically acceptable salts thereof.

2. The compound according to claim 1, wherein R$^1$ is selected from the group consisting of $C_{2-7}$-alkyl, $C_{2-7}$-alkenyl, $C_{3-7}$-alkynyl, $C_{3-7}$-cycloalkyl and halogen-$C_{1-7}$-alkyl.

3. The compound according to claim 1, wherein R$^2$ is selected from the group consisting of ethyl, propyl, isopropyl, 2-fluoroethyl, butyl and isobutyl.

4. The compound according to claim 1, wherein R$^2$ is selected from the group consisting of
hydrogen, $C_{1-7}$-alkyl, hydroxy, $C_{1-7}$-alkoxy, $C_{2-7}$-alkenyloxy,
—O-benzyl, —O—$C_{3-7}$-cycloalkyl,
unsubstituted phenyl or phenyl substituted by one to three groups independently selected from $C_{1-7}$-alkyl, halogen and $C_{1-7}$-alkoxy,
halogen, halogen-$C_{1-7}$-alkoxy, amino, pyrrolyl, imidazolyl and
—C(O)OR$^4$, wherein R$^4$ is $C_{1-7}$-alkyl.

5. The compound according to claim 1, wherein R$^2$ is selected from the group consisting of hydrogen, $C_{1-7}$-alkoxy, halogen, halogen-$C_{1-7}$-alkoxy, pyrrolyl, phenyl substituted by halogen and —C(O)OR$^4$, wherein R$^4$ is $C_{1-7}$-alkyl.

6. The compound according to claim 1, wherein R$^2$ is halogen.

7. The compound according to claim 1, wherein R$^2$ is hydrogen or $C_{1-7}$-alkoxy.

8. The comound according to claim 1, wherein G is

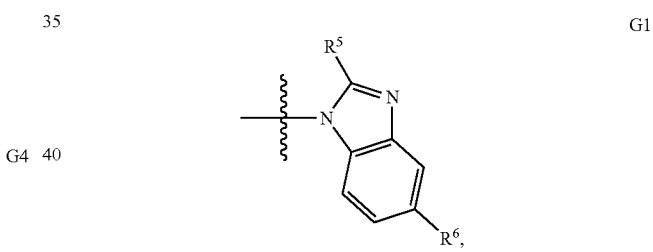

and wherein R$^5$ is hydrogen or $C_{1-7}$-alkyl and R$^6$ is —COOH.

9. The compound according to claim 8, wherein R$^5$ is methyl.

10. The compound according to claim 1, herein G is

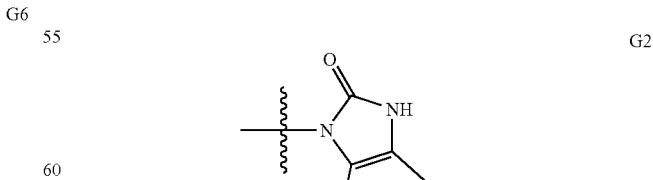

and wherein R$^7$ is —COOH.

11. The compound according to claim 1, wherein G is

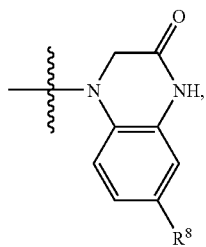

and wherein R⁸ is —COOH.

12. The compound according to claim 1, wherein G is

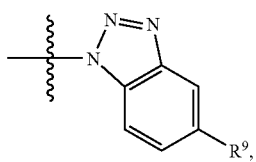

and wherein R⁹ is —COOH.

13. The compound according to claim 1, wherein G is

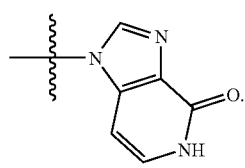

14. The compound according to claim 1, wherein G is

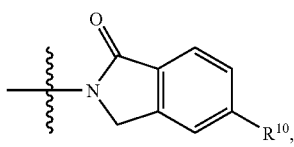

and wherein $R^{10}$ is hydrogen or $C_{1-7}$-alkoxy.

15. The compound according to claim 14, wherein $R^{10}$ is methoxy.

16. The compound according to claim 1, selected from the group consisting of
1-[1-(3-ethoxy-4-fluoro-benzyl)piperidin-4-yl]-2-methyl-1H-benzoimidazole-5-carboxylic acid,
1-[1-(4-chloro-3-ethoxy-benzyl)-piperidin-4-yl]-2-methyl-1H-benzoimidazole-5-carboxylic acid,
1-[1-(4-allyloxy-3-ethoxy-benzyl)-piperidin-4-yl]-2-methyl-1H-benzoimidazole-5-carboxylic acid,
1-[1-(3-ethoxy-4-isopropoxy-benzyl)piperidin-4-yl]-2-methyl-1H-benzoimidazole-5-carboxylic acid,
1-(3-ethoxy-4-isobutoxy-benzyl)-piperidin-4-yl]-2-methyl-1H-benzoimidazole-5-carboxylic acid,
1-{1-[3-ethoxy-4-(1-ethyl-propoxy)-benzy]-piperidin-4-yl}-2-methyl-1H-benzoimidazole-5-carboxylic acid,
1-[1-(4-cyclopentyloxy-3-ethoxy-benzyl)-piperidin-4-yl]-2-methyl-1H-benzoimidazole-5-carboxylic acid,
1-[1-(4-benzyloxy-3-ethoxy-benzyl)piperidin-4-yl]-2-methyl-1H-benzoimidazole-5-carboxylic acid,
1-[1-(4-difluoromethoxy-3-ethoxy-benzyl)-piperidin-4-yl]-2-methyl-1H-benzoimidazole-5-carboxylic acid,
1-[1-(3-isopropoxy-4-methoxy-benzyl)piperidin-4-yl]-2-methyl-1H-benzoimidazole-5-carboxylic acid,
1-{1-[3-(2-fluoro-ethoxy)-4-methoxy-benzy]-piperidin-4-yl}-2-methyl-1H-benzoimidazole-5-carboxylic acid,
1-[1-(3-isobutoxy-4-methoxy-benzyl)-piperidin-4-yl]-2methyl-1H-benzoimidazole-5-carboxylic acid,
1-[1-(3-cyclopentyloxy-4-methoxy-benzyl)-piperidin-4-yl]-2-methyl-1H-benzoimidazole-5-carboxylic acid,
1-[1-(3,5-diethoxy-benzyl)-piperidin-4-yl]-2-methyl-1H-benzoimidazole-5-carboxylic acid,
1-[1-(3,5-diisopropoxy-benzyl)-piperidin-4-yl]-2-methyl-1H-benzoimidazole-5-carboxylic acid,
1-[1-(3,5-diethoxy-4-fluoro-benzyl)-piperidin-4-yl]-2-methyl-1H-benzoimidazole-5-carboxylic acid,
1-[1-(4-chloro-3,5-diethoxy-benzyl)-piperidin-4-yl]-2-methyl-1H-benzoimidazole-5-carboxylic acid,
1-81-(4-bromo-3,5-diethoxy-benzyl)-piperidin-4-yl]-2-methyl-1H-benzoimidazole-5-carboxylic acid,
1-[1-(4-amino-3,5-diethoxy-benzyl)-piperidin-4-yl]-2-methyl-1H-benzoimidazole-5-carboxylic acid,
1-[1-(3,5-diethoxy-4-pyrrol-1-yl-benzyl)-piperidin-4-yl1]-2-methyl-1H-benzoimidazole-5-carboxylic acid,
1-[1-(3,5-diethoxy-4-ethoxycarbonyl-benzyl)-piperidin-4-yl]-2-methyl-1H-benzoimidazole-5-carboxylic acid,
1-[1-(2,6-diethoxy-4'-fluoro-biphenyl-4-ylmethyl)-piperidin-4-yl]-2-methyl-1H-benzoimidazole-5-carboxylic acid,
1-[1-(3-ethoxy-4-fluoro-benzyl)-piperidin-4-yl -2-oxo-2,3-dihydro-1H-benzoimidazole-5-carboxylic acid,
1-[1-(4-chloro-3-ethoxy-benzyl)-piperidin-4-yl ]-2-oxo-2,3-dihydro-1H-benzoimidazole-5-carboxylic acid,
1-[1-(3-ethoxy-4-hydroxy-benzyl)-piperidin-4-yl ]-2-oxo-2,3-dihydro-1H-benzoimidazole-5-carboxylic acid,
1-[1-(3-ethoxy-4-methoxy-benzyl)-piperidin-4-yl -2-oxo-2,3-dihydro-1H-benzoimidazole-5-carboxylic acid, 1-[1-(3,4-diethoxy-benzyl)-piperidin-4-yl -2-oxo-2,3-dihydro-1H-benzoimidazole-5-carboxylic acid,
1-[1-(4-allyloxy-3-ethoxy-benzyl)-piperidin-4-yl]2-oxo-2,3-dihydro-1H-benzoimidazole-5-carboxylic acid,
1-[1-(3-ethoxy-4-isopropoxy-benzyl)-piperidin-4-yl]-2-oxo-2,3-dihydro-1H -benzoimidazole-5-carboxylic acid,
1-[1-(3-ethoxy-4-isobutoxy-benzyl)-piperidin-4-yl]-2-oxo- 2,3-dihydro-1H-benzoimidazole -5-carboxylic acid,
1-{1-[3-ethoxy-4-(1-ethyl-propoxy)-benzy]-piperidin-4-yl }-2-oxo- 2,3-dihydro-1H -benzoimidazole-5-carboxylic acid,
1-[1-(4-cyclopentyloxy-3-ethoxy-benzyl)-piperidin-4-yl ]-2-oxo-2,3-dihydro-1H -benzoimidazole-5-carboxylic acid,
1-[1-(4-benzyloxy-3-ethoxy-benzyl)-piperidin-4-yl ]-2-oxo-2,3-dihydro-1H -benzoimidazole-5-carboxylic acid,
1-[1-(4-difluoromethoxy-3-ethoxy-benzyl)-piperidin-4-yl ]-2-oxo-2,3-dihydro-1H -benzoimidazole-5-carboxylic acid, 1-[1-(4-methoxy-3-propoxy-benzyl)-piperidin-4-yl ]-2-oxo2,3-dihydro-1H -benzoimidazole-5-carboxylic acid, 1-{1-[3-(2-fluoro-ethoxy)-4-methoxy-benzyl]-piperidin-4-yl}-2-oxo-2,3-dihydro-1H-benzoimidazole-5-carboxylic acid,
1-[1-(3-butoxy-4-methoxy-benzyl)-piperidin-4-yl]-oxo-2,3-dihydro-1H-benzoimidazole-5-carboxylic acid,
1-[1-(3-isobutoxy-4-methoxy-benzyl)-piperidin-4-yl]-2-oxo-2,3-dihydro-1H-benzoimidazole-5-carboxylic acid, 1-[1-(3-cyclopentyloxy-4-methoxy-benzyl)-piperidin-4-yl]-2-oxo-2,3-dihydro-1H-benzoimidazole-5-carboxylic acid,
1-[1-(3,5-diethoxy-benzyl)-piperidin-4-yl]-2-oxo-2,3-dihydro-1H-benzoimidazole-5-carboxylic acid,
1-[1-(3,5-diisopropoxy-benzyl)-piperidin-4-yl]-2-oxo-2,3-dihydro-1H-benzoimidazole-5-carboxylic acid,
1-[1-(3,5-diethoxy-4-ethoxycarbonyl-benzyl)-piperidin-4-yl]-2-oxo-2,3-dihydro-1H-benzoimidazole-5-carboxylic acid, 1-[1-(3,5-diethoxy-4-fluoro-benzyl)-piperidin-4-yl]-2-oxo-2,3-dihydro-1H-benzoimidazole-5-carboxylic acid,
1-[1-(4-chloro-3,5-diethoxy-benzyl)-piperidin-4-yl]-2-oxo-2,3-dihydro-1H-benzoimidazole-5-carboxylic acid, 1[1-(4-bromo-3,5-diethoxy-benzyl)-piperidin-4-yl]-2-oxo-2,3-dihydro-1H-benzoimidazole-5-carboxylic acid,
1-[1-(4-amino-3,5-diethoxy-benzyl)-piperidin-4-yl]-2-oxo-2,3-dihydro-1H-benzoimidazole-5-carboxylic acid,
1-[1-(3,5-diethoxy-4-pyrrol-1-yl-benzyl)-piperidin-4-yl]-2-oxo-2,3-dihydro-1H-benzoimidazole-5-carboxylic acid, 1-[1-(4-chloro-3-ethoxy-benzyl)-piperidin-4-yl]-3-oxo-1,2,3,4-tetrahydro-quinoxaline-6-carboxylic acid, 1-[1-(4-difluoromethoxy-3-ethoxy-benzyl)-piperidin-4-yl]-3-oxo-1,2,3,4-tetrahydro-quinoxaline-6-carboxylic acid,
1-[1-(3-cyclopentyloxy-4-methoxy-benzyl)-piperidin-4-yl]-3-oxo-1,2,3,4-tetrahydro-quinoxaline-6-carboxylic acid,
1-[1-(3,5-diisopropoxy-benzyl)-piperidin-4-yl]-3-oxo-1,2,3,4-tetrahydro-quinoxaline-6-carboxylic acid,
1-[1-(3,5-diethoxy-4-ethoxycarbonyl-benzyl)-piperidin-4-yl]-3-oxo-1,2,3,4-tetrahydro-quinoxaline-6-carboxylic acid,
1-[1-(3,5-diethoxy-4-fluoro-benzyl)-piperidin-4-yl]-3-oxo-1,2,3,4-tetrahydro-quinoxaline-6-carboxylic acid,
1[1-(4-chloro-3,5-diethoxy-benzyl)-piperidin-4-yl]-3-oxo-1,2,3,4-tetrahydro-quinoxaline-6-carboxylic acid,
1-[1-(4-bromo-3,5-diethoxy-benzyl)-piperidin-4-yl]-3-oxo-1,2,3,4-tetrahydro-quinoxaline-6-carboxylic acid,
1-[1-(3,5-diethoxy-4-pyrrol-1-yl-benzyl)-piperidin-4-yl]-3-oxo-1,2,3,4-tetrahydro-quinoxaline-6-carboxylic acid,
1[1-(2,6-diethoxy-4'-fluoro-biphenyl-4-ylmethyl)-piperidin-4-yl]-3-oxo-1,2,3,4-tetrahydro-quinoxaline-6-carboxylic acid,
1-[1-(3-ethoxy-4-fluoro-benzyl)piperidin-4-yl]-1H-benzotriazole-5-carboxylic acid,
1-[1-(4-chloro-3-ethoxy-benzyl)piperidin-4-yl]-1H-benzotriazole-5-carboxylic acid,
1-[1-(3-ethoxy-4-hydroxy-benzyl)piperidin-4-yl]-1H-benzotriazole-5-carboxylic acid,
1-[1-(3-ethoxy-4-methoxy-benzyl)piperidin-4-yl]-1H-benzotriazole-5-carboxylic acid,
1-[1-(3,4-diethoxy-benzyl)piperidin-4-yl]-1H-benzotriazole-5-carboxylic acid,
1-[1-(4-allyloxy-3-ethoxy-benzyl)piperidin-4-yl]-1H-benzotriazole-5-carboxylic acid,
1-[1-(3-ethoxy-4-isopropoxy-benzyl)piperidin-4-yl]-1H-benzotriazole-5-carboxylic acid, 1-[1-(3-ethoxy-4-isobutoxy-benzyl)piperidin-4-yl]-1H-benzotriazole-5-carboxylic acid,
1-{1-[3-ethoxy-4-(1-ethyl-propoxy)-benzyl]-piperidin-4-yl}-1H-benzotriazole-5-carboxylic acid,
1-[1-(4-cyclopentyloxy-3-ethoxy-benzyl)piperidin-4-yl]-1H-benzotriazole-5-carboxylic acid,
1-[1-(4-benzyloxy-3-ethoxy-benzyl)-piperidin-4-yl]-1H-benzotriazole-5-carboxylic acid,
1-[1-(4-difluoromethoxy-3-ethoxy-benzyl)-piperidin-4-yl]-1H-benzotriazole-5-carboxylic acid,
1-[1-(4-methoxy-3-propoxy-benzyl)piperidin-4-yl]-1H-benzotriazole-5-carboxylic acid,
1-[1-(3-isopropoxy-4-methoxy-benzyl)piperidin-4-yl]-1H-benzotriazole-5-carboxylic acid,
1-[1-(3-allyloxy-4-methoxy-benzyl)piperidin-4-yl]-1H-benzotriazole-5-carboxylic acid,
1-[1-(4-methoxy-3-prop-2-ynyloxy-benzyl)piperidin-4-yl]-1H-benzotriazole-5-carboxylic acid,
1-[1-(3-butoxy-4-methoxy-benzyl)piperidin-4-yl]-1H-benzotriazole-5-carboxylic acid,
1-[1-(3-isobutoxy-4-methoxy-benzyl)piperidin-4-yl]-1H-benzotriazole-5-carboxylic acid,
1-[1-(3-cyclopentyloxy-4-methoxy-benzyl)piperidin-4-yl]-1H-benzotriazole-5-carboxylic acid,
1-[1-(3,5-diethoxy-benzyl)-piperidin-4-yl]-1H-benzotriazole-5-carboxylic acid,
1-[1-(3,5-diethoxy-4-fluoro-benzyl)-piperidin-4-yl]-1H-benzotriazole-5-carboxylic acid,
1-[1-(4-chloro-3,5-diethoxy-benzyl)-piperidin-4-yl]-1H-benzotriazole-5-carboxylic acid,
1-[1-(4-bromo-3,5-diethoxy-benzyl)-piperidin-4-yl]-1H-benzotriazole-5-carboxylic acid,
1-[1-(3,5-diethoxy-4-pyrrol-1-yl-benzyl)-piperidin-4-yl]-1H-benzotriazole-5-carboxylic acid,
1-[1-(3-ethoxy-4-methyl-benzyl)-piperidin-4-yl]-1,5-dihydro-imidazo[4,5-c]pyridin-4-one, 1-[1(4-chloro-3-ethoxy-benzyl)-piperidin-4-yl]-1,5-dihydro-imidazo[4,5-c]pyridin-4-one,
1-[1-(3-ethoxy-4-methoxy-benzyl)-piperidin-4-yl]-1,5-dihydro-imidazo[4,5-c]pyridin-4-one,
1-[1-(3-ethoxy-4-isopropoxy-benzyl)-piperidin-4-yl]-1,5-dihydro-imidazo[4,5-c]pyridin-4-one,
1-[1(3-ethoxy-4-isobutoxy-benzyl)-piperidin-4-yl]-1,5-dihydro-imidazo[4,5-c]pyridin-4-one,
1-{1-[3-ethoxy-4-(1-ethyl-propoxy)-benzyl]-piperidin-4-yl}-1,5-dihydro-imidazo[4,5-c]pyridin-4-one,
1-[1-(4-cyclopentyloxy-3-ethoxy-benzyl)-piperidin-4-yl]-1,5-dihydro-imidazo[4,5-c]pyridin-4-one,
1-[1-(4-benzyloxy-3-ethoxy-benzyl)-piperidin-4-yl]-1,5-dihydro-imidazo[4,5-c]pyridin-4-one,
1-[1-(4-difluoromethoxy-3-ethoxy-benzyl)-piperidin-4-yl]-1,5-dihydro-imidazo[4,5-c]pyridin-4-one,
1-[1-(3-isobutoxy-4-methoxy-benzyl)-piperidin-4-yl]-1,5-dihydro-imidazo[4,5-c]pyridin-4-one,
1-[1-(3-cyclopentyloxy-4-methoxy-benzyl)-piperidin-4-yl]-1,5-dihydro-imidazo[4,5-c]pyridin-4-one,
1-[1(3,5-diethoxy-4-fluoro-benzyl)-piperidin-4-yl]-1,5-dihydro-imidazo[4,5-c]pyridin-4-one,
1-[1(4-chloro-3,5-diethoxy-benzyl)-piperidin-4-yl]-1,5-dihydro-imidazo[4,5-c]pyridin-4-one,
1-[1-(4-bromo-3,5-diethoxy-benzyl)-piperidin-4-yl]-1,5-dihydro-imidazo[4,5-c]pyridin-4-one,
1-[1(4-amino-3,5-diethoxy-benzyl)-piperidin-4-yl]-1,5-dihydro-imidazo[4,5-c]pyridin-4-one, 1-[1-(3,5-diethoxy-4-pyrrol-1-yl-benzyl)-piperidin-4-yl]-1,5-dihydro-imidazo[4,5-c]pyridin-4-one,
1-[1(2,6-diethoxy-4'-fluoro-biphenyl-4-ylmethyl)-piperidin-4-yl]-1,5-dihydro-imidazo[4,5-c ]pyridin-4-one,
2-[1(3-ethoxy-4-methyl-benzyl)-piperidin-4-yl]-2,3-dihydro-isoindol-1-one,
2-[1-(3,5-diisopropoxy-benzyl)-piperidin-4-yl]-2,3-dihydro-isoindol-1-one,
2-[1-(3,5-diethoxy-4-fluoro-benzyl)-piperidin-4-yl]-2,3-dihydro-isoindol-1-one,
2-[1-(2-ethoxy-4'-fluoro-biphenyl-4-ylmethyl)-piperidin-4-yl]-2,3-dihydro-isoindol-1-one,
2-[1-(3,5-diisopropoxy-benzyl)-piperidin-4-yl]-5-methoxy-2,3-dihydro-isoindol-1-one,
2-[(3,5-diethoxy-4-fluoro-benzyl)-piperidin-4-yl]-5-methoxy-2,3-dihydro-isoindol-1-one,
2-[1-(3,5-diethoxy-4-pyrrol-1-yl-benzyl)-piperidin-4-yl]-5-methoxy-2,3-dihydro-isoindol-1-one,
2-[1-(2-ethoxy-4'-fluoro-biphenyl-4-ylmethyl)-piperidin-4-yl]-5-methoxy-2,3-dihydro-isoindol-1-one, or pharmaceutically acceptable salts thereof.

17. The compound according to claim 1, selected from the group consisting of:
1-[1-(4-chloro-3-ethoxy-benzyl)piperidin-4-yl]-2-methyl-1H-benzoimidazole-5-carboxylic acid,
1-{1-[3-ethoxy-4-(1-ethyl-propoxy)-benzyl]-piperidin-4-yl}-2-methyl-1H-benzoimidazole-5-carboxylic acid,
1-[1-(3,5-diisopropoxy-benzyl)-piperidin-4-yl]-2-methyl-1H-benzoimidazole-5-carboxylic acid,
1-[1-(3,5-diethoxy-4-fluoro-benzyl)-piperidin-4-yl]-2-methyl-1H-benzoimidazole-5-carboxylic acid,
1-[1-(4-chloro-3,5-diethoxy-benzyl)-piperidin-4-yl]-2-methyl-1H-benzoimidazole-5-carboxylic acid,
1-[1-(4-bromo-3,5-diethoxy-benzyl)-piperidin-4-yl]-2-methyl-1H-benzoimidazole-5-carboxylic acid,
1-[1-(3,5-diethoxy-4-pyrrol-1-yl-benzyl)-piperidin-4-yl]-2-methy-1-1H-benzoimidazole-5-carboxylic acid,
1-[1-(3,5-diethoxy-4-ethoxycarbonyl-benzyl)-piperidin-4-yl]-2-methyl-1H -benzoimidazole-5-carboxylic acid,
1-[1-(2,6-diethoxy-4'-fluoro-biphenyl-4-ylmethyl)-piperidin-4-yl]-2-methyl-1H -benzoimidazole-5-carboxylic acid,
1-[1-(4-chloro-3-ethoxy-benzyl)-piperidin-4-yl]-2-oxo-2,3-dihydro-1H-benzoimidazole-5-carboxylic acid,
1-[1-(4-difluoromethoxy-3-ethoxy-benzyl)-piperidin-4-yl]-2-oxo-2,3-dihydro-1H -benzoimidazole-5-carboxylic acid,
1-[1-(3,5-diisopropoxy-benzyl)-piperidin-4-yl]-2-oxo-2,3-dihydro-1H-benzoimidazole-5-carboxylic acid,
1-[1-(3,5-diethoxy-4-fluoro-benzyl)-piperidin-4-yl]-2-oxo-2,3-dihydro-1H-benzoimidazole-5-carboxylic acid,
1-[1-(4-chloro-3,5-diethoxy-benzyl)-piperidin-4-yl]-2-oxo-2,3-dihydro-1H -benzoimidazole-5-carboxylic acid,
1-[1-(4-bromo-3,5-diethoxy-benzyl)-piperidin-4-yl]-2-oxo-2,3-dihydro-1H -benzoimidazole-5-carboxylic acid,
1-[1-(3,5-diethoxy-4-pyrrol-1-yl-benzyl)-piperidin-4-yl]-2-oxo-2,3-dihydro-1H -benzoimidazole-5-carboxylic acid,
1-[1(4-bromo-3,5-diethoxy-benzyl)-piperidin-4-yl]-3-oxo-1,2,3,4-tetrahydro-quinoxaline-6-carboxylic acid,
1-[1-(3,5-diethoxy-4-pyrrol-1-yl-benzyl)-piperidin-4-yl]-3-oxo-1,2,3,4-tetrahydro-quinoxaline-6-carboxylic acid,
1-[1(2,6-diethoxy-4'-fluoro-biphenyl-4-ylmethyl)-piperidin-4-yl]-3-oxo-1,2,3,4-tetrahydro-quinoxaline-6-carboxylic acid,
1-[1-(3-ethoxy-4-fluoro-benzyl)piperidin-4-yl]-1H-benzotriazole-5-carboxylic acid,
1-[1-(4-chloro-3-ethoxy-benzyl)piperidin-4-yl]-1H-benzotriazole-5-carboxylic acid,
1-[1-(4-diffuoromethoxy-3-ethoxy-benzyl)-piperidin-4-yl]-1H-benzotriazole-5-carboxylic acid,
1-[1-(3-butoxy-4-methoxy-benzyl)-piperidin-4-yl]-1H-benzotriazole-5-carboxylic acid,
1-[1-(3-isobutoxy-4-methoxy-benzyl)piperidin-4-yl]-1H-benzotriazole-5-carboxylic acid,
1-[1-(3-cyclopentyloxy-4-methoxy-benzyl)piperidin-4-yl]-1H-benzotriazole-5-carboxylic acid,
1-[1-(3,5-diethoxy-benzyl)-piperidin-4-yl]-1H-benzotriazole-5-carboxylic acid,
1-[1-(3,5-diethoxy-4-fluoro-benzyl)-piperidin-4-yl]-1H-benzotriazole-5-carboxylic acid,
1-[1-(4-chloro-3,5-diethoxy-benzyl)-piperidin-4-yl]-1H-benzotriazole-5-carboxylic acid,
1-[1-(4-bromo-3,5-diethoxy-benzyl)-piperidin-4-yl]-1H-benzotriazole-5-carboxylic acid,
1-[1-(3,5-diethoxy-4-pyrrol-1-yl-benzyl)-piperidin-4-yl]-1H-benzotriazole-5-carboxylic acid,
1-[1-(4-bromo-3,5-diethoxy-benzyl)-piperidin-4-yl]-1,5-dihydro-imidazo[4,5-c]pyridin-4-one,
1-[1-(3,5-diethoxy-4-pyrrol-1-yl-benzyl)-piperidin-4-yl]-1,5-dihydro-imidazo[4,5-c]pyridin-4-one,
1-[1-(2,6-diethoxy-4'-fluoro-biphenyl-4-ylmethyl)-piperidin-4-yl]-1,5-dihydro-imidazo[4,5-c ]pyridin-4-one,
2-[1-(3,5-diethoxy-4-pyrrol-1-yl-benzyl)-piperidin-4-yl]-5-methoxy-2,3-dihydro-isoindo-1-one,
or pharmaceutically acceptable salts thereof.

18. A pharmaceutical composition, comprising a therapeutically effective amount of a compound according to claim 1 as well as a pharmaceutically acceptable carrier and/or adjuvant.

* * * * *